United States Patent
Humphreys et al.

(10) Patent No.: US 10,745,412 B2
(45) Date of Patent: Aug. 18, 2020

(54) PROCESSES FOR PREPARING ACC INHIBITORS AND SOLID FORMS THEREOF

(71) Applicant: Gilead Sciences, Inc., Foster City, CA (US)

(72) Inventors: Luke Humphreys, Edmonton (CA); Mark E. Scott, Edmonton (CA)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/689,811

(22) Filed: Nov. 20, 2019

(65) Prior Publication Data
US 2020/0199147 A1 Jun. 25, 2020

Related U.S. Application Data

(62) Division of application No. 15/910,744, filed on Mar. 2, 2018, now Pat. No. 10,519,165.

(60) Provisional application No. 62/553,300, filed on Sep. 1, 2017, provisional application No. 62/466,915, filed on Mar. 3, 2017.

(51) Int. Cl.
| | |
|---|---|
| *C12P 7/42* | (2006.01) |
| *C07D 495/04* | (2006.01) |
| *C07D 309/12* | (2006.01) |
| *A61P 3/00* | (2006.01) |
| *C07D 493/10* | (2006.01) |

(52) U.S. Cl.
CPC .............. *C07D 495/04* (2013.01); *A61P 3/00* (2018.01); *C07D 309/12* (2013.01); *C07D 493/10* (2013.01); *C12P 7/42* (2013.01); *C07B 2200/13* (2013.01)

(58) Field of Classification Search
CPC ....................................................... C12P 7/42
See application file for complete search history.

(56) References Cited

U.S. PATENT DOCUMENTS

| | | |
|---|---|---|
| 8,969,557 B2 | 3/2015 | Harriman et al. |
| 9,453,026 B2 | 9/2016 | Harriman et al. |
| 9,944,655 B2 | 4/2018 | Harriman et al. |
| 10,183,951 B2 | 1/2019 | Amedio, Jr. et al. |
| 10,519,165 B2 | 12/2019 | Geier et al. |
| 2013/0123231 A1 | 5/2013 | Harriman et al. |
| 2019/0016732 A1 | 1/2019 | Bhat et al. |
| 2019/0225623 A1 | 7/2019 | Calimsiz |

FOREIGN PATENT DOCUMENTS

| | | |
|---|---|---|
| WO | WO 2017/151816 | 9/2017 |
| WO | WO 2018/133858 | 7/2018 |
| WO | WO 2018/161008 | 9/2018 |
| WO | WO 2019/066467 | 4/2019 |

OTHER PUBLICATIONS

Mělnický et al., Synthesis, (2013), 45(17), 2447-2457. (Year: 2013).*
U.S. Appl. No. 16/490,453, filed Aug. 30, 2019, Ghosh et al.
U.S. Appl. No. 16/577,455, filed Sep. 20, 2019, Bhat et al.
U.S. Appl. No. 16/598,411, filed Oct. 10, 2019, Alexander et al.
Caira, "Crystalline Polymorphism of Organic Compounds", Topics in Current Chemistry, vol. 198, pp. 163-288 (1998).
Chandramouli et al, "Review on cocrystal as an approach with newer implications in pharmaceutical field," International Journal of Medicinal Chemistry & Analysis, vol. 2, pp. 91-100 (2012).
Emerson et al, "Optical rotatory dispersion. Part XIX A series of acids, imidazolines, amidinium chlorides, and their copper complexes, related to mandelic acid", Journal of the Chemical Society, pp. 4887-4814 (1965).
International Search Report and Written Opinion dated Jul. 3, 2018 for PCT/US2018/020747. 16 pages.

* cited by examiner

*Primary Examiner* — Laura L Stockton
(74) *Attorney, Agent, or Firm* — Sheppard Mullin Richter & Hampton LLP

(57) ABSTRACT

The present disclosure provides solid forms, including a salt or co-crystal, of Compound I:

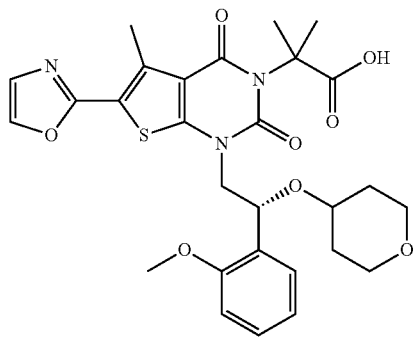

which exhibits Acetyl-CoA carboxylase ("ACC") inhibitory activity and may be useful in treating ACC mediated diseases. Also provided herein are processes or steps for the preparation of a Compound I and intermediates useful for the processes or steps described herein.

2 Claims, 17 Drawing Sheets

PROCESSES FOR PREPARING ACC INHIBITORS AND SOLID FORMS THEREOF

CROSS REFERENCE TO RELATED APPLICATIONS

This application is a divisional of U.S. application Ser. No. 15/910,744, filed Mar. 2, 2018, now U.S. Pat. No. 10,519,165, which claims the benefit under 35 U.S.C. § 119(e) to U.S. Provisional Application No. 62/466,915, filed Mar. 3, 2017, and U.S. Provisional Application No. 62/553,300, filed Sep. 1, 2017, the entireties of which are incorporated herein by reference.

FIELD

The present disclosure relates generally to the preparation of compounds for treating Acetyl-CoA carboxylase ("ACC") mediated diseases and the intermediates prepared thereby. Also included are solid forms of compounds useful for treating ACC mediated diseases.

BACKGROUND

Therapeutic agents that function as inhibitors of ACC have the potential to remedy or improve the lives of patients in need of treatment for diseases or conditions such metabolic disorders (such as obesity, non-alcoholic fatty liver disease, and non-alcoholic steatohepatitis (NASH)), cancers, neurological disorders, and infectious diseases. There is a need for improved or alternate processes to prepare compounds, as well as additional solid forms of compounds, for treating ACC mediated diseases.

SUMMARY

The present disclosure provides forms of Compound I or a compound of formula (I) having the formula:

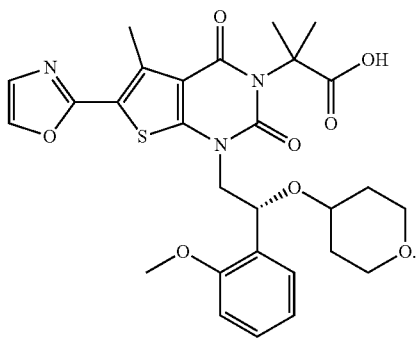

(I)

Additionally, the disclosure provides processes for making salts, co-crystals, solvates, hydrates, and analogs of Compound I. The present disclosure provides processes for making Compound I or a compound of formula (I). Also, the present disclosure provides processes for making analogs of Compound I and intermediates useful for the processes for making Compound I or analogs or forms thereof.

The present disclosure also relates to various crystalline or amorphous forms of Compound I or a salt, a co-crystal, a solvate, or a hydrate thereof, processes of making Compound I and its various crystalline or amorphous forms, pharmaceutical compositions comprising various crystalline or amorphous forms of Compound I or a salt, a co-crystal, a solvate, or a hydrate thereof, and methods of using such forms or pharmaceutical compositions. Compounds having structures described by one or more of formula (A), (B), (C), (D), (E), (F), (G), (H), (I), (J), (K), (L), (M), (N), (O), (P), (R), (S), (T), (U), (V), or other formulas or compounds disclosed herein (e.g. numbered compounds A-1, A-2, B-1, B-2, C-1, D-1, E-1, E-2, G-1, H-1, J-1, K-1, L-1, N-1, O-1, P-1, R-1, S-1, T-1, U-1, V-1, etc.) may refer to a salt, a co-crystal, a solvate, or a hydrate thereof. In some embodiments, provided herein are crystalline or amorphous forms of compounds having structures described by one or more of formula (A), (B), (C), (D), (E), (F), (G), (H), (I), (J), (K), (L), (M), (N), (O), (P), (R), (S), (T), (U), (V), or other formulas or compounds disclosed herein (e.g. numbered compounds A-1, A-2, B-1, B-2, C-1, D-1, E-1, E-2, G-1, H-1, J-1, K-1, L-1, N-1, O-1, P-1, R-1, S-1, T-1, U-1, V-1, etc.).

In addition, the present disclosure discloses the compounds that are prepared by the processes or steps described herein. Additionally, the disclosure provides a composition comprising the compounds prepared by the processes or steps described herein. Moreover, the disclosure provides uses of the compounds prepared by the processes or steps described herein in the manufacture of medicaments treating ACC mediated diseases.

DETAILED DESCRIPTION

Definitions and General Parameters

Figure 1:
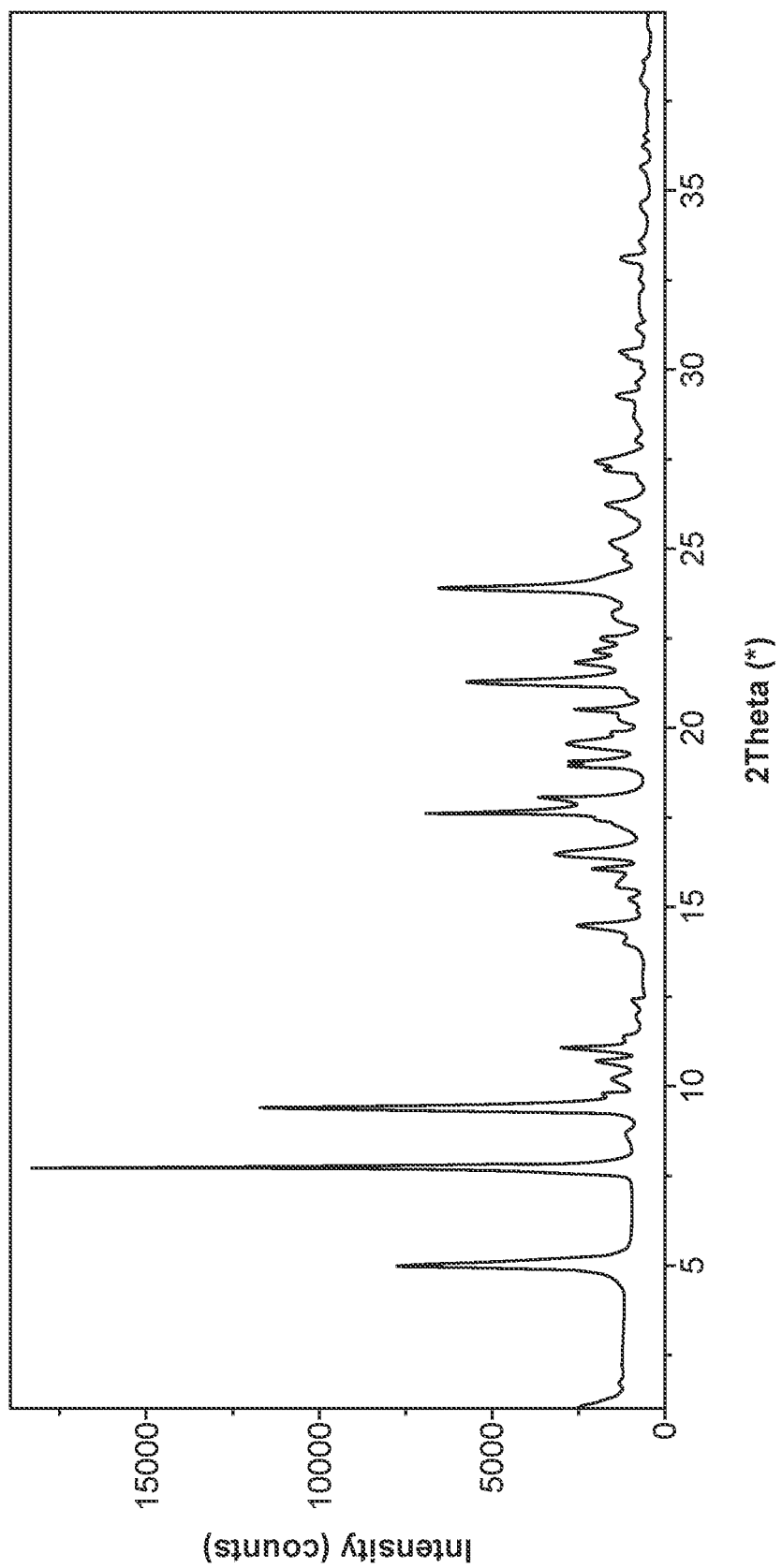
FIG. 1 shows an X-ray powder diffractogram of Compound I Choline Form I.

The following description sets forth exemplary methods, parameters and the like. It should be recognized, however, that such description is not intended as a limitation on the scope of the present disclosure but is instead provided as a description of exemplary embodiments.

A used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. For example, when used in the context of quantitative measurements, the term "about" would refer to the indicated amount ±10%, ±5% or ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)3CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cyclohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-20}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" refers to an unsaturated non-aromatic cyclic alkyl group, with one or more ring heteroatoms independently selected from nitrogen, oxygen and sulfur. As used herein, "heterocyclyl" or "heterocyclic ring" refers to rings that are saturated or partially saturated unless otherwise indicated, e.g., in some embodiments "heterocyclyl" or "heterocyclic ring" refers to rings that are partially saturated where specified. The term "heterocyclyl" or "heterocyclic ring" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5] nonanyl, 2-oxa-6-azaspiro[3.4]octanyl, and 6-oxa-1-azaspiro[3.3]heptanyl.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl;

"substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that may be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound described herein when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof may generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base "salts" by virtue of the presence of amino and/or carboxyl groups or groups similar thereto.

Base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroayl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to $NH(heteroaryl)_2$, wherein "heteroaryl" is as defined herein and so on. Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

In some cases, the "salt" of a given compound is a pharmaceutically acceptable salt. The term "pharmaceutically acceptable salt" of a given compound refers to salts that retain the biological effectiveness and properties of the given compound, and which are not biologically or otherwise undesirable. Pharmaceutically acceptable base addition salts may be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, diethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "co-crystal" refers to a molecular complex of an ionized or non-ionized Compound I (or any other compound disclosed herein) and one or more non-ionized co-crystal formers (such as a pharmaceutically acceptable salt) connected through non-covalent interactions.

The term "solvate" refers to a crystal form with either a stoichiometric or non-stoichiometric amount of solvent incorporated into the crystal structure. Similarly, the term "hydrate" refers specifically to a crystal form with either a stoichiometric or non-stoichiometric amount of water incorporated into the crystal structure.

The term "reaction conditions" is intended to refer to the physical and/or environmental conditions under which a chemical reaction proceeds. The term "under conditions sufficient to" or "under reaction conditions sufficient to" is intended to refer to the reaction conditions under which the desired chemical reaction may proceed. Examples of reaction conditions include, but are not limited to, one or more of following: reaction temperature, solvent, pH, pressure, reaction time, mole ratio of reactants, the presence of a base or acid, or catalyst, radiation, concentration, etc. Reaction conditions may be named after the particular chemical reaction in which the conditions are employed, such as, coupling conditions, hydrogenation conditions, acylation conditions, reduction conditions, etc. Reaction conditions for most reactions are generally known to those skilled in the art or may be readily obtained from the literature. Exemplary reaction conditions sufficient for performing the chemical transformations provided herein may be found throughout, and in particular, the examples below. It is also contemplated that the reaction conditions may include reagents in addition to those listed in the specific reaction.

The term "reagent" refers to a substance or compound that may be added to bring about a chemical reaction.

The term "catalyst" refers to a chemical substance that enables a chemical reaction to proceed at a usually faster rate or under different conditions (such as at a lower temperature) than otherwise possible.

The term "reductant" or "reducing agent" refers to a reagent used for the addition of hydrogen to a molecule. Exemplary reducing agents include hydrogen gas ($H_2$) and hydride reagents such as borohydrides, lithium aluminium hydride, diisobutylaluminium hydride (DIBAL-H) and super hydride. Other exemplary reducing agents are as disclosed herein.

The term "leaving group" refers to an atom or a group of atoms that is displaced in a chemical reaction as stable species taking with it the bonding electrons. The non-limiting examples of a leaving group include, halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitrobenzene)-sulfonyloxy, (4-isopropyl-benzene)sulfonyloxy, (2,4,6-tri-isopropyl-benzene)-sulfonyloxy, (2,4,6-trimethylbenzene)sulfonyloxy, (4-tertbutyl-benzene)sulfonyloxy, benzenesulfonyloxy, (4-methoxy-benzene)sulfonyloxy, and the like.

The term "hydroxynitrilase" or "oxynitrilase" or "hydroxynitrile lyase" or "acetone cyanohydrin lyase" refers to an enzyme that catalyzes the chemical reaction: acetone cyanohydrin ⇌ cyanide+acetone.

The term "nitrilase" refers to an enzyme that catalyzes the hydrolysis of nitriles to carboxylic acids and ammonia.

The term "ketoreductase" (also known as "carbonylreductase" or "alcohol dehydrogenase") refers to an enzyme that catalyzes the reduction of a ketone.

The term "enzyme classification number" or "Enzyme Commission number" refers to the numerical classification scheme for enzymes based on the chemical reations they catalyze.

In addition, abbreviations as used herein have respective meanings as follows:

| | |
|---|---|
| °C. | Degree Celsius |
| Ac | Acetate |
| aq | Aqueous |
| ASK1 | Apoptosis signal-regulating kinase 1 |
| br | broad |
| Bu | Butyl |
| Cp | pentamethylcyclopentadienyl |
| CYM | cymene |
| d | Doublet |
| DCM | Dichloromethane |
| DMF | Dimethylformamide |
| DMSO | Dimethylsulfoxide |
| Equiv/equiv. | Equivalents |
| Et | Ethyl |
| EtOAc | Ethyl acetate |
| EtOH | Ethanol |
| g | Gram |
| h | Hour |
| HPLC | High-pressure liquid chromatography |
| Hz | Hertz |
| iPr | Isopropyl |
| J | Coupling constant |
| KHMDS | Potassium bis(trimethylsilyl)amide |
| KOEt | Potassium ethoxide |
| KOMe | Potassium methoxide |
| KO$^t$Bu | Potassium t-butoxide |
| m | Multiplet |
| M | Molar |
| Me | Methyl |
| MeOH | Methanol |
| Mg or mg | Milligram |
| MHz | Mega hertz |
| min(s) | Minute(s) |
| mL | Milliliter |
| Mmol or mmol | Millimole |
| MTBE | Methyl-tert-butyl ether |
| N | Normal |
| NMP | N-Methyl-2-pyrrolidone |
| NMR | Nuclear magnetic resonance |
| P-CYM | Para cymene |
| q | quartet |
| rpm | Revolutions per minute |
| s | Singlet |
| t | Triplet |
| t-Bu | tert-Butyl |
| TGA-MS | Thermogravimetric Analysis/Mass Spectrometry |
| THF | Tetrahydrofuran |
| UPLC | Ultra Performance Liquid Chromatography |
| V or vol | Volumes (mL/g) |
| Wt or w | Weight |
| δ | Chemical shift |
| μL | Microliter |

Compounds and Processes

Compound I may be referred to by formula (I):

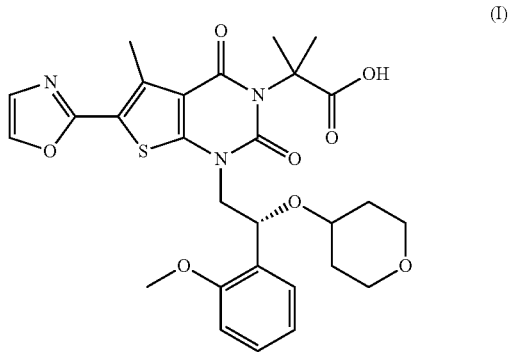 [SMILES: COc1ccccc1[C@H](Cn1c(=O)n(C(C)(C)C(=O)O)c(=O)c2c(C)c(-c3ncco3)sc21)OC1CCOCC1]

(I)

or its chemical name of (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3 (4H)-yl)-2-methylpropanoic acid. U.S. Pat. No. 8,969,557 discloses that Compound I exhibits ACC inhibitory activity.

In the present disclosure, compounds may be presented in the form of chemical structures or names. By way of example, Compound I may be named using ChemBioDraw Ultra 10.0 and it should be understood that other names may be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC).

The present processes may be performed using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of formula (A), (B), (C), (D), (E), (F), (G), (H), (I), (J), (K), (L), (M), (N), (O), (P), (R), (S), (T), (U), (V), or other formulas or compounds disclosed herein (e.g. numbered compounds A-1, A-2, B-1, B-2, C-1, D-1, E-1, E-2, G-1, H-1, J-1, K-1, L-1, N-1, O-1, P-1, R-1, S-1, T-1, U-1, V-1, etc.), may be accomplished as described in the following examples. If available, reagents may be purchased commercially, e.g. from Sigma Aldrich or other chemical suppliers.

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

The compounds of this disclosure may be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions may also be used unless otherwise stated. Optimum reaction conditions may vary with the particular reactants or solvent used, but such conditions may be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds may be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds may be separated using, for example, chiral column chromatography, chiral resolving agents, and the like.

The starting materials for the following reactions are generally known compounds or may be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography may involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents may be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller, C. H., (1975) *J. Chromatogr.*, 113, 3) 283-302). Racemic mixtures of chiral compounds of the disclosure may be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts or co-crystals may be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts or co-crystals may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid may result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds may be formed by reacting asymmetric compounds with enantiomerically pure chiral derivatizing reagents, such as menthyl derivatives, followed by separation of the diastereomers and hydrolysis to yield the free, enantiomerically enriched substrate. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds may be separated and isolated by normal- and reverse-phase chromatography following methods for separation of atropisomeric naphthyl-isoquinolines (Hoye, T., WO 96/15111). By method (3), a racemic mixture of two enantiomers may be separated by chromatography using a chiral stationary phase (Chiral Liquid Chromatography (1989) W. J. Lough, Ed. Chapman and Hall, New York; Okamoto, (1990) J. of Chromatogr. 513:375-378). Enriched or purified enantiomers may be distinguished by methods used to distinguish other chiral molecules with asymmetric carbon atoms, such as optical rotation and circular dichroism.

As described herein, some embodiments provide processes for making a compound of formula (I), forms or analogs thereof. Without being bound by any hypothesis, forms or analogs of Compound I may exhibit suitable properties, including and not being limited to potent and exhibit improved pharmacokinetic and/or pharmacodynamic profiles, for treating ACC-mediated condition.

By way of example, a form of Compound I may refer to a salt, a co-crystal, a solvate, or a hydrate of Compound I. By additional examples, an analog of Compound I may refer to a compound of formula (F) or Compound F.

Compounds having structures described by one or more of formula (A), (B), (C), (D), (E), (F), (G), (H), (I), (J), (K), (L), (M), (N), (O), (P), (R), (S), (T), (U), (V), or other formulas or compounds disclosed herein (e.g. numbered compounds A-1, A-2, B-1, B-2, C-1, D-1, E-1, E-2, G-1, H-1, J-1, K-1, L-1, N-1, O-1, P-1, R-1, S-1, T-1, U-1, V-1, etc.) may refer to a salt, a co-crystal, a solvate, or a hydrate thereof. In some embodiments, provided herein are crytalline or amorphous forms of compounds having structures described by one or more of formula (A), (B), (C), (D), (E), (F), (G), (H), (I), (J), (K), (L), (M), (N), (O), (P), (R), (S), (T), (U), (V), or other formulas or compounds disclosed herein (e.g. numbered compounds A-1, A-2, B-1, B-2, C-1, D-1, E-1, E-2, G-1, H-1, J-1, K-1, L-1, N-1, O-1, P-1, R-1, S-1, T-1, U-1, V-1, etc.).

Scheme 1 represents an exemplary synthesis of a compound of formula (F) and may be carried out according to the embodiments described herein.

Scheme 1

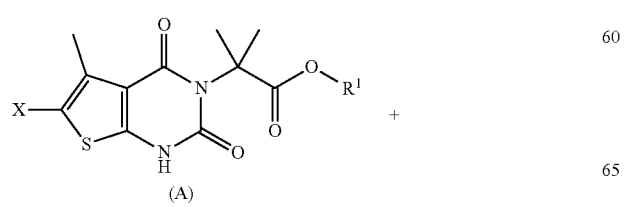

(A)

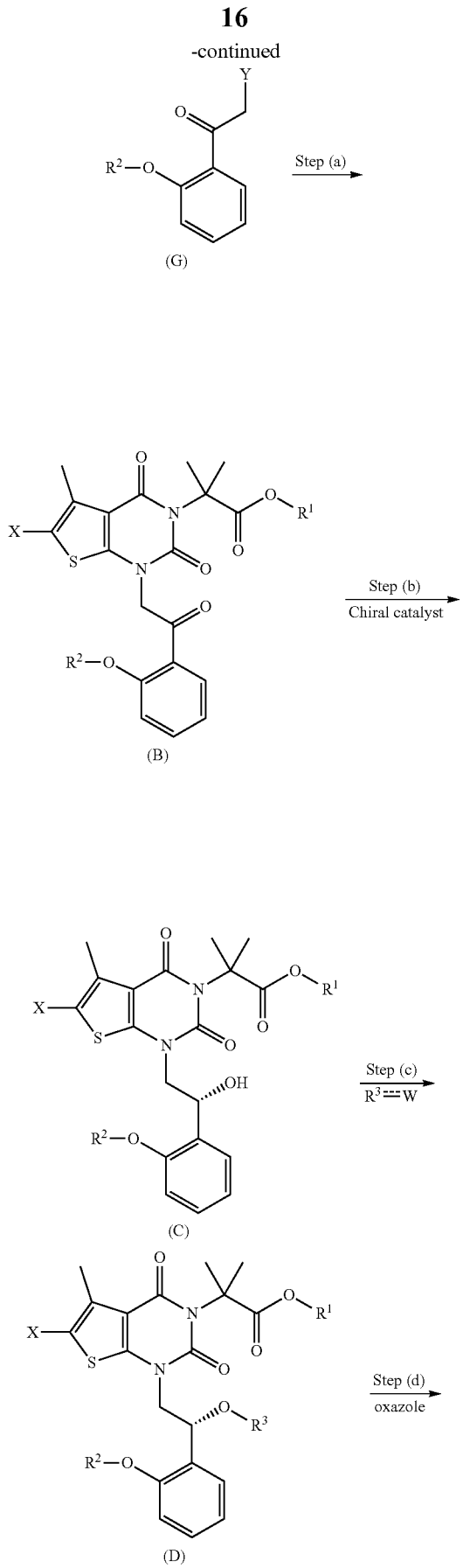

-continued

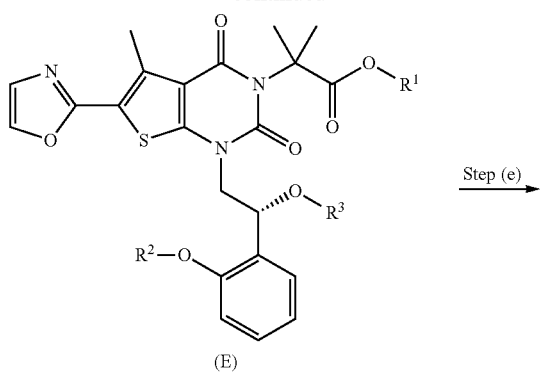

(E)

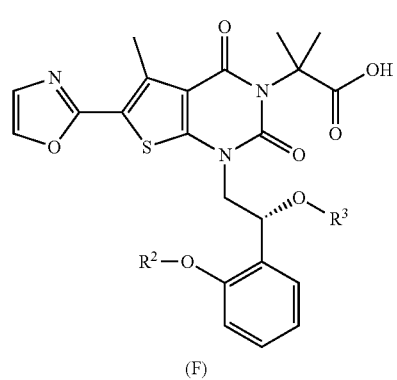

(F)

In some embodiments, X is halo; Y is a leaving group; R¹ is C₁₋₆ alkyl or aryl; R² is C₁₋₃ alkyl; R³ is cycloalkyl or heterocyclyl, each of which is optionally substituted; and when ═ is a single bond, W is a leaving group, or when ═ is a double bond, W is O. In some embodiments, X is halo; Y is a leaving group; R¹ is C₁₋₆ alkyl, C₁₋₂-alkylene-aryl, or aryl; R² is C₁₋₃ alkyl; R³ is cycloalkyl or heterocyclyl, each of which is optionally substituted; and when ═ is a single bond, W is a leaving group, or when ═ is a double bond, W is O.

In one embodiment, the present disclosure provides for a method for preparing a compound of formula (F):

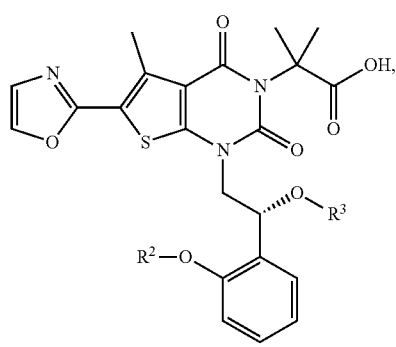

or a salt, a co-crystal, a solvate, or a hydrate thereof.

In some embodiments, step (a) comprises contacting a compound of formula (A):

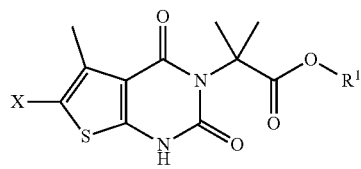

with a compound of formula (G):

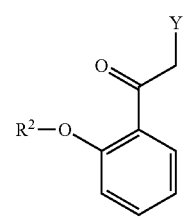

under conditions sufficient to form a compound of formula (B):

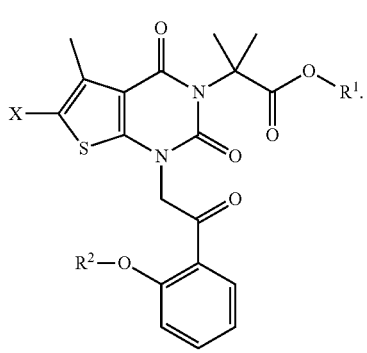

In some embodiments, step (b) comprises hydrogenating a compound of formula (B) in the presence of a chiral catalyst under conditions sufficient to form a compound of formula (C):

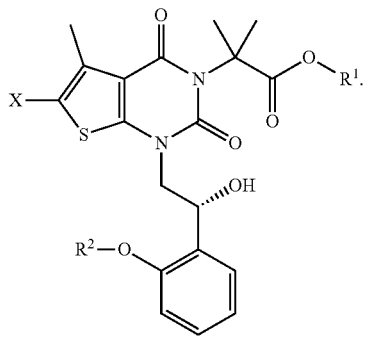

In some embodiments, provided is a compound of formula (C), or a salt, co-crystal, solvate, or hydrate thereof.

In some embodiments, step (c) comprises contacting a compound of formula (C) with a compound of formula (H):

$$R^3 = W \quad (H)$$

under conditions sufficient to form a compound of formula (D):

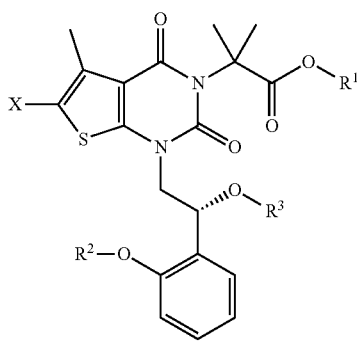

wherein:
when $=$ is a single bond, W is halo, mesylate, tosylate, or trichloroacetimidate, or when $=$ is a double bond, W is O; and
$R^3$ is cycloalkyl or heterocyclyl, each of which is optionally substituted.

In some embodiments, step (d) comprises contacting a compound of formula (D) with oxazole under conditions sufficient to form a compound of formula (E):

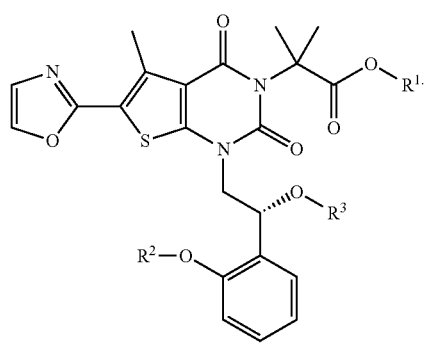

In some embodiments, step (e) comprises hydrolyzing a compound of formula (E) under conditions sufficient to form a compound of formula (F).

In some embodiments, X is halo;
Y is a leaving group;
$R^1$ is $C_{1-6}$ alkyl or aryl; and
$R^2$ is $C_{1-3}$ alkyl.
In some embodiments, X is halo;
Y is a leaving group;
$R^1$ is $C_{1-6}$ alkyl, $C_{1-2}$-alkylene-aryl, or aryl; and
$R^2$ is $C_{1-3}$ alkyl.
In some embodiments, X is Cl, Br, or I. In some embodiments, X is Cl. In some embodiments, X is Br. In some embodiments, X is I.
In some embodiments, $R^1$ is $C_{1-6}$ alkyl. In some embodiments, $R^1$ is methyl. In some embodiments, $R^1$ is ethyl. In some embodiments, $R^1$ is propyl. In some embodiments, $R^1$ is tert-butyl.

In some embodiments, $R^1$ is $C_{6-10}$ aryl. In some embodiments, $R^1$ is $C_{1-2}$-alkylene-aryl. In some embodiments, $R^1$ is benzyl.
In some embodiments, $R^1$ is benzyl or tert-butyl.
In some embodiments, $R^2$ is methyl or ethyl. In some embodiments, $R^2$ is methyl. In some embodiments, $R^2$ is ethyl. In some embodiments, $R^2$ is propyl.
In some embodiments, Y is halo. In some embodiments, Y is Cl. In some embodiments, Y is Br. In some embodiments, Y is I.
In some embodiments, when $=$ is a single bond in (H), W is a leaving group. In some embodiments, when $=$ is a single bond, W is halo. In some embodiments, when $=$ is a single bond, W is Cl. In some embodiments, when $=$ is a single bond, W is Br. In some embodiments, when $=$ is a single bond, W is I. In some embodiments, when $=$ is a single bond, W is mesylate or tosylate. In some embodiments, when $=$ is a single bond, W is trichloroacetimidate. In some embodiments, when $=$ is a double bond, W is O.
In some embodiments, $R^3$ is cycloalkyl. In some embodiments, $R^3$ is substituted cycloalkyl. In some embodiments, $R^3$ is cycloalkyl substituted with hydroxyl. In some embodiments, $R^3$ is substituted $C_{6-10}$ cycloalkyl. In some embodiments, $R^3$ is $C_{6-10}$ cycloalkyl substituted with hydroxyl. In some embodiments, $R^3$ is a substituted cyclohexyl. In some embodiments, $R^3$ is cyclohexyl substituted with hydroxyl.
In some embodiments, $R^3$ is heterocyclyl. In some embodiments, $R^3$ is a 5-6 membered heterocyclyl having at least one heteroatom selected from oxygen, nitrogen, and sulfur. In some embodiments, $R^3$ is tetrahydropyranyl.
In some embodiments, X is halo; Y is a leaving group; $R^1$ is $C_{1-6}$ alkyl or aryl; $R^2$ is $C_{1-3}$ alkyl; and $R^3$ is heterocyclyl. In some embodiments, X is halo; Y is a leaving group; $R^1$ is $C_{1-6}$ alkyl or aryl; $R^2$ is $C_{1-3}$ alkyl; and $R^3$ is $C_{6-10}$ cycloalkyl substituted with hydroxyl. In some embodiments, X is halo; Y is a leaving group; $R^1$ is $C_{1-6}$ alkyl, $C_{1-2}$-alkylene-aryl, or aryl; $R^2$ is $C_{1-3}$ alkyl; and $R^3$ is heterocyclyl. In some embodiments, X is halo; Y is a leaving group; $R^1$ is $C_{1-6}$ alkyl, $C_{1-2}$-alkylene-aryl, or aryl; $R^2$ is $C_{1-3}$ alkyl; and $R^3$ is $C_{6-10}$ cycloalkyl substituted with hydroxyl.
In some embodiments, X is halo; Y is halo; $R^1$ is $C_{1-6}$ alkyl; $R^2$ is $C_{1-3}$ alkyl; and $R^3$ is heterocyclyl. In some embodiments, X is halo; Y is halo; $R^1$ is $C_{6-10}$ aryl; $R^2$ is $C_{1-3}$ alkyl; and $R^3$ is heterocyclyl. In some embodiments, X is halo; Y is halo; $R^1$ is $C_{1-2}$-alkylene-aryl; $R^2$ is $C_{1-3}$ alkyl; and $R^3$ is heterocyclyl. In some embodiments, X is halo; Y is halo; $R^1$ is $C_{1-6}$ alkyl; $R^2$ is $C_{1-3}$ alkyl; and $R^3$ is tetrahydropyranyl. In some embodiments, X is halo; Y is halo; $R^1$ is $C_{6-10}$ aryl; $R^2$ is $C_{1-3}$ alkyl; and $R^3$ is tetrahydropyranyl. In some embodiments, X is halo; Y is halo; $R^1$ is $C_{1-2}$-alkylene-aryl; $R^2$ is $C_{1-3}$ alkyl; and $R^3$ is tetrahydropyranyl.
In some embodiments, the method provides for a compound of formula (F), or a salt or a co-crystal thereof. In some embodiments, the method provides for a compound of formula (F), or a pharmaceutically acceptable salt thereof. In some embodiments, the method provides for a compound of formula (F), or a pharmaceutically acceptable co-crystal thereof.
In some embodiments, compound of formula (C), compound of formula (D), compound of formula (E), or compound of formula (F), is present in an enantiomeric excess (e.e.) of about 90 to about 99.9 percent. In some embodiments, compound of formula (C), compound of formula (D), compound of formula (E), or compound of formula (F) is present in an enantiomeric excess (e.e.) of at least about 90, 91, 92, 93, 94, 95, 96, 97, 97.5, 98.0, 98.5, 99.0, 99.5, 99.7, 99.8, 99.9, or 99.95 percent. In some embodiments, compound of formula (F) is present in an enantiomeric excess (e.e.) of at least about 95, 96, 97, 97.5, 98.0, 98.5, 99.0, 99.5, 99.7, 99.8, 99.9, or 99.95 percent.

As used herein, a compound of formula (A), a compound of formula (A-1), a compound of formula (A-2), a compound of formula (B), a compound of formula (B-1), a compound of formula (B-2), a compound of formula (C), a compound of formula (C-1), a compound of formula (D), a compound of formula (D-1), a compound of formula (E), a compound of formula (E-1), a compound of formula (E-2), a compound of formula (F), a compound of formula (G), or a compound of formula (G-1) may also be referred to as Compound A, Compound A-1, Compound A-2, Compound B, Compound B-1, Compound B-2, Compound C, Compound C-1, Compound D, Compound D-1, Compound E, Compound E-1, Compound E-2, Compound F, Compound G, or Compound G-1; receptively. Compound of formula (A), compound of formula (B), and compound of formula (G) may be prepared as described, for example, in U.S. Pat. No. 8,969,557, or according to methods known in the art.

In some embodiments, the reaction conditions of step (a) comprise a base. In some embodiments, the base is a carbonate base. In some embodiments, the carbonate base is an alkali metal carbonate. In some embodiments, the base is sodium carbonate, sodium bicarbonate, potassium carbonate, potassium bicarbonate, cesium carbonate, cesium bicarbonate, potassium phosphate tribasic, or potassium phosphate dibasic. In some embodiments, the alkali metal carbonate is potassium carbonate or cesium carbonate. In some embodiments, the alkali metal carbonate is potassium carbonate. In some embodiments, the alkali metal carbonate is potassium bicarbonate. In some embodiments, the alkali metal carbonate is cesium carbonate. In some embodiments, the alkali metal carbonate is cesium bicarbonate. In some embodiments, the base is potassium phosphate tribasic or potassium phosphate dibasic. In some embodiments, the reaction conditions of step (a) proceeds in a polar solvent. In some embodiments, the polar solvent is a polar aprotic solvent. In some embodiments, the polar aprotic solvent is N-methylpyrrolidone (NMP). In some embodiments, the polar aprotic solvent is N,N-dimethylformamide (DMF). In some embodiments, the polar aprotic solvent is N,N-dimethylacetamide (DMA).

In some embodiments, the reaction conditions of step (b) comprise a hydrogen source. Suitable hydrogen sources/conditions are known in the art as described, for example, in Wang et al, Chem. Rev. 2015, 115, 6621-6686. In some embodiments, the reaction conditions of step (b) comprise $H_2$ and a catalyst including but not limited to those described in Xie et al., Synthesis 2015, 47, 460-471. In some embodiments, the reaction conditions of step (b) comprise formic acid. In some embodiments, the reaction conditions of step (b) comprise an organic amine and formic acid. In some embodiments, the organic amine is triethylamine.

In some embodiments, the chiral catalyst is a Ruthenium-based catalyst or an Iridium-based catalyst. In some embodiments, the chiral catalyst is a Ruthenium-based catalyst. In some embodiments, the chiral catalyst is an Iridium-based catalyst. Any Ruthenium-based or Iridium-based catalysts known in the art may be used, such as those described in Wang et al, Chem. Rev. 2015, 115, 6621-6686. The Ruthenium-based catalyst may include, but is not limited to, RuCl(p-cymene)[Ts-DPEN] ([N-[2-(Amino-κN)-1,2-diphenylethyl]-4-methylbenzenesulfonamidato-N]chloro[(1,2,3,4,5,6-η)-1-methyl-4-(1-methylethyl)benzene]-ruthenium), Teth-TsDpen RuCl (Chloro[1,2-diphenyl-N1-(3-phenylpropyl)-N2-(p-toluenesulfonyl)-1,2-ethanediamine]ruthenium (II)), RuCl[FsDPEN](p-cymene) ([N-[(2-(Amino-κN)-1,2-diphenylethy]-2,3,4,5,6-pentafluorobenzenesulfonamidato-κN]chloro[(1,2,3,4,5,6-η)-1-methyl-4-(1-methylethyl)benzene]-ruthenium), RuCl[TsDPEN](mesitylene) ([N-[(2-(Amino-κN)-1,2-diphenylethyl]-4-methylbenzenesulfonamidato-N] chloro[(1,2,3,4,5,6-)-1,3,5-trimethylbenzene]-ruthenium), RuCl[(p-cymene(BINAP)Cl (Chloro[2,2'-bis(diphenylphosphino)-1,1'-binaphthyl] (p-cymene)ruthenium (II) chloride), RuCl[(p-cymene(Tol-BINAP)Cl (Chloro[2,2'-bis(di-p-tolylphosphino)-1,1'-binaphthyl](p-cymene)ruthenium(II) Chloride), RuCl[(p-cymene(DM-BINAP)Cl (Chloro[2,2'-bis(di-(3,5-xylyl)phosphino)-1,1'-binaphthyl](p-cymene)ruthenium(II) chloride), RuCl[(p-cymene(H8-BINAP)Cl (Chloro[2,2'-bis(diphenylphosphino)-5,5',6,6',7,7',8,8'-octahydro-1,1'-binaphthyl](p-cymene)ruthenium(II) chloride), RuCl[(p-cymene(SEGPHOS®)Cl (Chloro[5,5'-bis[di(3,5-xylyl)phosphino]-4,4'-bi-1,3-benzodioxole] (p-cymene)ruthenium(II) chloride), RuCl[(p-cymene(DM-SEGPHOS®)Cl (Chloro[(5,5'-bis[di(3,5-xylyl)phosphino]-4,4'-bi-1,3-benzodioxole](p-cymene)ruthenium(II) chloride), and RuCl[(p-cymene(DTBM-SEGPHOS®)Cl (Chloro[(R)-(−)5,5'-bis[bis(3,5-di-tert-butyl-4-methoxyphenyl)phosphino]-4,4'-bi-1,3-ben zodioxole](p-cymene)ruthenium(II) chloride). Other chiral catalysts known in the art may be used, including but not limited to Corey-Bakshi-Shibata catalyst. Another non-limiting example of a chiral catalyst that may be used is a chiral reagent such as B-Chlorodiisopinocampheylborane. In some embodiments, the chiral catalyst is a catalyst as described below for step (c) of Scheme 3.

In some embodiments, the reaction conditions of step (c) comprise a base. In some embodiments, the base is an organic base. In some embodiments, the organic base is Lewis base. In some embodiments, the organic base is 1,8-diazabicyclo[5.4.0]undec-7-ene or Barton's base.

In some embodiments, wherein W is trichloroacetimidate or O, the reaction conditions of step (c) comprise a Lewis or Bronsted acid.

In some embodiments, the reaction conditions of step (d) comprise a coupling of compound of formula (D) with an oxazole synthon (oxazole or oxazole metalate), thereby forming compound of formula (E). In some embodiments, the coupling is a metal-catalyzed coupling. In some embodiments, the metal-catalyzed coupling is a Negishi coupling. One of skill in the art will appreciate that a Negishi coupling is a transition metal-catalyzed cross-coupling of an organic halide compound with an organozinc compound. In some embodiments, the oxazole synthon is an oxazole zincate. In some embodiments, the oxazole zincate is formed by metal exchange between 2-lithio-oxazole and a zinc salt. In some embodiments the zinc salt is $ZnCl_2$. In some embodiments, the 2-lithio-oxazole is formed by treating oxazole with n-butyllithium. In some embodiments, the 2-lithio-oxazole is formed at a temperature below −40° C. In some embodiments, the 2-lithio-oxazole is formed at a temperature below about −40° C. In some embodiments, the 2-lithio-oxazole is formed at a temperature below −60° C. In some embodiments, the 2-lithio-oxazole is formed at a temperature below about −60° C. In some embodiments, the metal catalyst is a palladium catalyst. In some embodiments, the palladium catalyst is $Pd(PPh_3)_4$. In some embodiments, compound of formula (E) is purified by crystallization.

In some embodiments, the reaction conditions of step (d) comprise a metalating agent. In some embodiments, the oxazole is treated with a metalating agent selected from isopropyl magnesium chloride, isopropyl magnesium bromide, TMPZnCl—LiCl, TMPMgCl—LiCl, and isopropyl magnesium chloride/lithium chloride (wherein TMP refers to 2,2,6,6,-tetramethylpiperidine). In some embodiments, the metalating agent is isopropyl magnesium chloride. In some embodiments, the oxazole is treated with isopropyl magnesium chloride (2M in THF). In some embodiments, the oxazole is treated with a metalating agent at about −20° C. to about −10° C. In some embodiments, the oxazole is treated with a metalating agent at about −15° C. In some embodiments, the solvent is tetrahydrofuran, 2-methyltetrahydrofuran, or a mixture thereof. In some embodiments, the solvent is tetrahydrofuran and 2-methyltetrahydrofuran. In some embodiments, the reaction further comprises adding $ZnCl_2$ to form an oxazole zincate. In some embodiments, the reaction further comprises adding $ZnCl_2$ as a solution in 2-methyltetrahydrofuran. In some embodiments, the catalyst used in the Negishi coupling is a palladium catalyst. In some embodiments, the catalyst used in the Negishi coupling is a palladium catalyst selected from $Pd(PPh_3)_4$, tBuXPhos Pd precatalyst, XPhos Pd precatalyst, RuPhos Pd precatalyst, and Pd-PEPPSI-IPent (dichloro[1,3-bis(2,6-di-3-pentylphenyl)imidazol-2-ylidene](3-chloropyridyl)palladium(II)). Such precatalysts are described in, for example, Bruneau et al., ACS Catal., 2015, 5(2), pp. 1386-1396. In some embodiments, the catalyst is formed in situ via a suitable palladium source and appropriate chiral ligands according to methods known in the art. In some embodiments, the catalyst is $Pd(PPh_3)_4$. In some embodiments, the reaction mixture is heated to greater than about 50° C. after addition of $ZnCl_2$. In some embodiments, the reaction mixture is heated to about 65° C.

In some embodiments, the reaction conditions of step (e) comprise an acid. In some embodiments, the acid is sulfuric acid, tetrafluoroboric acid, methanesulfonic acid, nitric acid, or hydrochloric acid. In some embodiments, the acid is sulfuric acid. In some embodiments, the acid is hydrochloric acid.

In some embodiments, the reaction conditions of step (e) comprise a co-solvent. In some embodiments, the co-solvent is an alcohol. In some embodiments, the co-solvent is 2-propanol, t-butanol, t-amyl alcohol, ethanol, or acetonitrile.

In some embodiments, the reaction conditions of step (e) comprise a temperature of about 5 and 10° C. In some embodiments, the reaction conditions of step (e) comprise a temperature between about 0 and about 20° C. In some embodiments, the reaction conditions of step (e) comprise between about 2 and about 8° C.

Alternative reaction conditions, such as steps (a), (d), or (e), may be performed as described, for example, in U.S. Pat. No. 8,969,557.

Also provided herein are methods for preparing a compound of formula (C):

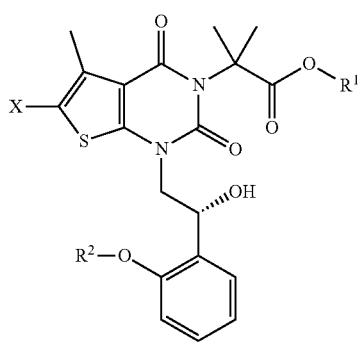

comprising:
hydrogenating a compound of formula (B):

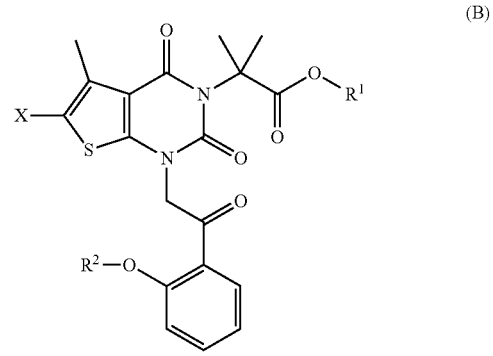

in the presence of a chiral catalyst under reaction conditions sufficient to form a compound of formula (C);
wherein X is halo or heteroaryl;
$R^1$ is $C_{1-6}$ alkyl or aryl; and
$R^2$ is $C_{1-3}$ alkyl.

In some embodiments, X is halo or heteroaryl; $R^1$ is $C_{1-6}$ alkyl, $C_{1-2}$-alkylene-aryl, or aryl; and $R^2$ is $C_{1-3}$ alkyl.

In some embodiments, the method provides for compound of formula (C) in an enantiomeric excess (e.e.) of about 90 to about 99.9 percent. In some embodiments, the method provides for compound of formula (C) in an enantiomeric excess (e.e.) of at least about 90, 91, 92, 93, 94, 95, 96, 97, 97.5, 98.0, 98.5, 99.0, 99.5, 99.7, 99.8, 99.9, or 99.95 percent.

In some embodiments, provided is a compound of formula (C), or a salt, co-crystal, solvate, or hydrate thereof.

In some embodiments, X is halo. In some embodiments, X is Cl. In some embodiments, X is Br. In some embodiments, X is I.

In some embodiments, X is a 5-6 membered heteroaryl ring having one or more heteroatoms selected from N, O, or S. In some embodiments, X is a 5-6 membered heteroaryl ring having one to three heteroatoms selected from N, O, or S. In some embodiments, X is oxazole.

In some embodiments, the reaction conditions of the hydrogenation comprise a hydrogen source. Suitable hydrogen sources/conditions are known in the art as described, for example, in Wang et al, Chem. Rev. 2015, 115, 6621-6686. In some embodiments, the reaction conditions of the hydrogenation comprise $H_2$ and a catalyst including but not limited to those described in Xie et al., Synthesis 2015, 47, 460-471. In some embodiments, the reaction conditions of the hydrogenation comprise formic acid. In some embodiments, the reaction conditions of the hydrogenation comprise an organic amine with formic acid. In some embodiments, the organic amine is triethylamine. In some embodiments, the reaction conditions of the hydrogenation comprise formic acid and triethylamine, ammonium formate, or formic acid and sodium formate. In some embodiments, the reaction conditions of the hydrogenation comprise formic acid and trimethylamine. In some embodiments, the reaction conditions of the hydrogenation comprise formic acid and triethylamine. In some embodiments, the reaction conditions of the hydrogenation comprise a base. In some embodiments, the base is a t-butoxide. In some embodiments, the base is sodium t-butoxide or potassium t-butoxide. In some embodiments, when a base is present, the solvent is a polar solvent. The solvent may include, but is not limited to, isopropanol.

In some embodiments, the chiral catalyst is a Ruthenium-based catalyst or an Iridium-based catalyst. In some embodiments, the chiral catalyst is a Ruthenium-based catalyst. In some embodiments, the chiral catalyst is an Iridium-based catalyst. Any Ruthenium-based or Iridium-based catalysts known in the art may be used, such as those described in Wang et al, Chem. Rev. 2015, 115, 6621-6686. The Ruthenium-based catalyst may include, but is not limited to, RuCl(p-cymene)[Ts-DPEN], Teth-TsDpen RuCl, RuCl[FsDPEN](p-cymene), RuCl[TsDPEN](mesitylene), RuCl[(p-cymene(BINAP)Cl, RuCl[(p-cymene(Tol-BINAP)Cl, RuCl[(p-cymene(DM-BINAP)Cl, RuCl[(p-cymene(H8-BINAP)Cl, RuCl[(p-cymene(SEGPHOS®)Cl (Chloro[5,5'-bis[di(3,5-xylyl)phosphino]-4,4'-bi-1,3-benzodioxole] (p-cymene)ruthenium(II) chloride), RuCl[(p-cymene(DM-SEGPHOS®)Cl (Chloro[(5,5'-bis[di(3,5-xylyl)phosphino]-4,4'-bi-1,3-benzodioxole](p-cymene)ruthenium(II) chloride), RuCl[(p-cymene(DTBM-SEGPHOS®)Cl (Chloro[(R)-(−) 5,5'-bis[bis(3,5-di-tert-butyl-4-methoxyphenyl)phosphino]-4,4'-bi-1,3-ben zodioxole](p-cymene)ruthenium(II) chloride). Other chiral catalysts known in the art may be used, including but not limited to Corey-Bakshi-Shibata catalyst. Another non-limiting example of a chiral catalyst that may be used is a chiral reagent such as B-Chlorodiisopinocampheylborane. In some embodiments, the chiral catalyst is a catalyst as described below for step (c) of Scheme 3.

Also provided herein are methods for preparing a compound of formula (C):

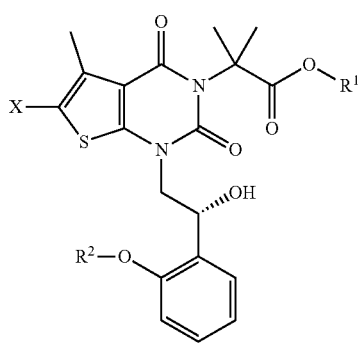

(C)

comprising the steps of:
(a) contacting a compound of formula (A):

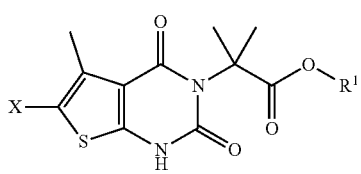

(A)

with a compound of formula (G):

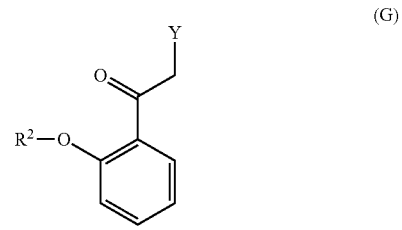

(G)

under conditions sufficient to form a compound of formula (B):

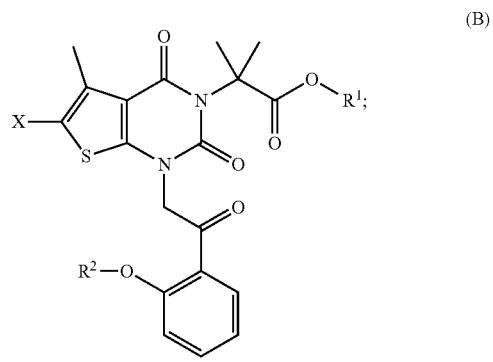

(B)

(b) hydrogenating a compound of formula (B) in the presence of a chiral catalyst under conditions sufficient to form a compound of formula (C);

wherein X is halo;

Y is a leaving group;

$R^1$ is $C_{1-6}$ alkyl or aryl; and $R^2$ is $C_{1-3}$ alkyl.

In some embodiments, X is halo; Y is a leaving group; $R^1$ is $C_{1-6}$ alkyl, $C_{1-2}$-alkylene-aryl, or aryl; and $R^2$ is $C_{1-3}$ alkyl.

In one embodiment, the present disclosure provides for a method for preparing a compound of formula (I):

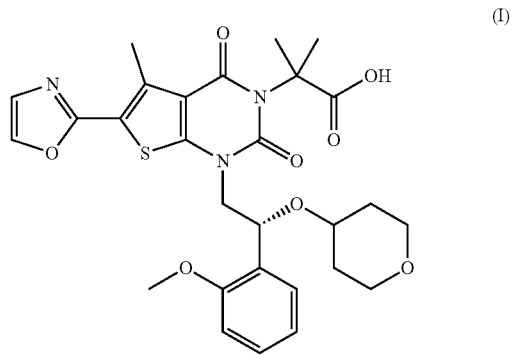 [SMILES: COc1ccccc1[C@H](Cn1c(=O)n(C(C)(C)C(=O)O)c(=O)c2c(C)c(-c3ncco3)sc21)OC1CCOCC1]

(I)

or a salt, a co-crystal, a solvate, or a hydrate thereof, comprising the steps of:

(a-1) contacting a compound of formula (A-1):

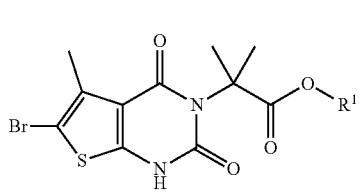
(A-1)

with a compound of formula (G-1):

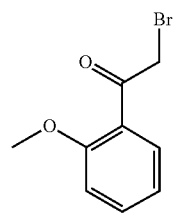
(G-1)

under conditions sufficient to form a compound of formula (B-1):

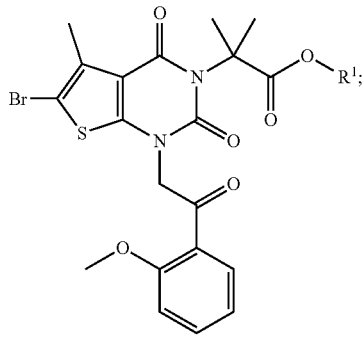
(B-1)

(b-1) hydrogenating a compound of formula (B-1) in the presence of a chiral catalyst under conditions sufficient to form a compound of formula (C-1):

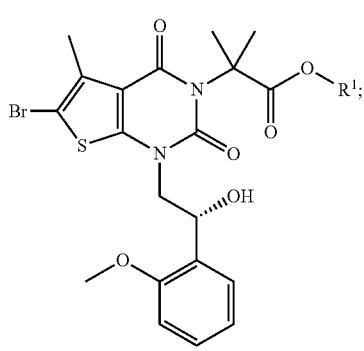
(C-1)

(c-1) contacting a compound of formula (C-1) with a compound of formula (H-1):

(H-1)

under conditions sufficient to form a compound of formula (D-1):

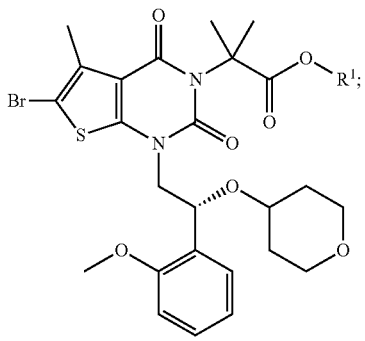
(D-1)

(d-1) contacting a compound of formula (D-1) with oxazole under conditions sufficient to form a compound of formula (E-1):

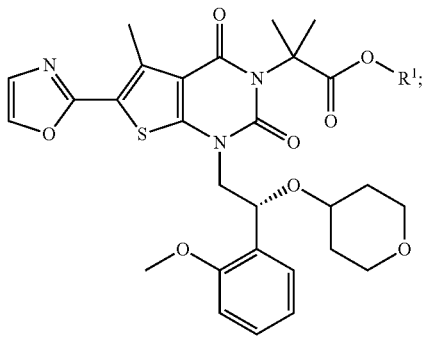
(E-1)

(e-1) hydrolyzing a compound of formula (E-1) under conditions sufficient to form a compound of formula (I);

wherein when ═ is a single bond, W is halo, mesylate, tosylate, or trichloroacetimidate, or when ═ is a double bond, W is O; and $R^1$ is $C_{1-6}$ alkyl, $C_{1-2}$-alkylene-aryl, or aryl.

Scheme 2 represents an exemplary synthesis of a compound of formula (I), or a salt, a co-crystal, a solvate, or a hydrate thereof, and may be carried out according to the embodiments described herein.

Scheme 2

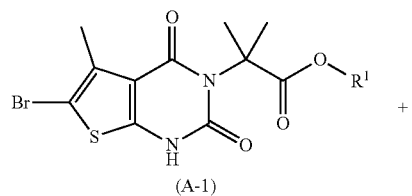

(A-1) +

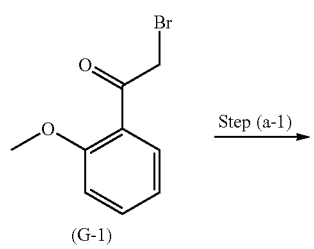

(G-1)

Step (a-1) →

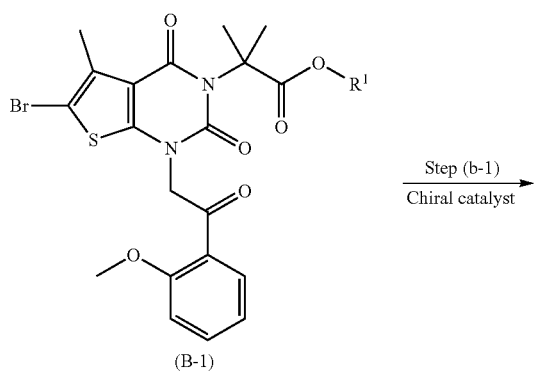

(B-1)

Step (b-1)
Chiral catalyst →

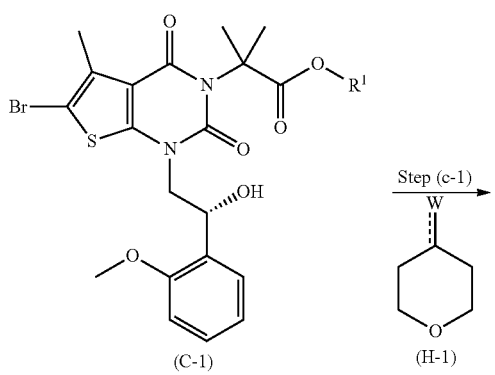

(C-1)

Step (c-1)
W
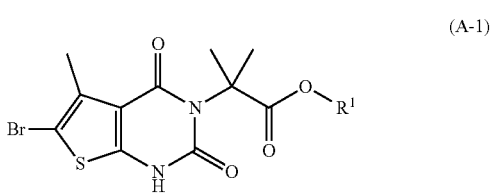
(H-1) →

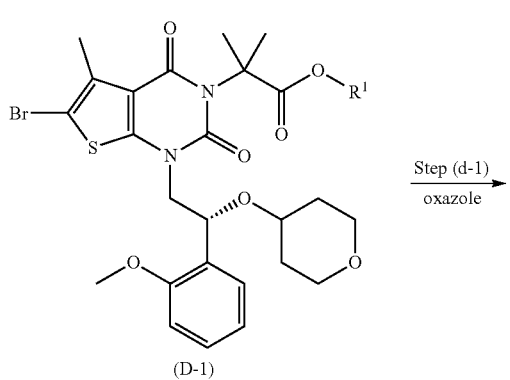

(D-1)

Step (d-1)
oxazole →

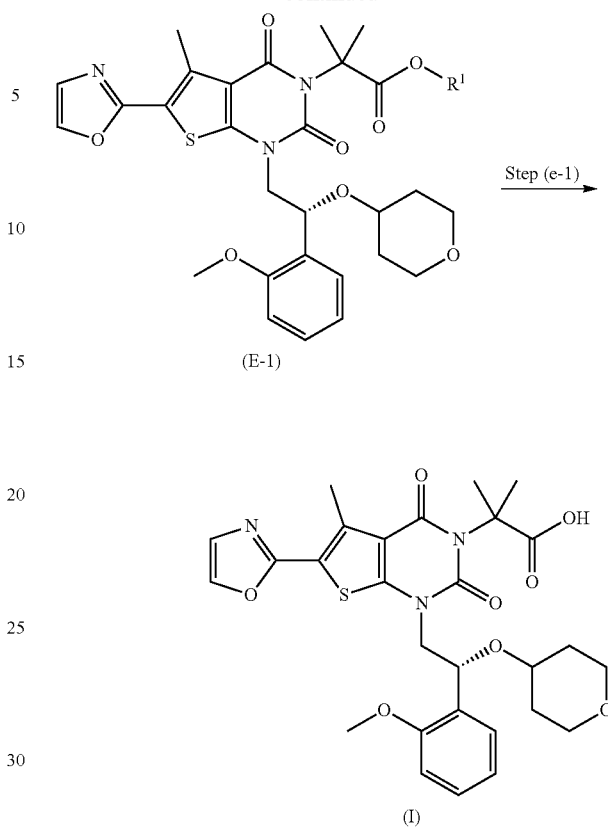

(E-1)

Step (e-1) →

(I)

In some embodiments provided herein, $R^1$ is $C_{1-6}$ alkyl or aryl, and when ═ is a single bond, W is a leaving group, or when ═ is a double bond, W is O. In some embodiments provided herein, $R^1$ is $C_{1-6}$ alkyl, $C_{1-2}$-alkylene-aryl, or aryl, and when ═ is a single bond, W is a leaving group, or when ═ is a double bond, W is O.

In some embodiments, step (a-1) comprises contacting a compound of formula (A-1):

(A-1)

with a compound of formula (G-1):

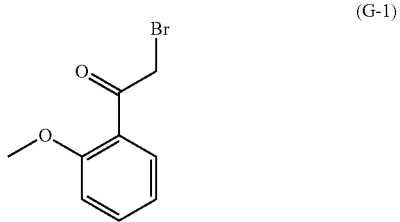

(G-1)

under conditions sufficient to form a compound of formula (B-1):

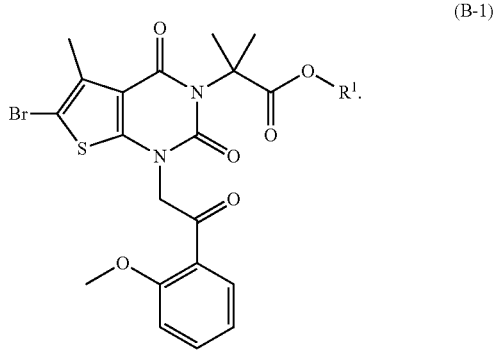

(B-1)

In some embodiments, step (b-1) comprises hydrogenating a compound of formula (B-1) in the presence of a chiral catalyst under conditions sufficient to form a compound of formula (C-1):

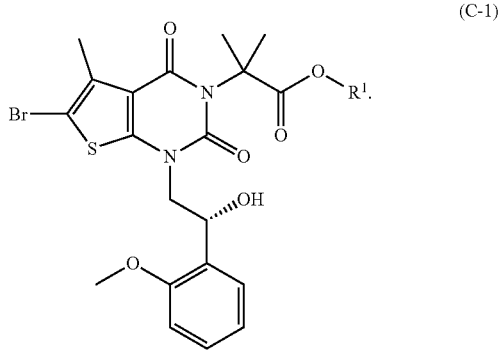

(C-1)

In some embodiments, step (c-1) comprises contacting a compound of formula (C-1) with a compound of formula (H-1):

(H-1)

under conditions sufficient to form a compound of formula (D-1):

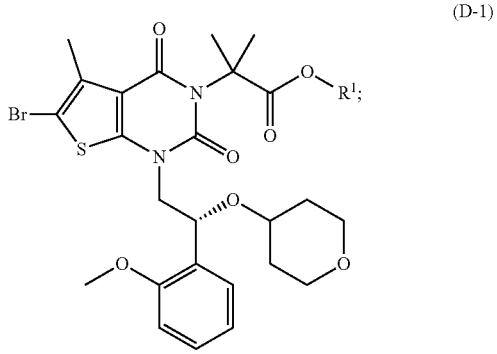

(D-1)

wherein when ═ is a single bond, W is halo, mesylate, tosylate, or trichloroacetimidate, or when ═ is a double bond, W is O.

In some embodiments, step (d-1) comprises contacting a compound of formula (D-1) with oxazole under conditions sufficient to form a compound of formula (E-1):

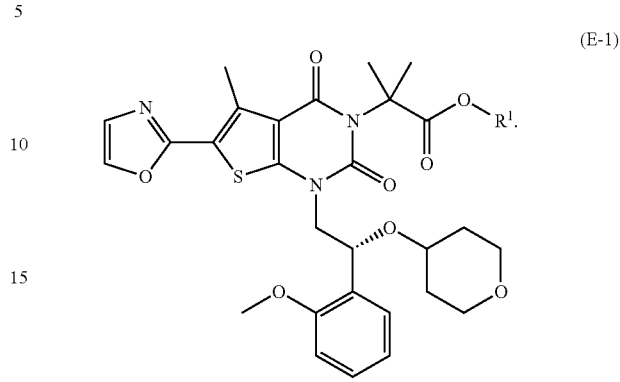

(E-1)

In some embodiments, step (e-1) comprises hydrolyzing a compound of formula (E-1) under conditions sufficient to form a compound of formula (I).

In some embodiments provided herein, $R^1$ is $C_{1-6}$ alkyl or aryl. In some embodiments provided herein, $R^1$ is $C_{1-6}$ alkyl, $C_{1-2}$-alkylene-aryl, or aryl. In some embodiments, $R^1$ is benzyl or tert-butyl.

In some embodiments, $R^1$ is $C_{1-6}$ alkyl. In some embodiments, $R^1$ is methyl. In some embodiments, $R^1$ is ethyl. In some embodiments, $R^1$ is propyl. In some embodiments, $R^1$ is tert-butyl.

In some embodiments, $R^1$ is $C_{6-10}$ aryl. In some embodiments, $R^1$ is $C_{1-2}$-alkylene-aryl. In some embodiments, $R^1$ is benzyl.

In some embodiments, when ═ is a single bond, W is a leaving group. In some embodiments, when ═ is a single bond, W is halo. In some embodiments, when ═ is a single bond, W is Cl. In some embodiments, when ═ is a single bond, W is Br. In some embodiments, when ═ is a single bond, W is I. In some embodiments, when ═ is a single bond, W is mesylate or tosylate. In some embodiments, W is trichloroacetimidate. In some embodiments, when ═ is a double bond, W is O.

In some embodiments, the method provides for a compound of formula (I), or a salt or a co-crystal thereof. In some embodiments, the method provides for a compound of formula (I), or a pharmaceutically acceptable salt thereof. In some embodiments, the method provides for a compound of formula (I), or a pharmaceutically acceptable co-crystal thereof.

In some embodiments, compound of formula (C-1), compound of formula (D-1), compound of formula (E-1), or compound of formula (I) is present in an enantiomeric excess (e.e.) of about 90 to about 99.9 percent. In some embodiments, compound of formula (C-1), compound of formula (D-1), compound of formula (E-1), or compound of formula (I) is present in an enantiomeric excess (e.e.) of at least about 90, 91, 92, 93, 94, 95, 96, 97, 97.5, 98.0, 98.5, 99.0, 99.5, 99.7, 99.8, 99.9, or 99.95 percent. In some embodiments, compound of formula (I) is present in an enantiomeric excess (e.e.) of at least about 95, 96, 97, 97.5, 98.0, 98.5, 99.0, 99.5, 99.7, 99.8, 99.9, or 99.95 percent.

Compound of formula (A-1), compound of formula (B-1), and compound of formula (G-1) may be prepared as described, for example, in U.S. Pat. No. 8,969,557, or according to methods known in the art.

In some embodiments, the reaction conditions of step (a-1) comprise a base. In some embodiments, the base is a carbonate base. In some embodiments, the carbonate base is an alkali metal carbonate. In some embodiments, the base is sodium carbonate, sodium bicarbonate, potassium carbonate, potassium bicarbonate, cesium carbonate, cesium bicarbonate, potassium phosphate tribasic, or potassium phosphate dibasic. In some embodiments, the alkali metal carbonate is potassium carbonate or cesium carbonate. In some embodiments, the alkali metal carbonate is potassium carbonate. In some embodiments, the alkali metal carbonate is potassium bicarbonate. In some embodiments, the alkali metal carbonate is cesium carbonate. In some embodiments, the alkali metal carbonate is cesium bicarbonate. In some embodiments, the base is potassium phosphate tribasic or potassium phosphate dibasic. In some embodiments, the reaction conditions of step (a-1) proceeds in a polar solvent. In some embodiments, the polar solvent is a polar aprotic solvent. In some embodiments, the polar aprotic solvent is N-methylpyrrolidone (NMP). In some embodiments, the polar aprotic solvent is N,N-dimethylformamide (DMF). In some embodiments, the polar aprotic solvent is N,N-dimethylacetamide (DMA).

In some embodiments, the reaction conditions of step (b-1) comprise a hydrogen source. Suitable hydrogen sources/conditions are known in the art as described, for example, in Wang et al, Chem. Rev. 2015, 115, 6621-6686. In some embodiments, the reaction conditions of step (b-1) comprise $H_2$ and a catalyst including but not limited to those described in Xie et al., Synthesis 2015, 47, 460-471. In some embodiments, the reaction conditions of step (b-1) comprise formic acid. In some embodiments, the reaction conditions of step (b-1) comprise an organic amine. In some embodiments, the organic amine is triethylamine. In some embodiments, the reaction conditions of step (b-1) comprise formic acid and triethylamine, ammonium formate, or formic acid and sodium formate. In some embodiments, the reaction conditions of step (b-1) comprise formic acid and trimethylamine. In some embodiments, the reaction conditions of step (b-1) comprise formic acid and triethylamine. In some embodiments, In some embodiments, the reaction conditions of step (b-1) comprise a base. In some embodiments, the base is a t-butoxide. In some embodiments, the base is sodium t-butoxide or potassium t-butoxide. In some embodiments, when a base is present, the solvent is a polar solvent. The solvent may include, but is not limited to, isopropanol.

In some embodiments, the chiral catalyst is a Ruthenium-based catalyst or an Iridium-based catalyst. In some embodiments, the chiral catalyst is a Ruthenium-based catalyst. In some embodiments, the chiral catalyst is an Iridium-based catalyst. Any Ruthenium-based or Iridium-based catalysts known in the art may be used, such as those described in Wang et al, Chem. Rev. 2015, 115, 6621-6686. The Ruthenium-based catalyst may include, but is not limited to, RuCl(p-cymene)[Ts-DPEN], Teth-TsDpen RuCl, RuCl[FsDPEN](p-cymene), RuCl[TsDPEN](mesitylene), RuCl[(p-cymene(BINAP)Cl, RuCl[(p-cymene(Tol-BINAP)Cl, RuCl[(p-cymene(DM-BINAP)Cl, RuCl[(p-cymene(H8-BINAP)Cl, RuCl[(p-cymene(SEGPHOS®)Cl (Chloro[5,5'-bis[di(3,5-xylyl)phosphino]-4,4'-bi-1,3-benzodioxole] (p-cymene)ruthenium(II) chloride), RuCl[(p-cymene(DM-SEGPHOS®)Cl (Chloro[(5,5'-bis[di(3,5-xylyl)phosphino]-4,4'-bi-1,3-benzodioxole](p-cymene)ruthenium(II) chloride), and RuCl[(p-cymene(DTBM-SEGPHOS®)Cl (Chloro[(R)-(−)5,5'-bis[bis(3,5-di-tert-butyl-4-methoxyphenyl)phosphino]-4,4'-bi-1,3-ben zodioxole](p-cymene)ruthenium(II) chloride). Other chiral catalysts known in the art may be used, including but not limited to Corey-Bakshi-Shibata catalyst. Another non-limiting example of a chiral catalyst that may be used is a chiral reagent such as B-Chlorodiisopinocampheylborane. In some embodiments, the chiral catalyst is a catalyst as described below for step (c) of Scheme 3.

In some embodiments, the reaction conditions of step (c-1) comprise a base. In some embodiments, the base is an organic base. In some embodiments, the organic base is a Lewis base. In some embodiments, the organic base is 1,8-diazabicyclo[5.4.0]undec-7-ene or Barton's base.

In some embodiments, wherein W is trichloroacetimidate or O, the reaction conditions of step (c) comprise a Lewis or Bronsted acid.

In some embodiments, the reaction conditions of step (d-1) comprise a coupling of compound of formula (D-1) with an oxazole synthon (oxazole or oxazole metalate), thereby forming compound of formula (E-1). In some embodiments, the coupling is a metal-catalyzed coupling. In some embodiments, the metal-catalyzed coupling is a Negishi coupling. One of skill in the art will appreciate that a Negishi coupling is a transition metal-catalyzed cross-coupling of an organic halide or sulfonate compound with an organozinc compound. In some embodiments, the oxazole synthon is an oxazole zincate. In some embodiments, the oxazole zincate is formed by metal exchange between 2-lithio-oxazole and a zinc salt. In some embodiments the zinc salt is $ZnCl_2$. In some embodiments, the 2-lithio-oxazole is formed by treating oxazole with n-butyllithium. In some embodiments, the 2-lithio-oxazole is formed at a temperature below −40° C. In some embodiments, the 2-lithio-oxazole is formed at a temperature below about −40° C. In some embodiments, the 2-lithio-oxazole is formed at a temperature below −60° C. In some embodiments, the 2-lithio-oxazole is formed at a temperature below about −60° C. In some embodiments, the metal catalyst is a palladium catalyst. In some embodiments, the palladium catalyst is $Pd(PPh_3)_4$. In some embodiments, compound of formula (E-1) is purified by crystallization.

In some embodiments, the reaction conditions of step (d-1) comprise a metalating agent. In some embodiments, the oxazole is treated with a metalating agent selected from isopropyl magnesium chloride, isopropyl magnesium bromide, TMPZnCl—LiCl, TMPMgCl—LiCl, and isopropyl magnesium chloride/lithium chloride (wherein TMP refers to 2,2,6,6,-tetramethylpiperidine). In some embodiments, the metalating agent is isopropyl magnesium chloride. In some embodiments, the oxazole is treated with isopropyl magnesium chloride (2M in THF). In some embodiments, the oxazole is treated with a metalating agent at about −20° C. to about −10° C. In some embodiments, the oxazole is treated with a metalating agent at about −15° C. In some embodiments, the solvent is tetrahydrofuran, 2-methyltetrahydrofuran, or a mixture thereof. In some embodiments, the solvent is tetrahydrofuran and 2-methyltetrahydrofuran. In some embodiments, the reaction further comprises adding $ZnCl_2$ to form an oxazole zincate. In some embodiments, the reaction further comprises adding $ZnCl_2$ as a solution in 2-methyltetrahydrofuran. In some embodiments, the catalyst used in the Negishi coupling is a palladium catalyst. In some embodiments, the catalyst used in the Negishi coupling is a palladium catalyst selected from $Pd(PPh_3)_4$, tBuXPhos Pd precatalyst, XPhos Pd precatalyst, RuPhos Pd precatalyst, and Pd-PEPPSI-IPent (dichloro[1,3-bis(2,6-di-3-pentylphenyl)imidazol-2-ylidene](3-chloropyridyl)palladium(II)). Such precatalysts are described in, for example, Bruneau et al., ACS Catal., 2015, 5(2), pp. 1386-1396. In some embodiments, the catalyst is formed in situ via a suitable palladium source and appropriate chiral ligands according to methods known in the art. In some embodiments, the catalyst is Pd(PPh$_3$)$_4$. In some embodiments, the reaction mixture is heated to greater than about 50° C. after addition of ZnCl$_2$. In some embodiments, the reaction mixture is heated to about 65° C.

In some embodiments, the reaction conditions of step (e-1) comprise an acid. In some embodiments, the acid is sulfuric acid, tetrafluoroboric acid, methanesulfonic acid, nitric acid, or hydrochloric acid. In some embodiments, the acid is sulfuric acid. In some embodiments, the acid is hydrochloric acid.

In some embodiments, the reaction conditions of step (e-1) comprise a co-solvent. In some embodiments, the co-solvent is an alcohol. In some embodiments, the co-solvent is 2-propanol, t-butanol, t-amyl alcohol, ethanol, or acetonitrile.

In some embodiments, the reaction conditions of step (e-1) comprise a temperature of about 5 and 10° C. In some embodiments, the reaction conditions of step (e-1) comprise a temperature between about 0 and about 20° C. In some embodiments, the reaction conditions of step (e-1) comprise between about 2 and about 8° C.

Alternative reaction conditions, such as steps (a-1), (d-1), or (e-1), may be performed as described, for example, in U.S. Pat. No. 8,969,557.

Also provided herein are methods of preparing intermediates useful for methods of making a compound of formula (I) as described in, for example, U.S. Pat. No. 8,969,557 and U.S. Patent Publication No. 2017/0267690.

In one embodiment, the present disclosure provides for a method for preparing compound of formula (J):

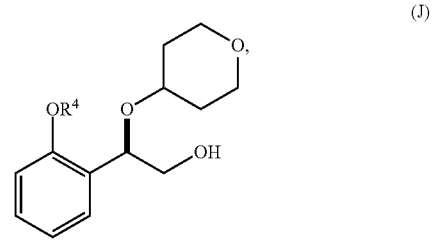

wherein R$^4$ is C$_{1-3}$ alkyl.

Scheme 3 represents an exemplary synthesis of a compound of formula (J) and may be carried out according to the embodiments described herein.

Scheme 3

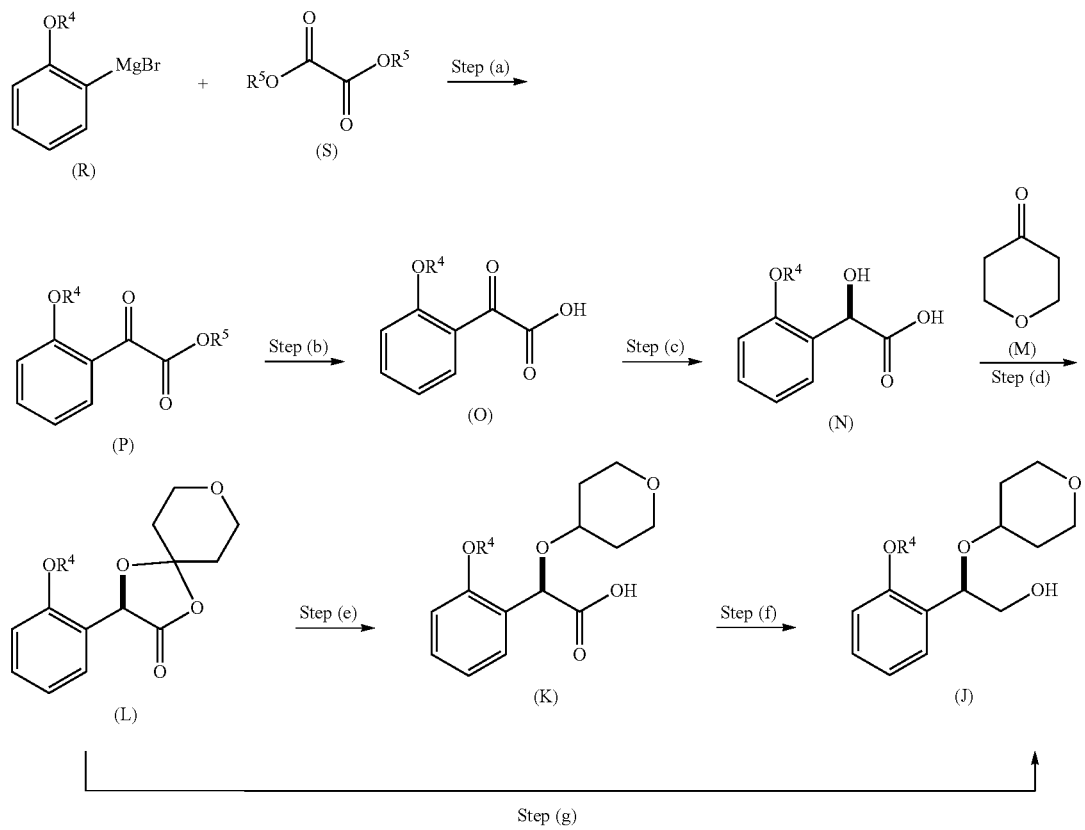

In some embodiments, R$^4$ is methyl or ethyl. In some embodiments, R$^4$ is methyl. In some embodiments, R$^4$ is ethyl. In some embodiments, R$^4$ is propyl.

In any of the embodiments described herein, R$^4$ is an optionally substituted C$_{1-3}$ alkyl. In some embodiments, R$^4$ is a C$_{1-3}$ alkyl optionally substituted with halogen. In any of the embodiments described herein, a compound of formula (M) may be exchanged with a compound of formula R$^{20}$C(O)R$^{21}$, wherein each of R$^{20}$ and R$^{21}$ are independently optionally substituted alkyl, or $R^{20}$ and $R^{21}$ together with the carbon to which they are attached form a $C_{3-6}$ cycloalkyl or 5 to 6-membered heterocycloalkyl ring. In such embodiments, corresponding analogs of compounds of formula (L), (K), and (J) may be achieved.

In some embodiments, each $R^5$ is independently an optionally substituted $C_{1-6}$ alkyl or an optionally substituted $C_{1-6}$ aryl. In some embodiments, each $R^5$ is independently an optionally substituted $C_{1-6}$ alkyl. In some embodiments, each $R^5$ is independently an optionally substituted $C_{1-6}$ aryl. In some embodiments, each $R^5$ is independently $C_{1-3}$ alkyl. In some embodiments, each $R^5$ is independently methyl. In some embodiments, each $R^5$ is independently ethyl. In some embodiments, each $R^5$ is independently propyl.

In some embodiments, a method for preparing compound of formula (J) comprises the steps of:

(a) contacting a compound of formula (R):

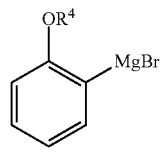

(R)

with a compound of formula (S):

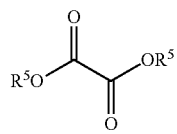

(S)

under conditions sufficient to form a compound of formula (P):

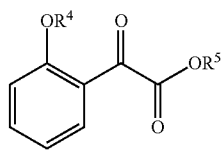

(P)

or a solvate or a hydrate thereof, (b) contacting a compound of formula (P), or a solvate or a hydrate thereof, with a base under conditions sufficient to form a compound of formula (O):

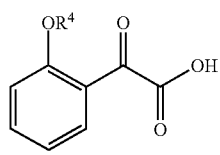

(O)

or a salt, a solvate, or a hydrate thereof, (c) contacting a compound of formula (O), or a salt, a solvate, or a hydrate thereof, with a reductant and a catalyst under conditions sufficient to form a compound of formula (N):

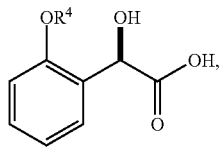

(N)

(d) contacting a compound of formula (N) with a compound of formula (M):

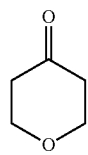

(M)

under conditions sufficient to form a compound of formula (L):

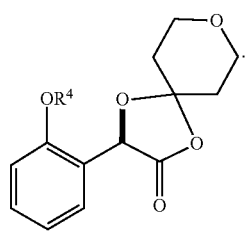

(L)

In some embodiments, the method for preparing compound of formula (J) further comprises:

(e) contacting a compound of formula (L) with a reductant under conditions sufficient to form a compound of formula (K):

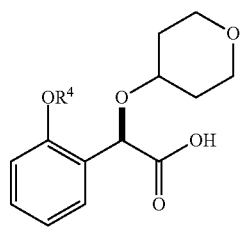

(K)

and (f) contacting a compound of formula (K) with a reductant under conditions sufficient to form a compound of formula (J).

In some embodiments, the method for preparing compound of formula (J) further comprises:

(g) contacting a compound of formula (L) with a reductant under conditions sufficient to form a compound of formula (J).

In some embodiments, a compound of formula (R) is prepared according to Grignard conditions known in the art, such as described in Alorati et al., Organic Process Research and Development, 2012, 16(12), pp. 1947-1952.

In some embodiments, the reaction conditions of step (a) of Scheme 3 comprise a solvent, wherein the solvent is THF, 2-methyltetrahydrofuran, diethyl ether, diisopropyl ether, dibutyl ether, THF/toluene, methyl tert-butyl ether, cyclopentyl methyl ether, or dimethyl ether. In some embodiments, the solvent is THF. In some embodiments, the reaction conditions of step (a) of Scheme 3 comprise a temperature of about −40 and about 0° C. In some embodiments, the reaction conditions of step (a) of Scheme 3 comprise a temperature of about −20° C.

In some embodiments, step (b) of Scheme 3 further comprises forming a salt of a compound of formula (O).

In some embodiments, step (b) of Scheme 3 comprises a hydrolysis step to form a compound of formula (O), and optionally followed by a salt conversion to form a salt of a compound of formula (O). In some embodiments, the hydrolysis and salt conversion may be performed simultaneously (for example, as a one-pot synthesis). In some embodiments, the reaction conditions of the hydrolysis step of step (b) comprise a base. In some embodiments, the base is KOH, NaOH, LiOH, CsOH, $K_3PO_4$, $K_2CO_3$, $Na_2CO_3$, $Li_2CO_3$, or $Cs_2CO_3$. In some embodiments, the base is NaOH. In some embodiments, the base is KOH. In some embodiments, the reaction conditions of the hydrolysis step of step (b) comprise a solvent, wherein the solvent is THF, methanol, ethanol, isopropyl alcohol, dimethyl ether, cyclopentyl methyl ether, dioxane, 2-methyltetrahydrofuran, methyl tert-butyl ether, water, or mixtures thereof. In some embodiments, the solvent is THF. In some embodiments, the solvent is a mixture of ethanol and THF. In some embodiments, the reaction conditions of the hydrolysis step of step (b) comprise a temperature of about −15 and about 40° C. In some embodiments, the reaction conditions of the hydrolysis step of step (b) comprise a temperature of about 0° C. In some embodiments, the reaction conditions of the hydrolysis step of step (b) comprise, after the addition of the base, an acid. In some embodiments, the acid is HCl, $H_2SO_4$, or citric acid. In some embodiments, the acid is HCl.

In some embodiments, the reaction conditions of the salt conversion of step (b) comprise a base. In some embodiments, the base is potassium tert-butoxide, KOH, $K_3PO_4$, $K_2CO_3$, KHMDS, KOEt, KOMe, KH, or $KHCO_3$. In some embodiments, the base is potassium tert-butoxide. In some embodiments, the reaction conditions of the salt conversion of step (b) comprise a solvent, wherein the solvent is ethyl acetate, isopropyl acetate, THF, acetonitrile, isopropyl alcohol, 2-methyltetrahydrofuran, cyclopentyl methyl ether, methyl tert-butyl ether, acetone, dichlormethane, 2-butanol, water, or mixtures thereof. In some embodiments, the solvent is ethyl acetate.

In some embodiments, the reaction conditions of step (c) of Scheme 3 comprise a reductant. In some embodiments, the reductant is formic acid and triethyl amine or isopropyl alcohol and potassium hydroxide. In some embodiments, the reductant is formic acid and triethyl amine. In some embodiments, the reaction conditions of step (c) of Scheme 3 comprise a catalyst. In some embodiments, the catalyst is (R,R)-Ts-DENEB (chloro{N-[(1R,2R)-1,2-diphenyl-2-(2-(4-methylbenzyloxy)ethylamino)-ethyl]-4-methylbenzene sulfonamide(chloro)ruthenium(II)); TsDPEN (N-(4-toluenesulfonyl)-1,2-diphenylethylenediamine), DPEN (1,2-diphenylethylenediamine), or TosNapEN (N-(4-toluenesulfonyl)-1,2-di(1-naphthyl)ethylenediamine), with $[RuCl_2(p-CYM)]_2$; DPEN (1,2-diphenylethylenediamine), DNEN-HCl (1,2-dinaphthalen-1-ylethane-1,2-diamine, dihydrochloride), DPEN(Me) (N,N'-dimethyl-1,2-diphenyl-1,2-ethylenediamine), DMeODPEN-HCl (1,2-bis(4-methoxyphenyl) ethane-1,2-diamine dihydrochloride), or DOHDPEN (2,2'-(1,2-diaminoethane-1,2-diyl)diphenol) with $[RhCl_2(Cp)]_2$; or TsDPEN, DPEN, DNEN-HCl, DMesEN-HCl (1,2-bis(2,4,6-trimethylphenyl)-1,2-ethanediamine, dihydrochloride), TosNapEN, TsDMesEN (N-[2-amino-1,2-bis(2,4,6-trimethylphenyl)ethyl]-4-methylbenzenesulfonamide), or DOH-DPEN with $[IrCl_2(Cp)]_2$. The ligands described herein may be referred to by other names known in the art, and the appropriate chirality of ligand may be chosen to achieve the appropriate chiral product. In some embodiments, the catalyst is (R,R)-Ts-DENEB.

In some embodiments, the reaction conditions of step (c) of Scheme 3 comprise $H_2$ and a catalyst including but not limited to those described in Xie et al., Synthesis 2015, 47, 460-471. In some embodiments, the reaction conditions of step (c) of Scheme 3 comprises a solvent, wherein the solvent is dimethyl formamide or isopropyl alcohol. In some embodiments, the reaction conditions of step (c) of Scheme 3 comprise a temperature of about 20° C. about 80° C. In some embodiments, the reaction conditions of step (c) of Scheme 3 comprise a temperature of about 50° C.

In some embodiments, the reaction conditions of step (d) of Scheme 3 comprise a Lewis acid. In some embodiments, the Lewis acid is $BF_3$-THF, $BF_3$-$Et_2O$ and other analogous stabilized $BF_3$ reagents, Scandium(III) triflate, and other lanthanide metal triflates, triflic acid, camphorsulfonic acid, p-toluenesulfonic acid, or pyridinium p-toluenesulphonate. In some embodiments, the Lewis acid is $BF_3$-THF. In some embodiments, the reaction conditions of step (d) of Scheme 3 comprise a solvent selected from methyl tert-butyl ether, 2-methyltetrahydrofuran, diethyl ether, diisopropyl ether, dibutyl ether, dioxane, dimethyl ether, methyl tert-butyl ether ("MTBE"), cyclopentyl methyl ether, THF, toluene, or dichloromethane. In some embodiments, the solvent is MTBE. In some embodiments, the reaction conditions of step (d) of Scheme 3 comprise a temperature of about −20° C. about 45° C. In some embodiments, the reaction conditions of step (d) of Scheme 3 comprise a temperature of about 0° C.

In some embodiments, the reaction conditions of step (e) of Scheme 3 comprise a reductant. In some embodiments, the reductant is tert-butylmagnesium chloride (t-BuMgCl), triethylsilane, triisopropylsilane, tripropylsilane, triphenylsilane, triisobutylsilane, TMDS (1,1,3,3-tetramethyldisiloxane), or sodium borohydride. In some embodiments, the reductant is tert-butylmagnesium chloride. In some embodiments, the reaction conditions of step (e) of Scheme 3 further comprise a Lewis acid. In some embodiments, the Lewis acid is $BF_3$-THF, $BF_3$-$Et_2O$, $ZrCl_4$, $TiCl_4$, t-BuMgCl with LiCl, or t-BuMgCl with $TiCl_4$. In some embodiments, the reaction conditions of step (e) of Scheme 3 comprise a solvent selected from THF, 2-methyltetrahydrofuran ("MeTHF"), diglyme, dimethyl ether, diethyl ether, diisopropyl ether, dibutyl ether, DCM, MTBE, toluene, dioxane, cyclopentyl methyl ether, and mixtures thereof. In some embodiments, the solvent is a mixture of DCM and MeTHF; DCM, MTBE, and MeTHF; or dibutylether, DCM, and MeTHF. In some embodiments, the solvent is a mixture of DCM and MeTHF. In some embodiments, the solvent is MeTHF. In some embodiments, the reaction conditions of step (e) of Scheme 3 comprise a temperature of about −70° C. about 30° C. In some embodiments, the reaction conditions of step (e) of Scheme 3 comprise a temperature of about 10° C.

In some embodiments, the reaction conditions of step (f) of Scheme 3 comprise a reductant. In some embodiments, the reductant is $BF_3$-THF/$NaBH_4$, $BF_3$-$Et_2O$/$NaBH_4$, lithium aluminum hydride, borane dimethyl sulfide complex, $BH_3$-THF, or other analogous stabilized $BH_3$ reagents.

In some embodiments, the reductant is BF$_3$-THF/NaBH$_4$. In some embodiments, the reaction conditions of step (f) of Scheme 3 comprise a solvent selected from THF, MeTHF, cyclopentyl methyl ether, MTBE, dioxane, dimethyl ether, diethyl ether, diisopropyl ether, dibutyl ether, toluene, and mixtures thereof. In some embodiments, the solvent is THF. In some embodiments, the reaction conditions of step (f) of Scheme 3 comprise a temperature of about −20° C. about 30° C. In some embodiments, the reaction conditions of step (f) of Scheme 3 comprise a temperature of about 0° C. to about 20° C.

In some embodiments, the reaction conditions of step (g) of Scheme 3 comprise a reductant. In some embodiments, the reductant is BF$_3$-THF/NaBH$_4$ or BF$_3$-Et$_2$O/NaBH$_4$. In some embodiments, the reductant is BF$_3$-THF/NaBH$_4$. In some embodiments, the reaction conditions of step (f) of Scheme 3 comprise a Lewis acid. In some embodiments, the Lewis acid is BF$_3$-Et$_2$O. In some embodiments, the reaction conditions of step (g) of Scheme 3 comprise a solvent selected from diglyme, THF, MeTHF, dimethyl ether, dioxane, or other glyme solvents. In some embodiments, the solvent is diglyme. In some embodiments, the reaction conditions of step (g) of Scheme 3 comprise a temperature of about −10° C. about 40° C. In some embodiments, the reaction conditions of step (g) of Scheme 3 comprise a temperature of about 15° C. to about 30° C.

Some embodiments provided herein are directed to methods of preparing a compound of formula (L):

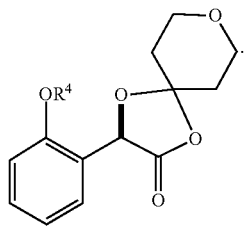

(L)

comprising contacting a compound of formula (N):

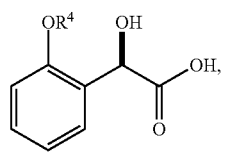

(N)

with a compound of formula (M):

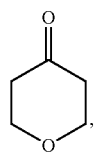

(M)

under conditions sufficient to form a compound of formula (L), and R$^4$ is as defined herein.

In some embodiments, the reaction conditions for preparing a compound of formula (L) comprise a Lewis acid. In some embodiments, the Lewis acid is BF$_3$-THF, BF$_3$-Et$_2$O and other analogous stabilized BF$_3$ reagents, Scandium(III) triflate, and other lanthanide metal triflates, triflic acid, camphorsulfonic acid, p-toluenesulfonic acid, or pyridinium p-toluenesulphonate. In some embodiments, the Lewis acid is BF$_3$-THF. In some embodiments, the reaction conditions comprise a solvent selected from methyl tert-butyl ether, 2-methyltetrahydrofuran, diethyl ether, diisopropyl ether, dibutyl ether, dioxane, dimethyl ether, MTBE, cyclopentyl methyl ether, THF, toluene, or dichloromethane. In some embodiments, the solvent is MTBE. In some embodiments, the reaction conditions comprise a temperature of about −20° C. about 45° C. In some embodiments, the reaction conditions comprise a temperature of about 0° C.

Some embodiments provided herein are directed to methods of preparing a compound of formula (K):

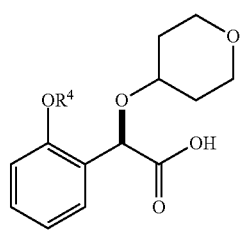

(K)

comprising contacting a compound of formula (L):

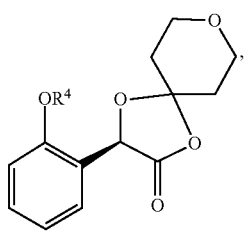

(L)

with a reductant under conditions sufficient to form a compound of formula (K), and R$^4$ is as defined herein.

In some embodiments, the reaction conditions for preparing a compound of formula (K) comprise a reductant. In some embodiments, the reductant is tert-butylmagnesium chloride (t-BuMgCl), triethylsilane, triisopropylsilane, tripropylsilane, triphenylsilane, triisobutylsilane, TMDS (1,1,3,3-tetramethyldisiloxane), or sodium borohydride. In some embodiments, the reductant is tert-butylmagnesium chloride. In some embodiments, the reaction conditions further comprise a Lewis acid. In some embodiments, the Lewis acid is BF$_3$-THF, BF$_3$-Et$_2$O, ZrCl$_4$, TiCl$_4$, t-BuMgCl with LiCl, or t-BuMgCl with TiCl$_4$. In some embodiments, the reaction conditions comprise a solvent selected from THF, MeTHF, diglyme, dimethyl ether, diethyl ether, diisopropyl ether, dibutyl ether, DCM, MTBE, toluene, dioxane, cyclopentyl methyl ether, and mixtures thereof. In some embodiments, the solvent is a mixture of DCM and MeTHF; DCM, MTBE, and MeTHF; or dibutylether, DCM, and MeTHF. In some embodiments, the solvent is a mixture of DCM and MeTHF. In some embodiments, the solvent is MeTHF. In some embodiments, the reaction conditions comprise a temperature of about −70° C. about 30° C. In some embodiments, the reaction conditions comprise a temperature of about 10° C.

In one embodiment, the present disclosure provides for a method for preparing a compound of formula (N):

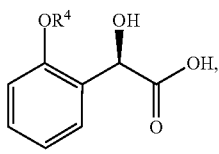

(N)

wherein $R^4$ is $C_{1-3}$ alkyl.

In some embodiments, $R^4$ is methyl or ethyl. In some embodiments, $R^4$ is methyl. In some embodiments, $R^4$ is ethyl. In some embodiments, $R^4$ is propyl.

Scheme 4 represents an exemplary, alternative synthesis of a compound of formula (N) and may be carried out according to the embodiments described herein.

Scheme 4

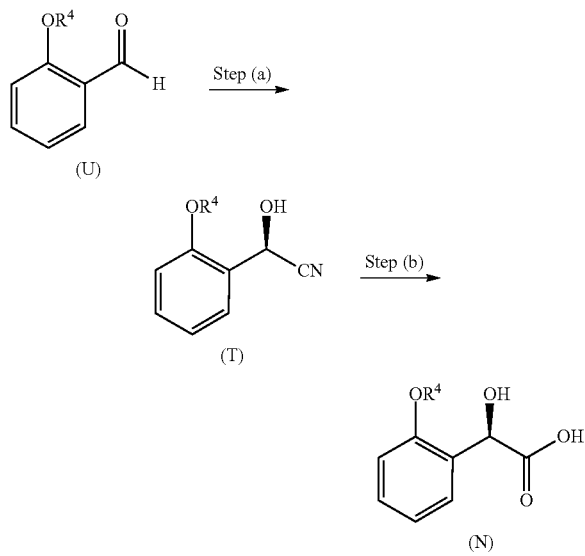

Some embodiments provide for a method for preparing a compound of formula (N) comprising:

(a) contacting a compound of formula (U):

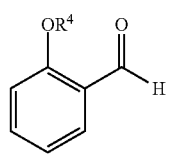

(U)

with a hydroxynitrilase and a hydrogen cyanide source under conditions sufficient to form a compound of formula (T):

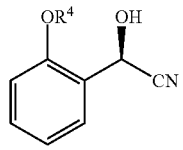

(T)

and (b) contacting a compound of formula (T) with a nitrilase under conditions sufficient to form a compound of formula (N), wherein $R^4$ is $C_{1-3}$ alkyl.

In some embodiments, the reaction conditions of step (a) of Scheme 4 comprise a hydroxynitrilase. In some embodiments, the hydroxynitrilase (also known as oxynitrilase, hydroxynitrile lyase, acetone cyanohydrin lyase) has an enzyme classification number of 4.1.2.X, wherein X includes, but is not limited to 10, 11, 37, 39, 46 and 47. A range of preparations of the enzyme may be used, which includes but is not limited to purified enzyme, crude cell lysate, clarified cell lysate, whole cell, cross-linked enzyme aggregate ("CLEA"), cross-linked enzyme crystal ("CLEC"), or immobilsed on solid support. In some embodiments, the hydroxynitrilase is from *Prunus amygdlus* (used as a CLEA). In some embodiments, the reaction conditions of step (a) of Scheme 4 comprise a hydrogen cyanide source. In some embodiments, the hydrogen cyanide source is acetone cyanohydrin, hydrogen cyanide, or potassium cyanide. In some embodiments, the hydrogen cyanide source is acetone cyanohydrin.

In some embodiments, the reaction conditions of step (a) of Scheme 4 comprise a solvent. In some embodiments, the solvent is a solvent that solubilizes the starting material. Non-limiting examples of the solvent include 2-methyl tetrahydrofuran, methyl tert-butyl ether, diethyl ether, dibutyl ether, and diisopropyl ether. In some embodiments, the solvent is methyl tert-butyl ether. In some embodiments, the solvent is used in combination with buffer. The buffer may be dependent upon the enzyme used and may be pH 1 to 12. In some embodiments, the buffer is maleate, phosphate, citrate, formate, succinate, acetate, propionate, piperazine, 2-(N-morpholino)ethanesulfonic acid ("MES"), ethanolamine, carbonate, β-Hydroxy-4-morpholinepropanesulfonic acid, 3-Morpholino-2-hydroxypropanesulfonic acid ("MOPSO"), imidazole, 4-(2-Hydroxyethyl)piperazine-1-ethanesulfonic acid ("HEPES"), N,N-bis-(2-Hydroxyethyl)-2-aminoethanesulfonic Acid ("BES"), 2-[(2-Hydroxy-1,1-bis(hydroxymethyl)ethyl)amino]ethanesulfonic acid ("TES"), 3-(N-Morpholino)propanesulfonic acid ("MOPS"), 4-(N-Morpholino)butanesulfonic acid ("MOBS"), 2-Hydroxy-3-[tris(hydroxymethyl)methylamino]-1-propanesulfonic acid ("TAPSO"), triethanolamine, pyrophosphate, 4-(2-Hydroxyethyl)piperazine-1-(2-hydroxypropanesulfonic acid) ("HEPPSO"), Piperazine-N,N'-bis(2-hydroxypropanesulfonic acid) ("POPSO"), 2-Amino-2-(hydroxymethyl)-1,3-propanediol (TRIS, Trizma™), 4-(2-Hydroxyethyl)-1-piperazinepropanesulfonic acid ("HEPPS"), N-(2-Hydroxyethyl)piperazine-N'-(4-butanesulfonic acid) ("HEPBS"), N-[Tris(hydroxymethyl)methyl]-3-aminopropanesulfonic acid ("TAPS"), 2-Amino-2-methyl-1,3-propanediol ("AMPD"), N-tris(Hydroxymethyl)methyl-4-aminobutanesulfonic acid ("TABS"), 3-([1,1-Dimethyl-2-hydroxyethyl]amino)-2-hydroxypropanesulfonic acid ("AMPSO"), taurine, borate, N-Cyclohexyl-2-aminoethanesulfonic acid ("CHES"), ammonium hydroxide, methylamine, piperidine, 3-(Cyclohexylamino)-1-propanesulfonic acid ("CAPS"), or 4-(Cyclohexylamino)-1-butanesulfonic acid ("CABS"). In some embodiments, the buffer is sodium acetate. In some embodiments, the buffer is 0.4M sodium acetate (pH 5). In some embodiments, the reaction conditions of step (a) of Scheme 4 comprise a temperature up to about 80° C. and may depend on the thermostability of the enzyme and solvent used. In some embodiments, the reaction conditions comprise ambient temperature.

In some embodiments, the reaction conditions of step (b) of Scheme 4 comprise a nitrilase. In some embodiments, the nitrilase has an enzyme classification number: 3.5.5.X, wherein X includes, but is not limited to 1, 4, 5 and 7. A range of preparations of the enzyme may be used, which includes but is not limited to purified enzyme, crude cell lysate, clarified cell lysate, whole cell, CLEA, CLEC, or immobilized on solid support. In some embodiments, the nitrilase is Nitrilase from Codexis Nitrilase kit. In some embodiments, the reaction conditions of step (b) of Scheme 4 comprise a solvent. In some embodiments, the solvent is a solvent that solubilizes the starting material. Non-limiting examples of the solvent include dimethyl sulfoxide, N,N-dimethyl formamide, N,N-dimethyl acetamide, N-methyl pyrrolidinone, isopropanol, ethanol, methanol, methyl tert-butyl ether, and tetrahydrofuran. In some embodiments, the solvent is dimethyl sulfoxide. In some embodiments, the solvent is used in combination with buffer. The buffer may be dependent upon the enzyme used and may be pH 1 to 12. In some embodiments, the buffer is maleate, phosphate, citrate, formate, succinate, acetate, propionate, piperazine, MES, ethanolamine, carbonate, MOPSO, imidazole, HEPES, BES, TES, MOPS, MOBS, TAPSO, triethanolamine, pyrophosphate, HEPPSO, POPSO, Trizma, HEPPS, HEPBS, TAPS, AMPD, TABS, AMPSO, taurine, borate, CHES, ammonium hydroxide, methylamine, piperidine, CAPS and CABS. In some embodiments, the buffer is potassium phosphate. In some embodiments, the buffer is 0.1M potassium phosphate (pH 7). In some embodiments, the reaction conditions of step (b) of Scheme 4 comprise a temperature up to about 80° C. and may depend on the thermostability of the enzyme and solvent used. In some embodiments, the reaction conditions comprise ambient temperature.

Scheme 5 represents an exemplary, alternative synthesis of a compound of formula (N) and may be carried out according to the embodiments described herein.

Scheme 5

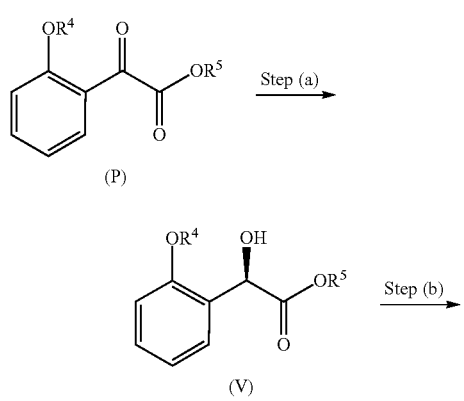

-continued

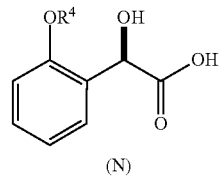

(N)

Some embodiments provide for a method for preparing a compound of formula (N) comprising:
(a) contacting a compound of formula (P):

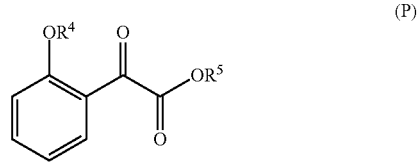

or a solvate or a hydrate thereof,
with a ketoreductase under conditions sufficient to form a compound of formula (V):

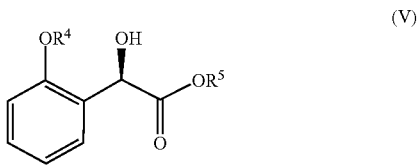

and (b) contacting a compound of formula (V) with a base under conditions sufficient to form a compound of formula (N),
wherein $R^4$ is $C_{1-3}$ alkyl and $R^5$ is an optionally substituted $C_{1-6}$ alkyl or an optionally substituted $C_{1-6}$ aryl.

In some embodiments, $R^4$ is methyl or ethyl. In some embodiments, $R^4$ is methyl. In some embodiments, $R^4$ is ethyl. In some embodiments, $R^4$ is propyl.

In some embodiments, $R^5$ is an optionally substituted $C_{1-6}$ alkyl or an optionally substituted $C_{1-6}$ aryl. In some embodiments, $R^5$ is an optionally substituted $C_{1-6}$ alkyl. In some embodiments, $R^5$ is an optionally substituted $C_{1-6}$ aryl. In some embodiments, $R^5$ is $C_{1-3}$ alkyl. In some embodiments, $R^5$ is methyl. In some embodiments, $R^5$ is ethyl. In some embodiments, $R^5$ is propyl.

In some embodiments, the reaction conditions of step (a) of Scheme 5 comprise a ketoreductase (also known as carbonylreductase or alcohol dehydrogenase). In some embodiments, the ketoreductase utilizes a nicotinamide co-factor ($NAD^+$, NADH, $NADP^+$, NADPH) as the reductant. In some embodiments, the ketoreductase may be any alternative oxidoreductase enzyme. A range of preparations of the enzyme may be used, which includes but is not limited to purified enzyme, crude cell lysate, clarified cell lysate, whole cell, CLEA, CLEC, or immobilized on solid support. In some embodiments, the ketoreductase is a ketoreductase (NADH or NADPH dependant) from Almac Cred Kit. In some embodiments, the ketoreductase is a ketoreductase (NADH or NADPH dependant) from Codexis Kred Kit. In some embodiments, the reaction conditions of step (a) of Scheme 5 comprise a co-factor recycling system. A variety of nicotinamide co-factor recycling systems may be used. A whole cell may be used as the co-factor recycling system with endogenous enzymes present; a substrate based recycling system may be used, for example, with isopropyl alcohol; or an enzyme based substrate recycling system may be used such as formate and formate dehydrogenase, phosphite and phosphite dehydrogenase, NADH oxidase or NADPH oxidase. Co-factor recycling enzymes may be co-expressed with the ketoreductase or expressed separately and added to the reaction mixture. In some embodiments, the co-factor recycling system is Glucose Dehydrogenase enzyme and glucose.

In some embodiments, the reaction conditions of step (a) of Scheme 5 comprise a solvent. In some embodiments, the solvent is a solvent that solubilizes the starting material. Non-limiting examples of the solvent include dimethyl sulfoxide, N,N-dimethyl formamide, N,N-dimethyl acetamide, N-methyl pyrrolidinone, isopropanol, ethanol, methanol, methyl tert-butyl ether, or tetrahydrofuran. In some embodiments, the solvent is dimethyl sulfoxide. In some embodiments, the solvent is used in combination with buffer. The buffer may be dependent upon the enzyme used and may be pH 1 to 12. In some embodiments, the buffer is maleate, phosphate, citrate, formate, succinate, acetate, propionate, piperazine, MES, ethanolamine, carbonate, MOPSO, imidazole, HEPES, BES, TES, MOPS, MOBS, TAPSO, triethanolamine, pyrophosphate, HEPPSO, POPSO, Trizma, HEPPS, HEPBS, TAPS, AMPD, TABS, AMPSO, taurine, borate, CHES, ammonium hydroxide, methylamine, piperidine, CAPS and CABS. In some embodiments, the buffer is potassium phosphate (pH 7). In some embodiments, the reaction conditions of step (a) of Scheme 5 comprise a temperature up to about 80° C. and may depend on the thermostability of the enzyme used. In some embodiments, the reaction conditions comprise ambient temperature.

In some embodiments, the reaction conditions of step (b) of Scheme 5 comprise a base. In some embodiments, the base is KOH, NaOH, LiOH, CsOH, $K_3PO_4$, $K_2CO_3$, $Na_2CO_3$, $Li_2CO_3$, $Cs_2CO_3$, or other inorganic base. In some embodiments, the base is NaOH. In some embodiments, the reaction conditions of step (b) of Scheme 5 comprise a solvent, wherein the solvent is methanol, ethanol, isopropyl alcohol, dimethyl ether, cyclopentyl methyl ether, dioxane, MeTHF, MTBE, water, and mixtures thereof. In some embodiments, the solvent is ethanol and water. In some embodiments, the reaction conditions of step (b) of Scheme 5 comprises a temperature of about −15° C. about 40° C. In some embodiments, the reaction conditions of step (b) of Scheme 5 comprises a temperature of about 0° C.

Forms of Compound I

As described generally above, the present disclosure provides crystalline or amorphous forms of Compound I or salts, co-crystals, solvates, or hydrates thereof. In some embodiments, the crystalline form of a salt or co-crystal of Compound I is Compound I Choline Form I, Compound I Diethylamine Form I, Compound I N,N-dibenzylethylenediamine Form I, Compound I Ethanolamine Form I, or Compound I Form IX. Some embodiments provide for an amorphous form of a salt or co-crystal of Compound I as described herein.

Compound I Choline Form I

The present disclosure provides, in one embodiment, a choline salt or co-crystal of Compound I ("Compound I Choline Form I") having a crystalline form characterized by an X-ray powder diffractogram comprising peaks at 5.0, 7.8, and 9.4 °2θ±0.2 °2θ, as determined on a diffractometer using Cu-Kα radiation at a wavelength of 1.5406 Å. In one embodiment, the diffractogram further comprises peaks at 17.6, 21.3, and 23.9 °2θ±0.2 °2θ. In one embodiment, the diffractogram further comprises peaks at 11.0, 16.4, and 20.5 °2θ±0.2 °2θ. In one embodiment, the diffractogram is substantially as shown in FIG. 1.

In one embodiment, a choline salt or co-crystal of Compound I ("Compound I Choline Form I") having a crystalline form is characterized by an X-ray powder diffractogram comprising peaks at 5.0, 7.8, and 9.4 °2θ±0.1°2θ, as determined on a diffractometer using Cu-Kα radiation at a wavelength of 1.5406 Å. In one embodiment, the diffractogram further comprises peaks at 17.6, 21.3, and 23.9 °2θ±0.1 °2θ. In one embodiment, the diffractogram further comprises peaks at 11.0, 16.4, and 20.5 °2θ±0.1 °2θ.

In one embodiment, the diffractogram of Compound I Choline Form I comprises at least one or more peaks from: 5.0, 7.8, 9.4, 11.0, 16.4, 17.6, 20.5, 21.3, and 23.9 °2θ±0.2 °2θ. In one embodiment, the diffractogram of Compound I Choline Form I comprises at least two peaks from: 5.0, 7.8, 9.4, 11.0, 16.4, 17.6, 20.5, 21.3, and 23.9 °2θ±0.2 °2θ. In one embodiment, the diffractogram of Compound I Choline Form I comprises at least three peaks from: 5.0, 7.8, 9.4, 11.0, 16.4, 17.6, 20.5, 21.3, and 23.9 °2θ±0.2 °2θ. In one embodiment, the diffractogram of Compound I Choline Form I comprises at least four peaks from: 5.0, 7.8, 9.4, 11.0, 16.4, 17.6, 20.5, 21.3, and 23.9 °2θ±0.2 °2θ. In one embodiment, the diffractogram of Compound I Choline Form I comprises at least five peaks from: 5.0, 7.8, 9.4, 11.0, 16.4, 17.6, 20.5, 21.3, and 23.9 °2θ±0.2 °2θ. In one embodiment, the diffractogram of Compound I Choline Form I comprises at least six peaks from: 5.0, 7.8, 9.4, 11.0, 16.4, 17.6, 20.5, 21.3, and 23.9 °2θ±0.2 °2θ. In one embodiment, the diffractogram of Compound I Choline Form I comprises at least seven peaks from: 5.0, 7.8, 9.4, 11.0, 16.4, 17.6, 20.5, 21.3, and 23.9 °2θ±0.2 °2θ. In one embodiment, the diffractogram of Compound I Choline Form I comprises at least eight peaks from: 5.0, 7.8, 9.4, 11.0, 16.4, 17.6, 20.5, 21.3, and 23.9 °2θ±0.2 °2θ. In one embodiment, the diffractogram of Compound I Choline Form I comprises each of the following peaks: 5.0, 7.8, 9.4, 11.0, 16.4, 17.6, 20.5, 21.3, and 23.9 °2θ±0.2 °2θ.

In one embodiment, the diffractogram of Compound I Choline Form I comprises at least one or more peaks from: 5.0, 7.8, 9.4, 11.0, 16.4, 17.6, 20.5, 21.3, and 23.9 °2θ±0.1 °2θ. In one embodiment, the diffractogram of Compound I Choline Form I comprises at least two peaks from: 5.0, 7.8, 9.4, 11.0, 16.4, 17.6, 20.5, 21.3, and 23.9 °2θ±0.1 °2θ. In one embodiment, the diffractogram of Compound I Choline Form I comprises at least three peaks from: 5.0, 7.8, 9.4, 11.0, 16.4, 17.6, 20.5, 21.3, and 23.9 °2θ±0.1 °2θ. In one embodiment, the diffractogram of Compound I Choline Form I comprises at least four peaks from: 5.0, 7.8, 9.4, 11.0, 16.4, 17.6, 20.5, 21.3, and 23.9 °2θ±0.1 °2θ. In one embodiment, the diffractogram of Compound I Choline Form I comprises at least five peaks from: 5.0, 7.8, 9.4, 11.0, 16.4, 17.6, 20.5, 21.3, and 23.9 °2θ±0.1 °2θ. In one embodiment, the diffractogram of Compound I Choline Form I comprises at least six peaks from: 5.0, 7.8, 9.4, 11.0, 16.4, 17.6, 20.5, 21.3, and 23.9 °2θ±0.1 °2θ. In one embodiment, the diffractogram of Compound I Choline Form I comprises at least seven peaks from: 5.0, 7.8, 9.4, 11.0, 16.4, 17.6, 20.5, 21.3, and 23.9 °2θ±0.1 °2θ. In one embodiment, the diffractogram of Compound I Choline Form I comprises at least eight peaks from: 5.0, 7.8, 9.4, 11.0, 16.4, 17.6, 20.5, 21.3, and 23.9 °2θ±0.1 °2θ. In one embodiment, the diffractogram of Compound I Choline Form I comprises each of the following peaks: 5.0, 7.8, 9.4, 11.0, 16.4, 17.6, 20.5, 21.3, and 23.9 °2θ±0.1 °2θ.

Figure 2:
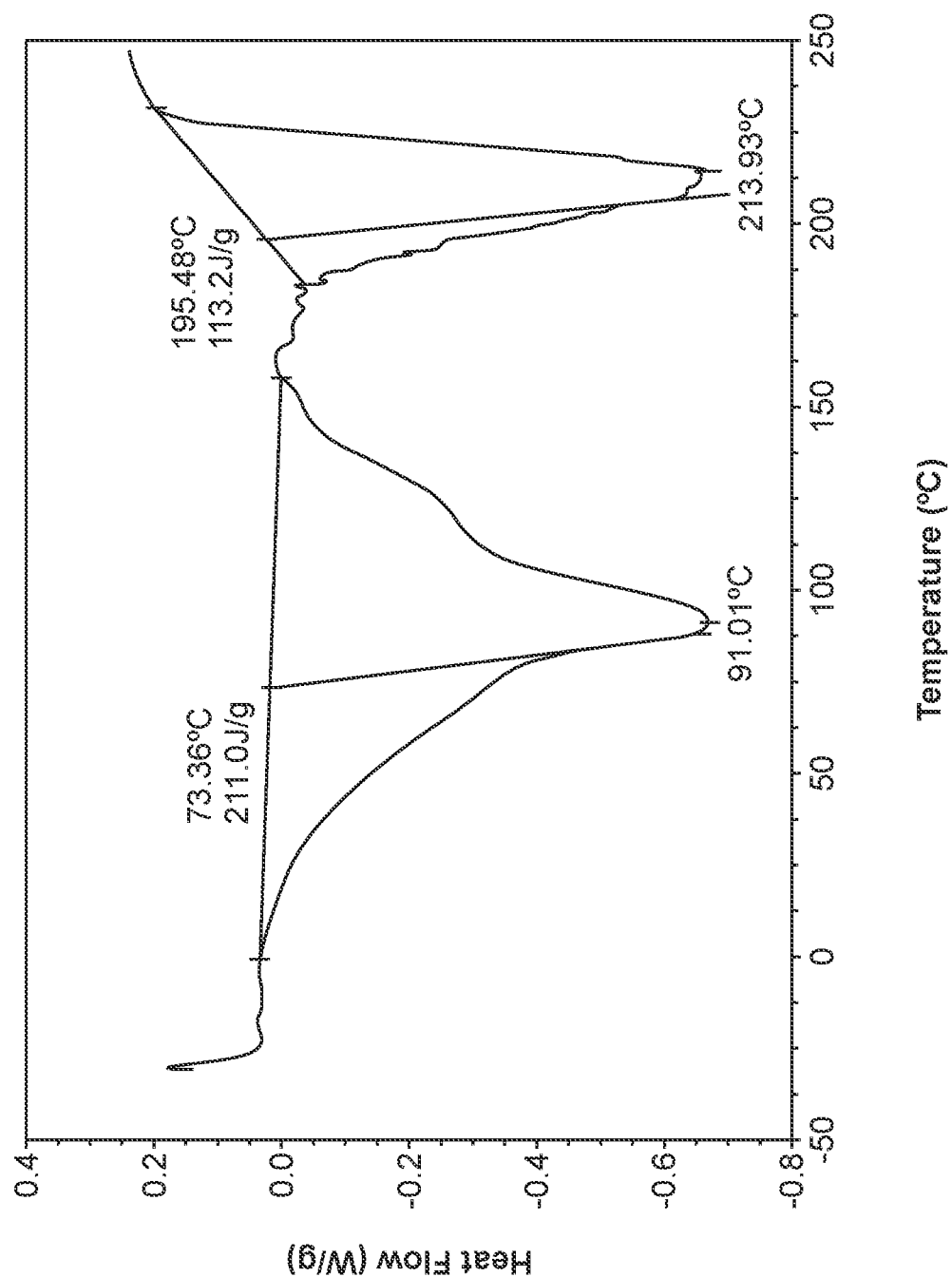
FIG. 2 shows a differential scanning calorimeter (DSC) curve of Compound I Choline Form I.

In one embodiment, Compound I Choline Form I is characterized by a differential scanning calorimetry (DSC) curve that comprises an endotherm at about 73° C. and an endotherm at about 195° C. In one embodiment, the DSC curve is substantially as shown in FIG. 2.

Compound I Diethylamine Form I

Figure 4:
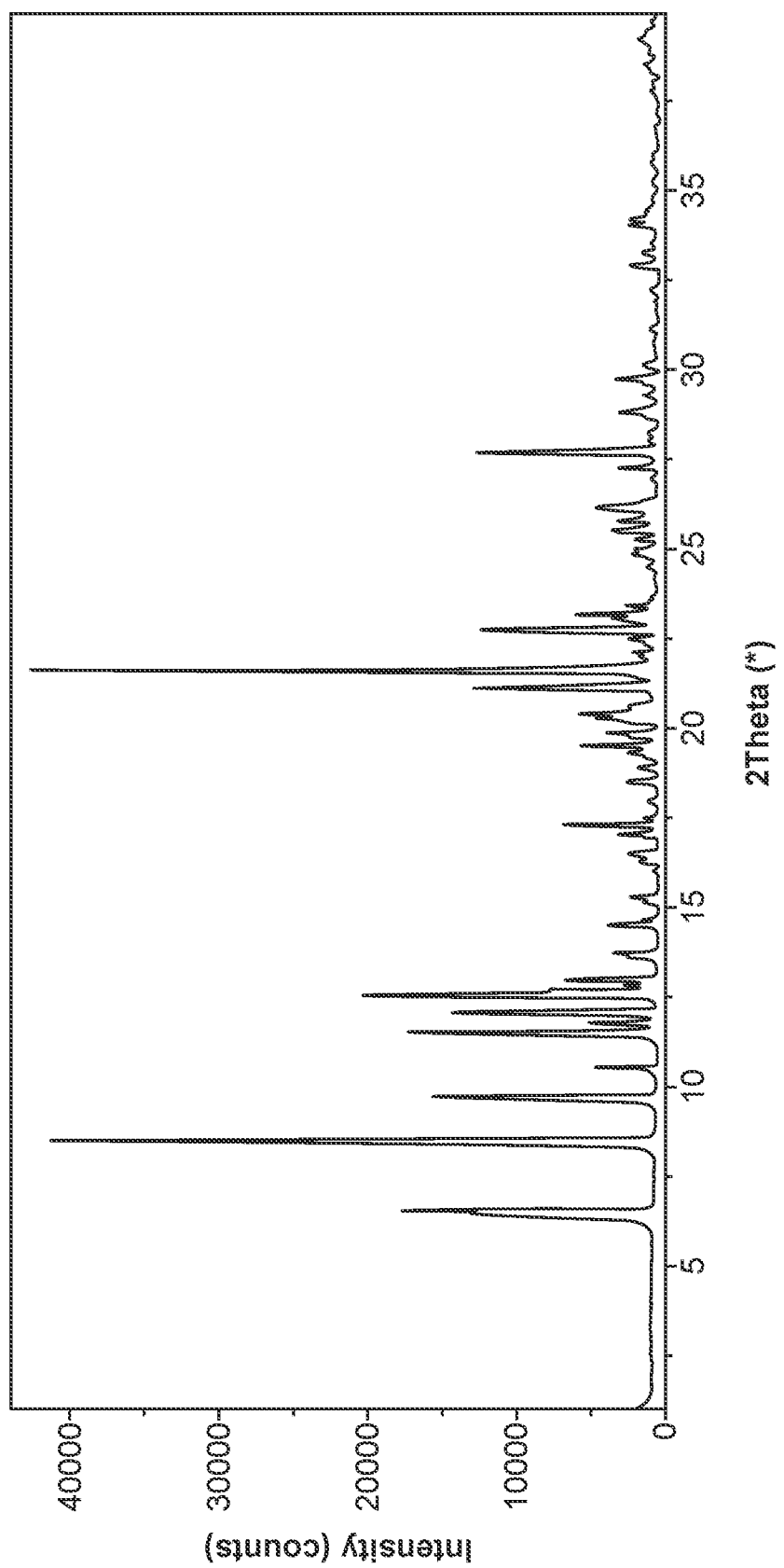
FIG. 4 shows an X-ray powder diffractogram of Compound I Diethylamine Form I.

The present disclosure provides, in one embodiment, a diethylamine salt or co-crystal of Compound I ("Compound I Diethylamine Form I") having a crystalline form characterized by an X-ray powder diffractogram comprising peaks at 6.5, 8.5, and 21.6 °2θ±0.2 °2θ, as determined on a diffractometer using Cu-Kα radiation at a wavelength of 1.5406 Å. In one embodiment, the diffractogram further comprises peaks at 9.7, 11.5, and 12.0 °2θ±0.2 °2θ. In one embodiment, the diffractogram further comprises peaks at 21.1, 22.8, and 27.7 °2θ±0.2 °2θ. In one embodiment, the diffractogram is substantially as shown in FIG. 4.

In one embodiment, a diethylamine salt or co-crystal of Compound I ("Compound I Diethylamine Form I") having a crystalline form is characterized by an X-ray powder diffractogram comprising peaks at 6.5, 8.5, and 21.6 °2θ±0.1 °2θ, as determined on a diffractometer using Cu-Kt radiation at a wavelength of 1.5406 Å. In one embodiment, the diffractogram further comprises peaks at 9.7, 11.5, and 12.0 °2θ±0.1 °2θ. In one embodiment, the diffractogram further comprises peaks at 21.1, 22.8, and 27.7 °2θ±0.1 °2θ.

In one embodiment, the diffractogram of Compound I Diethylamine Form I comprises at least one or more peaks from: 6.5, 8.5, 9.7, 11.5, 12.0, 21.1, 21.6, 22.8, and 27.7 °2θ±0.2 °2θ. In one embodiment, the diffractogram of Compound I Diethylamine Form I comprises at least two peaks from: 6.5, 8.5, 9.7, 11.5, 12.0, 21.1, 21.6, 22.8, and 27.7 °2θ±0.2 °2θ. In one embodiment, the diffractogram of Compound I Diethylamine Form I comprises at least three peaks from: 6.5, 8.5, 9.7, 11.5, 12.0, 21.1, 21.6, 22.8, and 27.7 °2θ±0.2 °2θ. In one embodiment, the diffractogram of Compound I Diethylamine Form I comprises at least four peaks from: 6.5, 8.5, 9.7, 11.5, 12.0, 21.1, 21.6, 22.8, and 27.7 °2θ±0.2 °2θ. In one embodiment, the diffractogram of Compound I Diethylamine Form I comprises at least five peaks from: 6.5, 8.5, 9.7, 11.5, 12.0, 21.1, 21.6, 22.8, and 27.7 °2θ±0.2 °2θ. In one embodiment, the diffractogram of Compound I Diethylamine Form I comprises at least six peaks from: 6.5, 8.5, 9.7, 11.5, 12.0, 21.1, 21.6, 22.8, and 27.7 °2θ±0.2 °2θ. In one embodiment, the diffractogram of Compound I Diethylamine Form I comprises at least seven peaks from: 6.5, 8.5, 9.7, 11.5, 12.0, 21.1, 21.6, 22.8, and 27.7 °2θ±0.2 °2θ. In one embodiment, the diffractogram of Compound I Diethylamine Form I comprises at least eight peaks from: 6.5, 8.5, 9.7, 11.5, 12.0, 21.1, 21.6, 22.8, and 27.7 °2θ±0.2 °2θ. In one embodiment, the diffractogram of Compound I Diethylamine Form I comprises each of the following peaks: 6.5, 8.5, 9.7, 11.5, 12.0, 21.1, 21.6, 22.8, and 27.7 °2θ±0.2 °2θ.

In one embodiment, the diffractogram of Compound I Diethylamine Form I comprises at least one or more peaks from: 6.5, 8.5, 9.7, 11.5, 12.0, 21.1, 21.6, 22.8, and 27.7 °2θ±0.1 °2θ. In one embodiment, the diffractogram of Compound I Diethylamine Form I comprises at least two peaks from: 6.5, 8.5, 9.7, 11.5, 12.0, 21.1, 21.6, 22.8, and 27.7 °2θ±0.1 °2θ. In one embodiment, the diffractogram of Compound I Diethylamine Form I comprises at least three peaks from: 6.5, 8.5, 9.7, 11.5, 12.0, 21.1, 21.6, 22.8, and 27.7 °2θ±0.1 °2θ. In one embodiment, the diffractogram of Compound I Diethylamine Form I comprises at least four peaks from: 6.5, 8.5, 9.7, 11.5, 12.0, 21.1, 21.6, 22.8, and 27.7 °2θ±0.1 °2θ. In one embodiment, the diffractogram of Compound I Diethylamine Form I comprises at least five peaks from: 6.5, 8.5, 9.7, 11.5, 12.0, 21.1, 21.6, 22.8, and 27.7 °2θ±0.1 °2θ. In one embodiment, the diffractogram of Compound I Diethylamine Form I comprises at least six peaks from: 6.5, 8.5, 9.7, 11.5, 12.0, 21.1, 21.6, 22.8, and 27.7 °2θ±0.1 °2θ. In one embodiment, the diffractogram of Compound I Diethylamine Form I comprises at least seven peaks from: 6.5, 8.5, 9.7, 11.5, 12.0, 21.1, 21.6, 22.8, and 27.7 °2θ±0.1 °2θ. In one embodiment, the diffractogram of Compound I Diethylamine Form I comprises at least eight peaks from: 6.5, 8.5, 9.7, 11.5, 12.0, 21.1, 21.6, 22.8, and 27.7 °2θ±0.1 °2θ. In one embodiment, the diffractogram of Compound I Diethylamine Form I comprises each of the following peaks: 6.5, 8.5, 9.7, 11.5, 12.0, 21.1, 21.6, 22.8, and 27.7 °2θ±0.1 °2θ.

Figure 6:
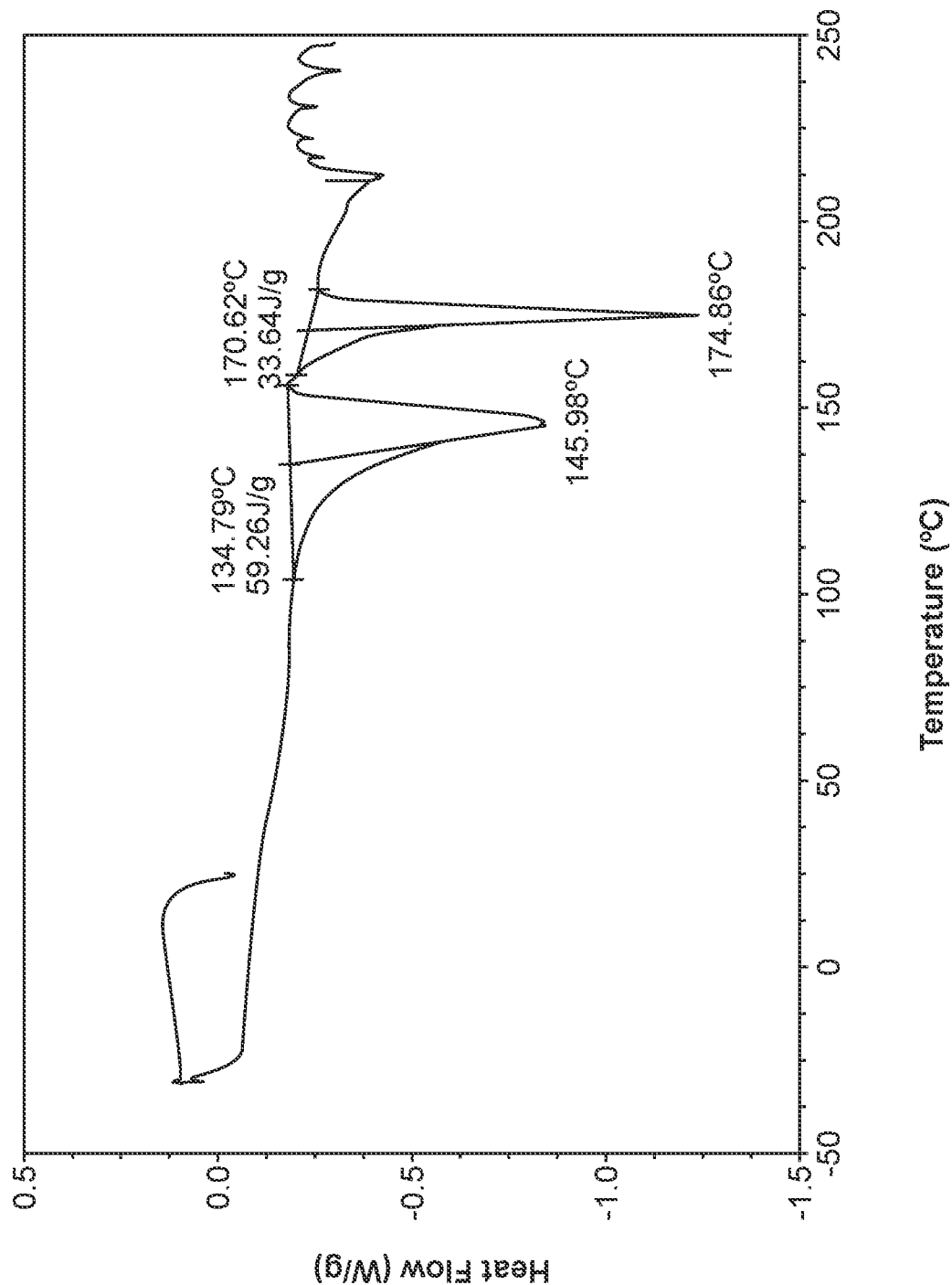
FIG. 6 shows a differential scanning calorimeter (DSC) curve of Compound I Diethylamine Form I.

In one embodiment, Compound I Diethylamine Form I is characterized by a differential scanning calorimetry (DSC) curve that comprises an endotherm at about 135° C. and an endotherm at about 171° C. In one embodiment, the DSC curve is substantially as shown in FIG. 6.

Compound I N,N-Dibenzylethylenediamine Form I

Figure 8:
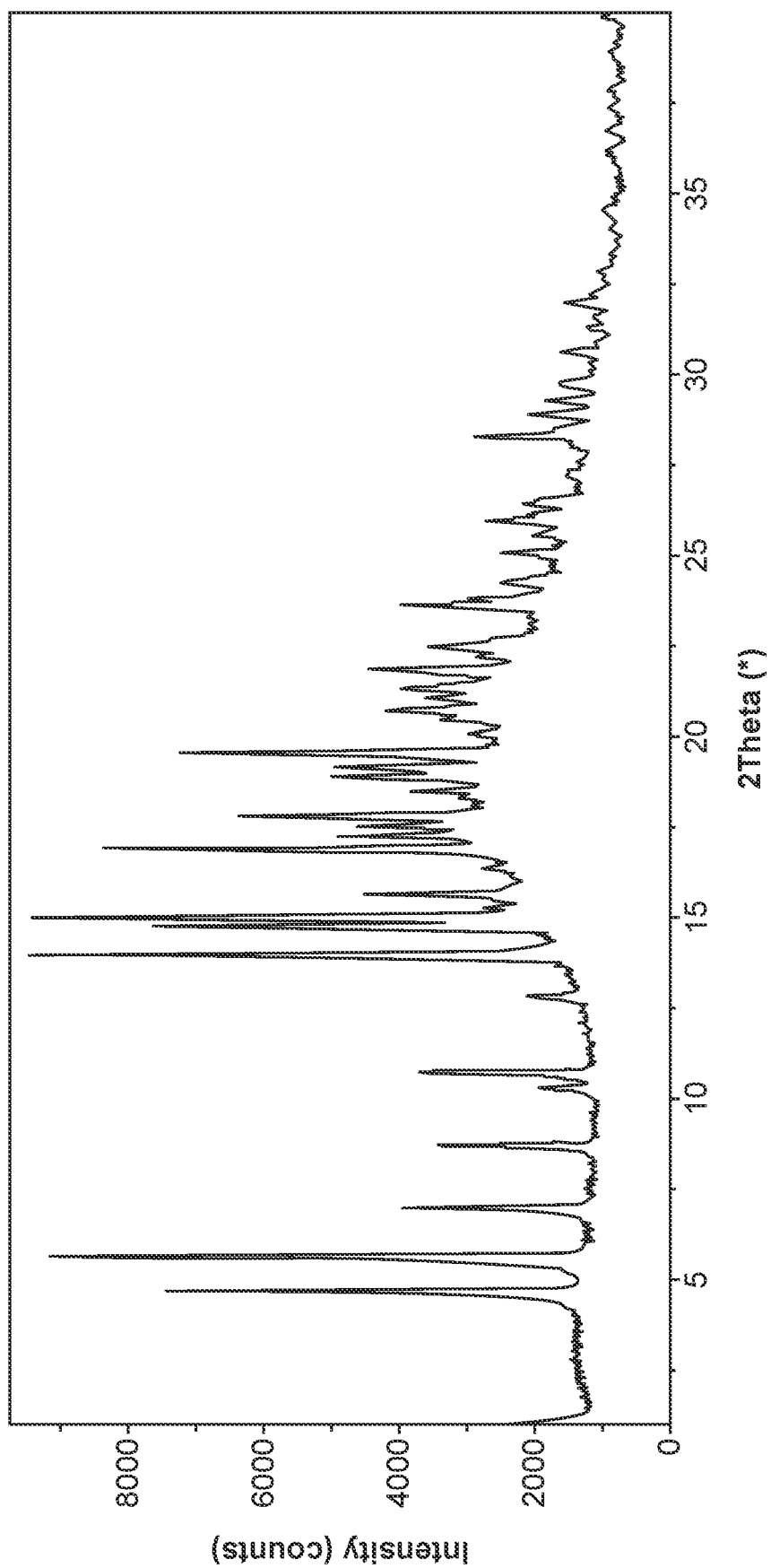
FIG. 8 shows an X-ray powder diffractogram of Compound I N,N-Dibenzylethylenediamine Form I.

The present disclosure provides, in one embodiment, a N,N-dibenzylethylenediamine salt or co-crystal of Compound I ("Compound I N,N-dibenzylethylenediamine Form I") having a crystalline form characterized by an X-ray powder diffractogram comprising peaks at 4.7, 5.6, and 14.0 °2θ±0.2 °2θ, as determined on a diffractometer using Cu-Kα radiation at a wavelength of 1.5406 Å. In one embodiment, the diffractogram further comprises peaks at 7.0, 16.9, and 19.6 °2θ±0.2 °2θ. In one embodiment, the diffractogram further comprises peaks at 8.7, 10.7, and 17.8 °2θ±0.2 °2θ. In one embodiment, the diffractogram is substantially as shown in FIG. 8.

In one embodiment, a N,N-dibenzylethylenediamine salt or co-crystal of Compound I ("Compound I N,N-dibenzylethylenediamine Form I") having a crystalline form is characterized by an X-ray powder diffractogram comprising peaks at 4.7, 5.6, and 14.0 °2θ±0.1 °2θ, as determined on a diffractometer using Cu-Kα radiation at a wavelength of 1.5406 Å. In one embodiment, the diffractogram further comprises peaks at 7.0, 16.9, and 19.6 °2θ±0.1 °2θ. In one embodiment, the diffractogram further comprises peaks at 8.7, 10.7, and 17.8 °2θ±0.1 °2θ.

In one embodiment, the diffractogram of Compound I N,N-dibenzylethylenediamine Form I comprises at least one or more peaks from: 4.7, 5.6, 7.0, 8.7, 10.7, 14.0, 16.9, 17.8, and 19.6 °2θ±0.2 °2θ. In one embodiment, the diffractogram of Compound I N,N-dibenzylethylenediamine Form I comprises at least two peaks from: 4.7, 5.6, 7.0, 8.7, 10.7, 14.0, 16.9, 17.8, and 19.6 °2θ±0.2 °2θ. In one embodiment, the diffractogram of Compound I N,N-dibenzylethylenediamine Form I comprises at least three peaks from: 4.7, 5.6, 7.0, 8.7, 10.7, 14.0, 16.9, 17.8, and 19.6 °2θ±0.2 °2θ. In one embodiment, the diffractogram of Compound I N,N-dibenzylethylenediamine Form I comprises at least four peaks from: 4.7, 5.6, 7.0, 8.7, 10.7, 14.0, 16.9, 17.8, and 19.6 °2θ±0.2 °2θ. In one embodiment, the diffractogram of Compound I N,N-dibenzylethylenediamine Form I comprises at least five peaks from: 4.7, 5.6, 7.0, 8.7, 10.7, 14.0, 16.9, 17.8, and 19.6 °2θ±0.2 °2θ. In one embodiment, the diffractogram of Compound I N,N-dibenzylethylenediamine Form I comprises at least six peaks from: 4.7, 5.6, 7.0, 8.7, 10.7, 14.0, 16.9, 17.8, and 19.6 °2θ±0.2 °2θ. In one embodiment, the diffractogram of Compound I N,N-dibenzylethylenediamine Form I comprises at least seven peaks from: 4.7, 5.6, 7.0, 8.7, 10.7, 14.0, 16.9, 17.8, and 19.6 °2θ±0.2 °2θ. In one embodiment, the diffractogram of Compound I N,N-dibenzylethylenediamine Form I comprises at least eight peaks from: 4.7, 5.6, 7.0, 8.7, 10.7, 14.0, 16.9, 17.8, and 19.6 °2θ±0.2 °2θ. In one embodiment, the diffractogram of Compound I N,N-dibenzylethylenediamine Form I comprises each of the following peaks: 4.7, 5.6, 7.0, 8.7, 10.7, 14.0, 16.9, 17.8, and 19.6 °2θ±0.2 °2θ.

In one embodiment, the diffractogram of Compound I N,N-dibenzylethylenediamine Form I comprises at least one or more peaks from: 4.7, 5.6, 7.0, 8.7, 10.7, 14.0, 16.9, 17.8, and 19.6 °2θ±0.1 °2θ. In one embodiment, the diffractogram of Compound I N,N-dibenzylethylenediamine Form I comprises at least two peaks from: 4.7, 5.6, 7.0, 8.7, 10.7, 14.0, 16.9, 17.8, and 19.6 °2θ±0.1 °2θ. In one embodiment, the diffractogram of Compound I N,N-dibenzylethylenediamine Form I comprises at least three peaks from: 4.7, 5.6, 7.0, 8.7, 10.7, 14.0, 16.9, 17.8, and 19.6 °2θ±0.1 °2θ. In one embodiment, the diffractogram of Compound I N,N-dibenzylethylenediamine Form I comprises at least four peaks from: 4.7, 5.6, 7.0, 8.7, 10.7, 14.0, 16.9, 17.8, and 19.6 °2θ±0.1 °2θ. In one embodiment, the diffractogram of Compound I N,N-dibenzylethylenediamine Form I comprises at least five peaks from: 4.7, 5.6, 7.0, 8.7, 10.7, 14.0, 16.9, 17.8, and 19.6 °2θ±0.1 °2θ. In one embodiment, the diffractogram of Compound I N,N-dibenzylethylenediamine Form I comprises at least six peaks from: 4.7, 5.6, 7.0, 8.7, 10.7, 14.0, 16.9, 17.8, and 19.6 °2θ±0.1 °2θ. In one embodiment, the diffractogram of Compound I N,N-dibenzylethylenediamine Form I comprises at least seven peaks from: 4.7, 5.6, 7.0, 8.7, 10.7, 14.0, 16.9, 17.8, and 19.6 °2θ±0.1 °2θ. In one embodiment, the diffractogram of Compound I N,N-dibenzylethylenediamine Form I comprises at least eight peaks from: 4.7, 5.6, 7.0, 8.7, 10.7, 14.0, 16.9, 17.8, and 19.6 °2θ±0.1 °2θ. In one embodiment, the diffractogram of Compound I N,N-dibenzylethylenediamine Form I comprises each of the following peaks: 4.7, 5.6, 7.0, 8.7, 10.7, 14.0, 16.9, 17.8, and 19.6 °2θ±0.1 °2θ.

Figure 9:
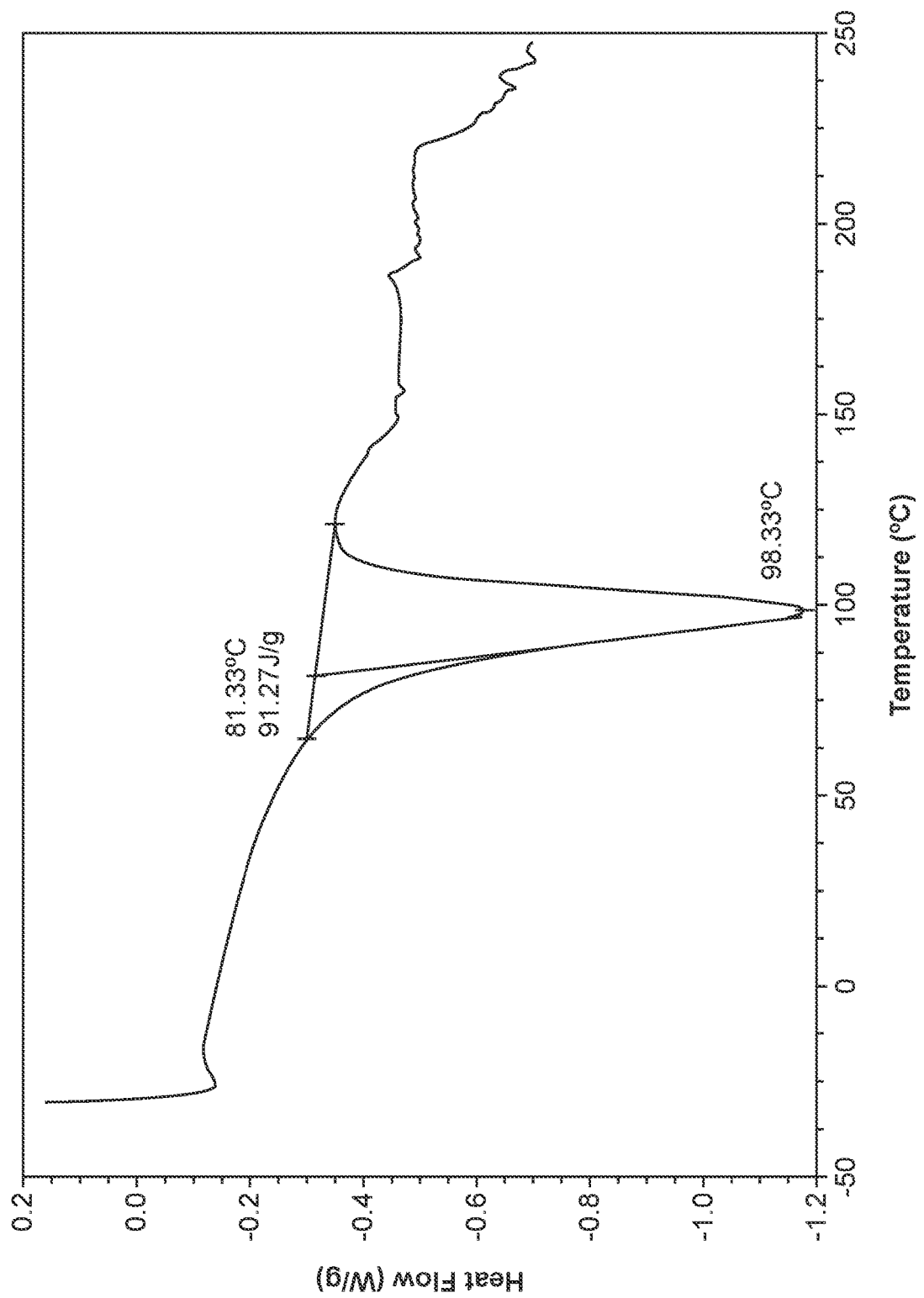
FIG. 9 shows a differential scanning calorimeter (DSC) curve of Compound I N,N-Dibenzylethylenediamine Form I.

In one embodiment, Compound I N,N-dibenzylethylenediamine Form I is characterized by a differential scanning calorimetry (DSC) curve that comprises an endotherm at about 81° C. In one embodiment, the DSC curve is substantially as shown in FIG. 9.

Compound I Ethanolamine Form I

Figure 11:
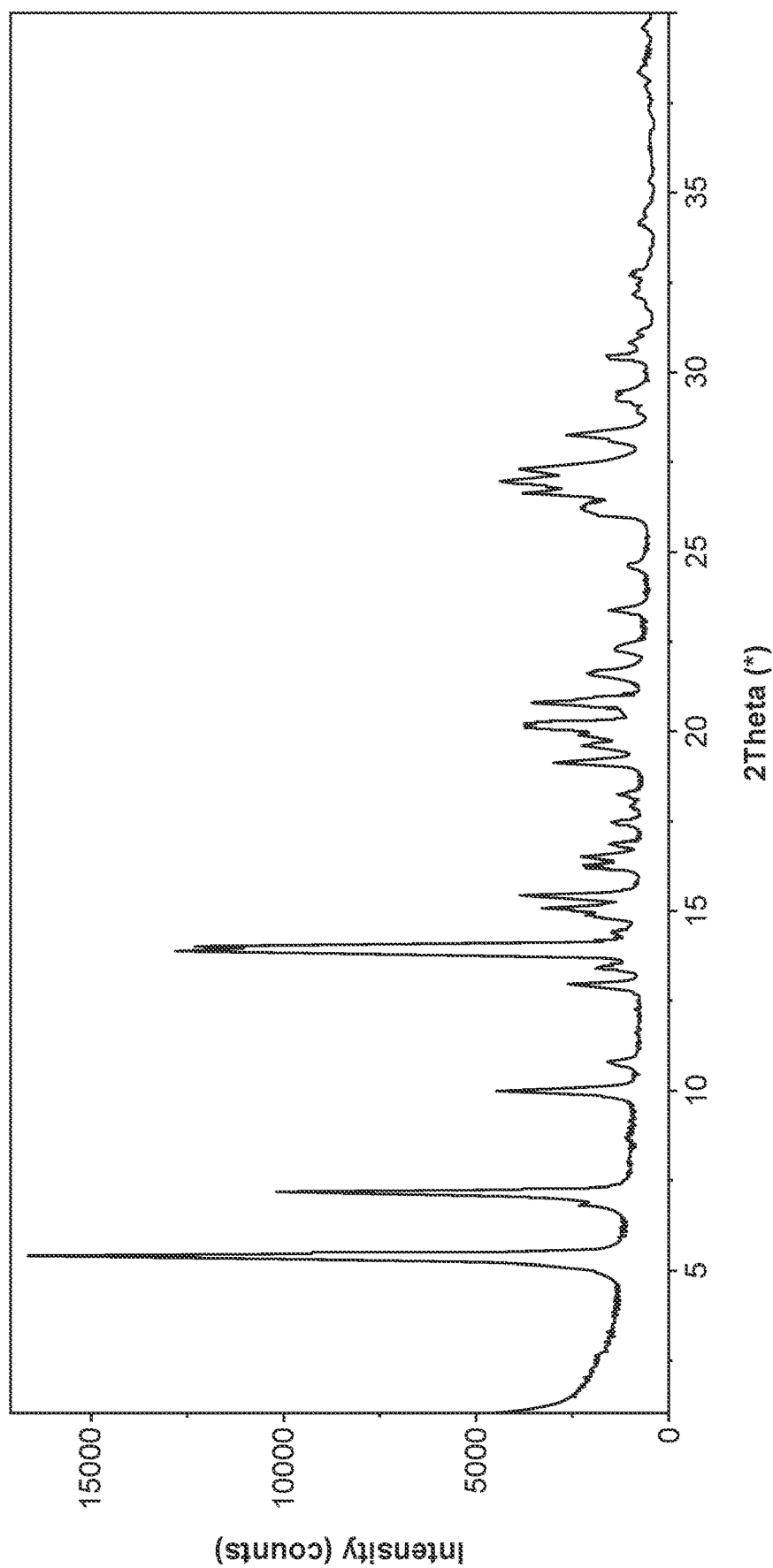
FIG. 11 shows an X-ray powder diffractogram of Compound I Ethanolamine Form I.

The present disclosure provides, in one embodiment, an ethanolamine salt or co-crystal of Compound I ("Compound I Ethanolamine Form I") having a crystalline form characterized by an X-ray powder diffractogram comprising peaks at 5.4, 7.2, and 10.0 °2θ±0.2 °2θ, as determined on a diffractometer using Cu-Kα radiation at a wavelength of 1.5406 Å. In one embodiment, the diffractogram further comprises peaks at 15.4, 19.1, and 20.7 °2θ±0.2 °2θ. In one embodiment, the diffractogram further comprises peaks at 21.6, 23.4, and 28.3 °2θ±0.2 °2θ. In one embodiment, the diffractogram is substantially as shown in FIG. 11.

In one embodiment, an ethanolamine salt or co-crystal of Compound I ("Compound I Ethanolamine Form I") having a crystalline form is characterized by an X-ray powder diffractogram comprising peaks at 5.4, 7.2, and 10.0 °2θ±0.1 °2θ, as determined on a diffractometer using Cu-Kα radiation at a wavelength of 1.5406 Å. In one embodiment, the diffractogram further comprises peaks at 15.4, 19.1, and 20.7 °2θ±0.1 °2θ. In one embodiment, the diffractogram further comprises peaks at 21.6, 23.4, and 28.3 °2θ±0.1 °2θ.

In one embodiment, the diffractogram of Compound I Ethanolamine Form I comprises at least one or more peaks from: 5.4, 7.2, 10.0, 15.4, 19.1, 20.7, 21.6, 23.4, and 28.3 °2θ±0.2 °2θ. In one embodiment, the diffractogram of Compound I Ethanolamine Form I comprises at least two peaks from: 5.4, 7.2, 10.0, 15.4, 19.1, 20.7, 21.6, 23.4, and 28.3 °2θ±0.2° 2θ. In one embodiment, the diffractogram of Compound I Ethanolamine Form I comprises at least three peaks from: 5.4, 7.2, 10.0, 15.4, 19.1, 20.7, 21.6, 23.4, and 28.3 °2θ±0.2 °2θ. In one embodiment, the diffractogram of Compound I Ethanolamine Form I comprises at least four peaks from: 5.4, 7.2, 10.0, 15.4, 19.1, 20.7, 21.6, 23.4, and 28.3 °2θ±0.2 °2θ. In one embodiment, the diffractogram of Compound I Ethanolamine Form I comprises at least five peaks from: 5.4, 7.2, 10.0, 15.4, 19.1, 20.7, 21.6, 23.4, and 28.3 °2θ±0.2 °2θ. In one embodiment, the diffractogram of Compound I Ethanolamine Form I comprises at least six peaks from: 5.4, 7.2, 10.0, 15.4, 19.1, 20.7, 21.6, 23.4, and 28.3 °2θ±0.2 °2θ. In one embodiment, the diffractogram of Compound I Ethanolamine Form I comprises at least seven peaks from: 5.4, 7.2, 10.0, 15.4, 19.1, 20.7, 21.6, 23.4, and 28.3 °2θ±0.2 °2θ. In one embodiment, the diffractogram of Compound I Ethanolamine Form I comprises at least eight peaks from: 5.4, 7.2, 10.0, 15.4, 19.1, 20.7, 21.6, 23.4, and 28.3 °2θ±0.2 °2θ. In one embodiment, the diffractogram of Compound I Ethanolamine Form I comprises each of the following peaks: 5.4, 7.2, 10.0, 15.4, 19.1, 20.7, 21.6, 23.4, and 28.3 °2θ±0.2 °2θ.

In one embodiment, the diffractogram of Compound I Ethanolamine Form I comprises at least one or more peaks from: 5.4, 7.2, 10.0, 15.4, 19.1, 20.7, 21.6, 23.4, and 28.3 °2θ±0.1 °2θ. In one embodiment, the diffractogram of Compound I Ethanolamine Form I comprises at least two peaks from: 5.4, 7.2, 10.0, 15.4, 19.1, 20.7, 21.6, 23.4, and 28.3 °2θ±0.1 °2θ. In one embodiment, the diffractogram of Compound I Ethanolamine Form I comprises at least three peaks from: 5.4, 7.2, 10.0, 15.4, 19.1, 20.7, 21.6, 23.4, and 28.3 °2θ±0.1 °2θ. In one embodiment, the diffractogram of Compound I Ethanolamine Form I comprises at least four peaks from: 5.4, 7.2, 10.0, 15.4, 19.1, 20.7, 21.6, 23.4, and 28.3 °2θ±0.1 °2θ. In one embodiment, the diffractogram of Compound I Ethanolamine Form I comprises at least five peaks from: 5.4, 7.2, 10.0, 15.4, 19.1, 20.7, 21.6, 23.4, and 28.3 °2θ±0.1 °2θ. In one embodiment, the diffractogram of Compound I Ethanolamine Form I comprises at least six peaks from: 5.4, 7.2, 10.0, 15.4, 19.1, 20.7, 21.6, 23.4, and 28.3 °2θ±0.1 °2θ. In one embodiment, the diffractogram of Compound I Ethanolamine Form I comprises at least seven peaks from: 5.4, 7.2, 10.0, 15.4, 19.1, 20.7, 21.6, 23.4, and 28.3 °2θ±0.1 °2θ. In one embodiment, the diffractogram of Compound I Ethanolamine Form I comprises at least eight peaks from: 5.4, 7.2, 10.0, 15.4, 19.1, 20.7, 21.6, 23.4, and 28.3 °2θ±0.1 °2θ. In one embodiment, the diffractogram of Compound I Ethanolamine Form I comprises each of the following peaks: 5.4, 7.2, 10.0, 15.4, 19.1, 20.7, 21.6, 23.4, and 28.3 °2θ±0.1 °2θ.

Figure 12:
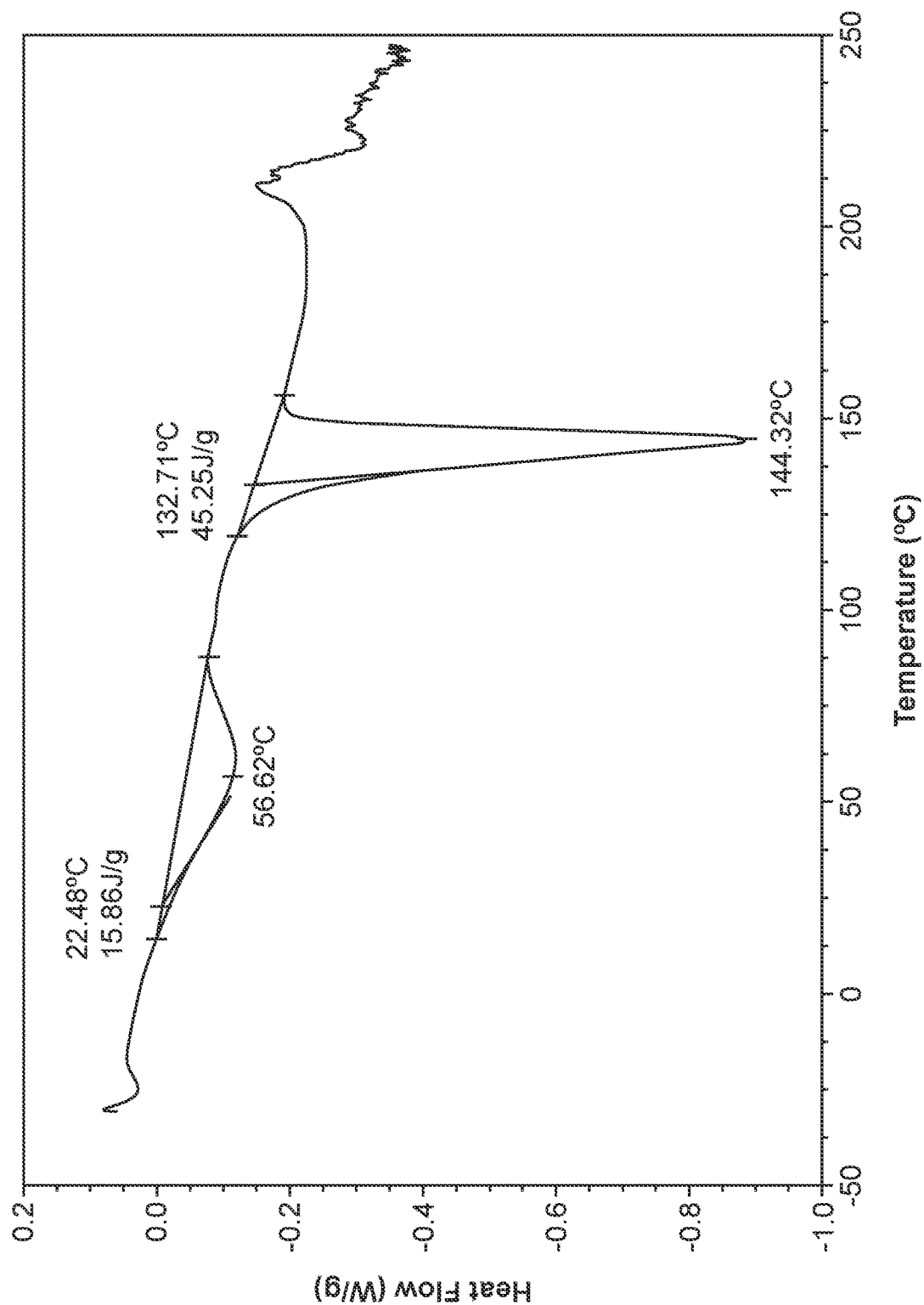
FIG. 12 shows a differential scanning calorimeter (DSC) curve of Compound I Ethanolamine Form I.

In one embodiment, Compound I Ethanolamine Form I is characterized by a differential scanning calorimetry (DSC) curve that comprises an endotherm at about 22° C. and an endotherm at about 133° C. In one embodiment, the DSC curve is substantially as shown in FIG. 12.

Compound I Form IX

Figure 14:
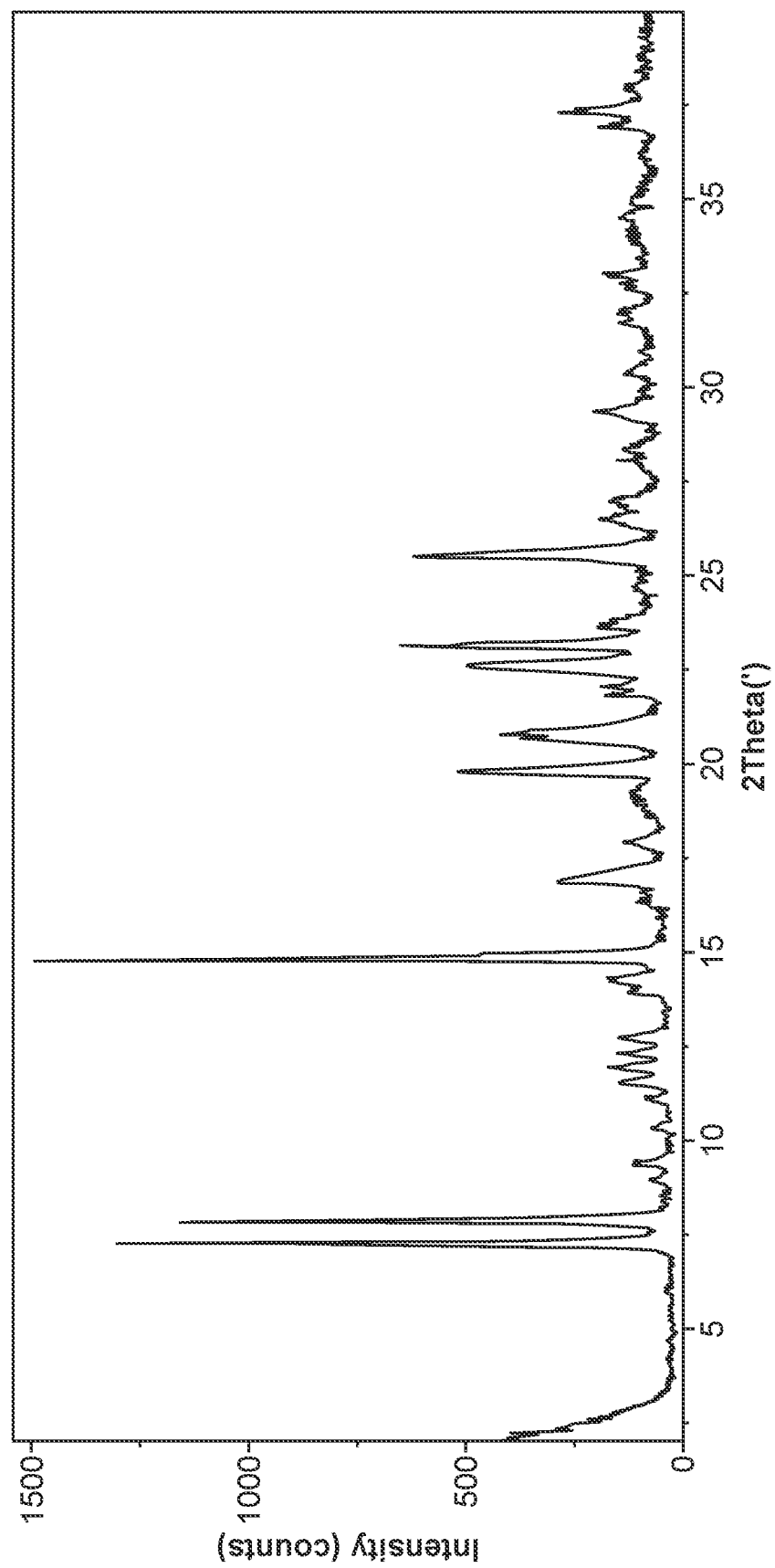
FIG. 14 shows an X-ray powder diffractogram of Compound I Form IX.

The present disclosure provides, in one embodiment, a crystalline form of Compound I referred to as "Compound I Form IX." In some embodiments, a crystalline form of Compound I Form IX is characterized by an X-ray powder diffractogram comprising peaks at 7.2, 7.8, and 14.8 °2θ±0.2 °2θ, as determined on a diffractometer using Cu-Kα radiation at a wavelength of 1.5406 Å. In one embodiment, the diffractogram further comprises peaks at 19.8, 23.1, and 25.5 °2θ±0.2 °2θ. In one embodiment, the diffractogram further comprises peaks at 16.8, 20.8, and 22.6 °2θ±0.2 °2θ. In one embodiment, the diffractogram is substantially as shown in FIG. 14.

In one embodiment, Compound I Form IX having a crystalline form is characterized by an X-ray powder diffractogram comprising peaks at 7.2, 7.8, and 14.8 °2θ±0.1 °2θ, as determined on a diffractometer using Cu-Kα radiation at a wavelength of 1.5406 Å. In one embodiment, the diffractogram further comprises peaks at 19.8, 23.1, and 25.5 °2θ±0.1 °2θ. In one embodiment, the diffractogram further comprises peaks at 16.8, 20.8, and 22.6 °2θ±0.1 °2θ.

In one embodiment, the diffractogram of Compound I Form IX comprises at least one or more peaks from: 7.2, 7.8, 14.8, 16.8, 19.8, 20.8, 22.6, 23.1, and 25.5 °2θ±0.2 °2θ. In one embodiment, the diffractogram of Compound I Form IX comprises at least two peaks from: 7.2, 7.8, 14.8, 16.8, 19.8, 20.8, 22.6, 23.1, and 25.5 °2θ±0.2 °2θ. In one embodiment, the diffractogram of Compound I Form IX comprises at least three peaks from: 7.2, 7.8, 14.8, 16.8, 19.8, 20.8, 22.6, 23.1, and 25.5 °2θ±0.2 °2θ. In one embodiment, the diffractogram of Compound I Form IX comprises at least four peaks from: 7.2, 7.8, 14.8, 16.8, 19.8, 20.8, 22.6, 23.1, and 25.5 °2θ±0.2 °2θ. In one embodiment, the diffractogram of Compound I Form IX comprises at least five peaks from: 7.2, 7.8, 14.8, 16.8, 19.8, 20.8, 22.6, 23.1, and 25.5 °2θ±0.2 °2θ. In one embodiment, the diffractogram of Compound I Form IX comprises at least six peaks from: 7.2, 7.8, 14.8, 16.8, 19.8, 20.8, 22.6, 23.1, and 25.5 °2θ±0.2 °2θ. In one embodiment, the diffractogram of Compound I Form IX comprises at least seven peaks from: 7.2, 7.8, 14.8, 16.8, 19.8, 20.8, 22.6, 23.1, and 25.5 °2θ±0.2 °2θ. In one embodiment, the diffractogram of Compound I Form IX comprises at least eight peaks from: 7.2, 7.8, 14.8, 16.8, 19.8, 20.8, 22.6, 23.1, and 25.5 °2θ±0.2 °2θ. In one embodiment, the diffractogram of Compound I Form IX comprises each of the following peaks: 0.2, 7.8, 14.8, 16.8, 19.8, 20.8, 22.6, 23.1, and 25.5 °2θ±0.2 °2θ.

In one embodiment, the diffractogram of Compound I Form IX comprises at least one or more peaks from: 7.2, 7.8, 14.8, 16.8, 19.8, 20.8, 22.6, 23.1, and 25.5 °2θ±0.1 °2θ. In one embodiment, the diffractogram of Compound I Form IX comprises at least two peaks from: 7.2, 7.8, 14.8, 16.8, 19.8, 20.8, 22.6, 23.1, and 25.5 °2θ±0.1 °2θ. In one embodiment, the diffractogram of Compound I Form IX comprises at least three peaks from: 7.2, 7.8, 14.8, 16.8, 19.8, 20.8, 22.6, 23.1, and 25.5 °2θ±0.1 °2θ. In one embodiment, the diffractogram of Compound I Form IX comprises at least four peaks from: 7.2, 7.8, 14.8, 16.8, 19.8, 20.8, 22.6, 23.1, and 25.5 °2θ±0.1 °2θ. In one embodiment, the diffractogram of Compound I Form IX comprises at least five peaks from: 7.2, 7.8, 14.8, 16.8, 19.8, 20.8, 22.6, 23.1, and 25.5 °2θ±0.1 °2θ. In one embodiment, the diffractogram of Compound I Form IX comprises at least six peaks from: 7.2, 7.8, 14.8, 16.8, 19.8, 20.8, 22.6, 23.1, and 25.5 °2θ±0.1 °2θ. In one embodiment, the diffractogram of Compound I Form IX comprises at least seven peaks from: 7.2, 7.8, 14.8, 16.8, 19.8, 20.8, 22.6, 23.1, and 25.5 °2θ±0.1 °2θ. In one embodiment, the diffractogram of Compound I Form IX comprises at least eight peaks from: 7.2, 7.8, 14.8, 16.8, 19.8, 20.8, 22.6, 23.1, and 25.5 °2θ±0.1 °2θ. In one embodiment, the diffractogram of Compound I Form IX comprises each of the following peaks: 0.2, 7.8, 14.8, 16.8, 19.8, 20.8, 22.6, 23.1, and 25.5 °2θ±0.1 °2θ.

Figure 15:
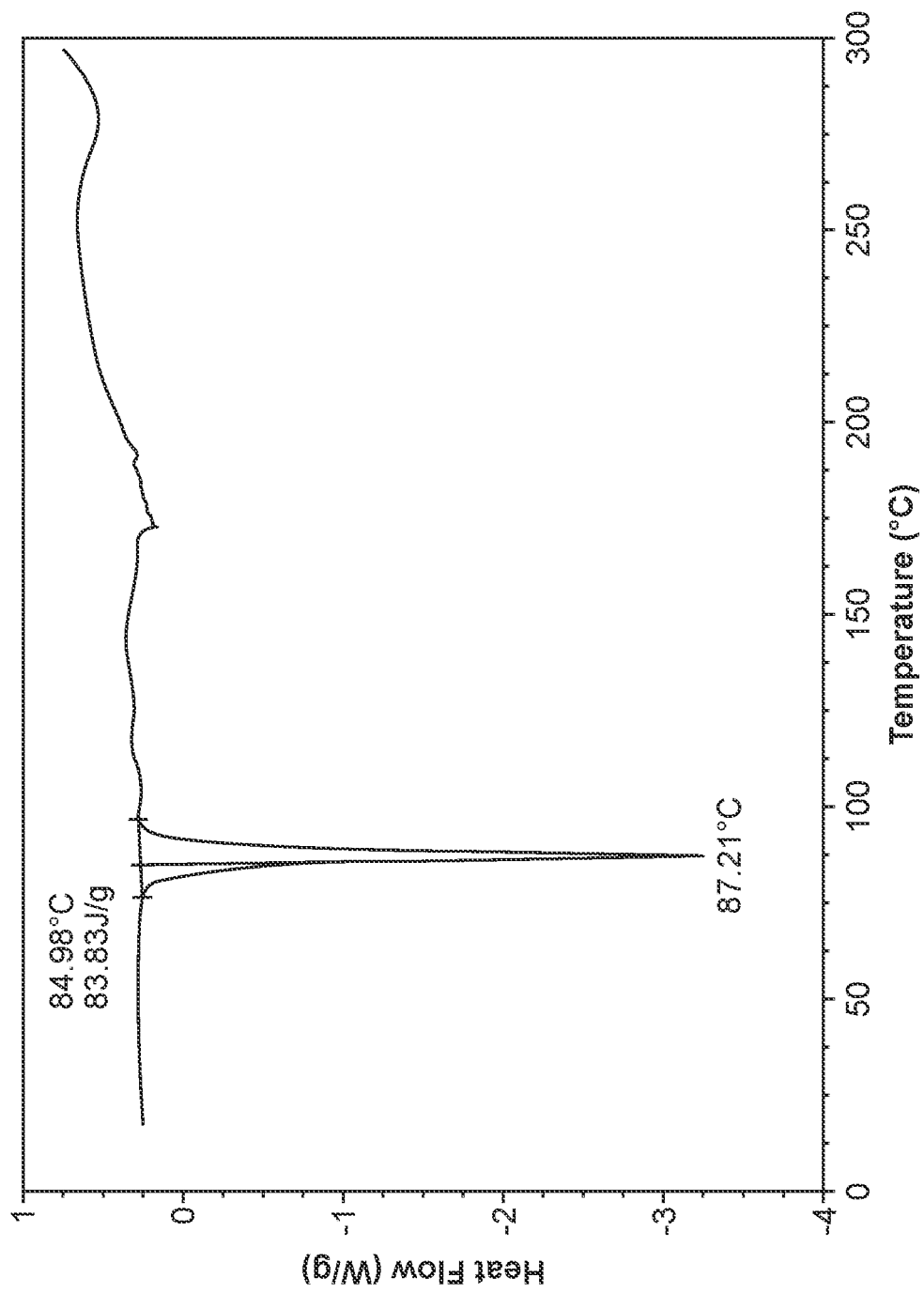
FIG. 15 shows a differential scanning calorimeter (DSC) curve of Compound I Form IX.

In one embodiment, Compound I Form IX is characterized by a differential scanning calorimetry (DSC) curve that comprises an endotherm at about 85° C. In one embodiment, the DSC curve is substantially as shown in FIG. 15.

Uses, Formulation and Administration and Pharmaceutically Acceptable Compositions According to another embodiment, the disclosure provides a composition comprising a compound of this disclosure or a pharmaceutically acceptable salt, ester, or salt of ester thereof and a pharmaceutically acceptable carrier, adjuvant, or vehicle. Some embodiments provide for a composition comprising a compound as described herein, or a pharmaceutically acceptable salt or co-crystal thereof, and a pharmaceutically acceptable carrier, adjuvant, or vehicle.

Some embodiments provide for a composition comprising a crystalline or amorphous form of Compound I as described herein. The amount of compound in compositions of this disclosure is such that is effective to measurably inhibit ACC, in a biological sample or in a patient. In certain embodiments, the amount of compound in compositions of this disclosure is such that is effective to measurably inhibit ACC, in a biological sample or in a patient. In certain embodiments, a composition of this disclosure is formulated for disclosure to a patient in need of such composition. In some embodiments, a composition of this disclosure is formulated for oral administration to a patient.

The term "compound" as used herein, means an ACC inhibitor as described herein (including but not limited to Compound I), or a solid form thereof. In some embodiments, the term "compound" as used herein, means an ACC inhibitor as described herein (including but not limited to Compound I), or a salt or solid form thereof.

In some embodiments, the term "compound" as used herein, means an intermediate useful for the synthesis of an ACC inhibitor as described herein, or a salt or solid form thereof.

In some embodiments, a compound is Compound I or a pharmaceutically acceptable salt thereof. In some embodiments, a compound is Compound I or a pharmaceutically acceptable salt or pharmaceutically acceptable co-crystal thereof.

Some embodiments provided herein provide for a pharmaceutical composition comprising a crystalline form of a salt or co-crystal of Compound I and a pharmaceutically acceptable carrier, adjuvant, or vehicle. In some embodiments, the crystalline form of a salt or co-crystal of Compound I is Compound I Choline Form I, Compound I Diethylamine Form I, Compound I N,N-dibenzylethylenediamine Form I, Compound I Ethanolamine Form I, or Compound I Form IX.

Some embodiments are directed to pharmaceutical compositions comprising a crystalline form of Compound I as described herein. In one embodiment, a pharmaceutical composition comprises Compound I, wherein at least 95% of Compound I is in a crystalline form as described herein. In one embodiment, a pharmaceutical composition comprises Compound I, wherein at least 95% of Compound I is in Compound I Choline Form I. In one embodiment, a pharmaceutical composition comprises Compound I, wherein at least 95% of Compound I is in Compound I Diethylamine Form I. In one embodiment, a pharmaceutical composition comprises Compound I, wherein at least 95% of Compound I is in Compound I N,N-dibenzylethylenediamine Form I. In one embodiment, a pharmaceutical composition comprises Compound I, wherein at least 95% of Compound I is in Compound I Ethanolamine Form I. In one embodiment, a pharmaceutical composition comprises Compound I, wherein at least 95% of Compound I is in Compound I Form IX.

Some embodiments are directed to pharmaceutical compositions comprising a crystalline form of Compound I as described herein. In one embodiment, a pharmaceutical composition comprises Compound I, wherein at least 97% of Compound I is in a crystalline form as described herein. In one embodiment, a pharmaceutical composition comprises Compound I, wherein at least 97% of Compound I is in Compound I Choline Form I. In one embodiment, a pharmaceutical composition comprises Compound I, wherein at least 97% of Compound I is in Compound I Diethylamine Form I. In one embodiment, a pharmaceutical composition comprises Compound I, wherein at least 97% of Compound I is in Compound I N,N-dibenzylethylenediamine Form I. In one embodiment, a pharmaceutical composition comprises Compound I, wherein at least 97% of Compound I is in Compound I Ethanolamine Form I. In one embodiment, a pharmaceutical composition comprises Compound I, wherein at least 97% of Compound I is in Compound I Form IX.

Some embodiments are directed to pharmaceutical compositions comprising a crystalline form of Compound I as described herein. In one embodiment, a pharmaceutical composition comprises Compound I, wherein at least 99% of Compound I is in a crystalline form as described herein. In one embodiment, a pharmaceutical composition comprises Compound I, wherein at least 99% of Compound I is in Compound I Choline Form I. In one embodiment, a pharmaceutical composition comprises Compound I, wherein at least 99% of Compound I is in Compound I Diethylamine Form I. In one embodiment, a pharmaceutical composition comprises Compound I, wherein at least 99% of Compound I is in Compound I N,N-dibenzylethylenediamine Form I. In one embodiment, a pharmaceutical composition comprises Compound I, wherein at least 99% of Compound I is in Compound I Ethanolamine Form I. In one embodiment, a pharmaceutical composition comprises Compound I, wherein at least 99% of Compound I is in Compound I Form IX.

The term "patient," as used herein, means an animal, a mammal, or a human.

The term "pharmaceutically acceptable carrier, adjuvant, or diluent" refers to a nontoxic carrier, adjuvant, or vehicle that does not destroy the pharmacological activity of the compound with which it is formulated. Pharmaceutically acceptable carriers, adjuvants or diluents that may be used in the compositions of this disclosure include, but are not limited to, antiadherents, binders, coatings, colorants, disintegrants, flavors, glidants, lubricants, preservatives, sorbents, and vehicles. Examples of carriers, adjuvants, and diluents include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, a pharmaceutically acceptable composition comprising a crystalline form of a salt or co-crystal of Compound I as described herein is administered as a capsule. In some embodiments, a pharmaceutically acceptable composition comprising a crystalline form of Compound I as described herein is administered as a tablet.

Alternatively, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of compounds of the present disclosure that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

In some embodiments, a crystalline form of Compound I is administered at a dose of about 2 milligrams to about 500 milligrams per day, about 2 milligrams to about 400 milligrams per day, about 2 milligrams to about 300 milligrams per day, about 2 milligrams to about 200 milligrams per day, or about 2 milligrams to about 100 milligrams per day. In some embodiments, a crystalline form of Compound I is administered at a dose of about 5 milligrams per day, about 6 milligrams per day, about 7 milligrams per day, about 8 milligrams per day, about 9 milligrams per day, about 10 milligrams per day, about 11 milligrams per day, about 12 milligrams per day, about 13 milligrams per day, about 14 milligrams per day, about 15 milligrams per day, 16 milligrams per day, 17 milligrams per day, 18 milligrams per day, 19 milligrams per day, 20 milligrams per day, 21 milligrams per day, 22 milligrams per day, 23 milligrams per day, 24 milligrams per day, or 25 milligrams per day.

In some embodiments, a crystalline form of Compound I is administered at a dose of greater than about 5 milligrams per day, greater than about 10 milligrams per day, greater than about 15 milligrams per day, greater than about 20 milligrams per day, greater than about 25 milligrams per day, greater than about 30 milligrams per day, greater than about 35 milligrams per day, greater than about 40 milligrams per day, greater than about 45 milligrams per day, or greater than about 50 milligrams per day. In some embodiments, a crystalline form of Compound I is administered at a dose of less than about 300 milligrams per day, less than about 275 milligrams per day, less than about 250 milligrams per day, less than about 225 milligrams per day, less than about 200 milligrams per day, less than about 175 milligrams per day, less than about 150 milligrams per day, less than about 125 milligrams per day, less than about 100 milligrams per day.

In some embodiments, a crystalline form of Compound I is administered at a dose of about 5 milligrams once daily, about 20 milligrams once daily, about 30 milligrams once daily, about 50 milligrams once daily, about 80 milligrams once daily, about 100 milligrams once daily, about 150 milligrams once daily, about 200 milligrams once daily, about 500 milligrams once daily, about 800 milligrams once daily, or about 1000 milligrams once daily.

In some embodiments, a crystalline form of Compound I is administered at a dose of about 10 milligrams twice daily, about 25 milligrams twice daily, about 50 milligrams twice daily, or about 100 milligrams twice daily.

Pharmaceutical Uses

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "therapeutically effective amount" refers to an amount of the compound as described herein that is sufficient to effect treatment as defined above, when administered to a patient (particularly a human) in need of such treatment in one or more doses. The therapeutically effective amount will vary, depending upon the patient, the disease being treated, the weight and/or age of the patient, the severity of the disease, or the manner of administration as determined by a qualified prescriber or care giver.

Acetyl-CoA carboxylase (ACC) catalyzes the ATP-dependent carboxylation of acetyl-CoA to form malonyl-CoA. This reaction, which proceeds in two half-reactions, a biotin carboxylase (BC) reaction and a carboxyltransferase (CT) reaction, is the first committed step in fatty acid (FA) biosynthesis and is the rate-limiting reaction for the pathway. In addition to its role as a substrate in FA biosynthesis, malonyl-CoA, the product of the ACC-catalyzed reaction, also plays an important regulatory role in controlling mitochondrial FA uptake through allosteric inhibition of carnitine palmitoyltransferase I (CPT-I), the enzyme catalyzing the first committed step in mitochondrial FA oxidation. Malonyl-CoA, therefore, is a key metabolic signal for the control of FA production and utilization in response to dietary changes and altered nutritional requirements in animals, for example during exercise, and therefore plays a key role in controlling the switch between carbohydrate and fat utilization in liver and skeletal muscle (Harwood, 2005).

In mammals, ACC exists as two tissue-specific isozymes, ACC1 which is present in lipogenic tissues (liver, adipose) and ACC2, which is present in oxidative tissues (liver, heart, skeletal muscle). ACC1 and ACC2 are encoded by separate genes, display distinct cellular distributions, and share 75% overall amino acid sequence identity, except for an extension at the N-terminus of ACC2 that direct ACC2 to the mitochondrial membrane. ACC1, which lacks this targeting sequence, is localized to the cytoplasm. In the heart and skeletal muscle, which have a limited capacity to synthesize fatty acids, the malonyl-CoA formed by ACC2 functions to regulate FA oxidation. In the liver, the malonyl-CoA formed in the cytoplasm through the actions of ACC1 is utilized for FA synthesis and elongation leading to triglyceride formation and VLDL production, whereas the malonyl-CoA formed at the mitochondrial surface by ACC2 acts to regulate FA oxidation (Tong and Harwood, *J. Cellular Biochem.* 99: 1476, 2006). This compartmentalization of malonyl-CoA results from a combination of synthesis proximity (Abu-Elheiga et al., PNAS (USA) 102: 12011, 2005) and the rapid action of malonyl-CoA decarboxylase (Cheng et al., *J. Med. Chem.* 49:1517, 2006).

Simultaneous inhibition of the enzymatic activities of ACC1 and ACC2 offers the ability to inhibit de novo FA production in lipogenic tissues (e.g. liver & adipose) while at the same time stimulating FA oxidation in oxidative tissues (e.g. liver & skeletal muscle) and therefore offers an attractive modality for favorably affecting, in a concerted manner, a multitude of cardiovascular risk factors associated with obesity, diabetes, insulin resistance, and the metabolic syndrome.

Several lines of evidence strongly support the concept of direct inhibition of ACC activity as an important therapeutic target for treating obesity, diabetes, insulin resistance, and the metabolic syndrome.

Abu-Elheiga et al. (*Proc. Natl. Acad. Sci. USA* 100: 10207-10212, 2003) demonstrated that ACC2 knock-out mice exhibit reduced skeletal and cardiac muscle malonyl-CoA, increased muscle FA oxidation, reduced hepatic fat, reduced total body fat, elevated skeletal muscle uncoupling protein-3 (UCP3) which is indicative of increased energy expenditure, reduced body weight, reduced plasma free FAs, reduced plasma glucose, and reduced tissue glycogen, and are protected from diet-induced diabetes and obesity.

Savage et al (*J. Clin. Invest.* 116: 817, 2006), using ACC1 and ACC2 antisense oligonucleotides, demonstrated stimulation of FA oxidation in isolated rat hepatocytes and in rats fed high-fat diets, and lowering of hepatic triglycerides, improvements in insulin sensitivity, reductions in hepatic glucose production, and increases in UCP1 mRNA in high fat-fed rats. These effects were greater when both ACC1 and ACC2 expression were suppressed than when either ACC1 or ACC2 expression alone was suppressed.

Harwood et al. (J. Biol. Chem. 278: 37099, 2003) demonstrated that the isozyme-nonselective ACC inhibitor, CP-640186, which equally inhibits ACC1 and ACC2 ($IC_{50}$=~60 nM) isolated from rat, mouse, monkey and human without inhibiting either pyruvate carboxylase or propionyl-CoA carboxylase, reduced FA synthesis, triglyceride synthesis and secretion in Hep-G2 cells without affecting cholesterol synthesis, and reduced apoB secretion without affecting apoA1 secretion. CP-640186 also stimulated FA oxidation in C2C12 cells and in rat muscle slices and increased CPT-I activity in Hep-G2 cells. In experimental animals, CP-640186 acutely reduced malonyl-CoA concentration in both lipogenic and oxidative tissues in both the fed and fasted state, reduced liver and adipose tissue FA synthesis, and increased whole body FA oxidation. In sucrose-fed rats treated with CP-640186 for three weeks, CP-640186 time- and dose-dependently reduced liver, muscle and adipose triglycerides, reduced body weight due to selective fat reduction without reducing lean body mass, reduced leptin levels, reduced the hyperinsulinemia produced by the high sucrose diet without changing plasma glucose levels, and improved insulin sensitivity.

Saha et al. (*Diabetes* 55:A288, 2006) demonstrated stimulation of insulin sensitivity in insulin-resistant rat muscle tissue by CP-640186 within 30 min of compound administration, and studies by Furler et al. (*Diabetes* 55:A333, 2006) used dual tracer analysis to show that acute (46 min) treatment of rats with CP-640186 stimulated FA clearance without decreasing glucose clearance.

ACC is the rate-limiting enzyme in fatty acid synthesis and its product, malonyl CoA, serves as an important regulator of fatty acid oxidation. Hence, ACC inhibitors both reduce de novo lipid synthesis and promote the oxidation of existing fat. This dual effect on lipid metabolism raises the possibility that ACC inhibitors will be substantially more effective in reducing excess fat than other mechanisms. Furthermore, ACC inhibitors will impact insulin sensitivity, plasma and tissue triglycerides, and fasting plasma glucose as a consequence of whole-body and tissue-specific fat mass reduction without the need for poly-pharmacy.

For the treatment of obesity and other metabolic disorders, ACC inhibitors need only access the liver and muscle in the peripheral compartment. For oncological indications, tumor penetration is also required. However, avoiding the CNS will address many of side effects associated with the late-stage obesity programs targeting CNS receptors. ACC inhibitors are also expected to have superior safety profiles to existing metabolic disease agents. For example, it is unlikely that an ACC inhibitor will precipitate life-threatening hypoglycemia as is often seen with insulin mimetics, insulin secretagogues, and insulin degradation inhibitors. Also, since ACC inhibitors will reduce whole-body fat mass, they will be superior to the glitazones that increase whole-body fat mass as part of their mechanism of action.

A peripherally acting agent that causes significant weight loss and improves other metabolic endpoints fits well within the U.S. FDA's requirements for approval of a new obesity agent. However, if an approval for obesity continues to be challenging in 5-7 years, ACC inhibitors could be approved for familial combined hyperlipidemia and non-alcoholic steatohepatitis (NASH). There are currently no marketed ACC inhibitors, so an isozyme-nonselective ACC inhibitor would represent first-in-class therapy for treating obesity and metabolic syndrome, in addition to other disorders mediated by ACC enzymes.

The activity of a provided compound as an inhibitor of ACC or treatment for obesity or metabolic syndrome, may be assayed in vitro or in vivo. An in vivo assessment of the efficacy of the compounds of the disclosure may be made using an animal model of obesity or metabolic syndrome, e.g., a rodent or primate model. Cell-based assays may be performed using, e.g., a cell line isolated from a tissue that expresses ACC. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the disclosure. Alternate in vitro assays quantitate the ability of the inhibitor to bind to protein or nucleic acid molecules within the cell. Inhibitor binding may be measured by radiolabeling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this disclosure as an inhibitor of ACC are set forth in the Examples below. The aforementioned assays are exemplary and not intended to limit the scope of the disclosure. The skilled practitioner can appreciate that modifications can be made to conventional assays to develop equivalent assays that obtain the same result.

A provided compound or composition thereof may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, liver disease, or a cardiac disorder.

In some embodiments, a provided compound or composition thereof may be administered using any amount and any route of administration effective for treating or lessening the severity of a disease associated with ACC (Tong et al. "Acetyl-coenzyme A carboxylase: crucial metabolic enzyme and attractive target for drug discovery" Cell and Molecular Life Sciences (2005) 62, 1784-1803).

In some embodiments, a provided compound or composition thereof may be administered using any amount and any route of administration effective for treating or lessening the severity of a metabolic disorder, disease, or condition. In some embodiments, the metabolic disorder is obesity, metabolic syndrome, diabetes or diabetes-related disorders including Type 1 diabetes (insulin-dependent diabetes mellitus, IDDM) and Type 2 diabetes (non-insulin-dependent diabetes mellitus, NIDDM), impaired glucose tolerance, insulin resistance, hyperglycemia, diabetic complications, including, but not limited to atherosclerosis, coronary heart disease, stroke, peripheral vascular disease, nephropathy, hypertension, neuropathy and nephropathy; obesity comorbidities including but not limited to metabolic syndrome, dyslipidemia, hypertension, insulin resistance, diabetes (including Type 1 and Type 2 diabetes), coronary artery disease, and heart failure. In some embodiments, the metabolic disorder, disease or condition is non-alcoholic fatty liver disease or hepatic insulin resistance. In some embodiments, the metabolic disorder is non-alcoholic steatohepatitis.

Combination Therapy

In some embodiments, the present disclosure provides a method of treating a metabolic disorder, disease, or condition described herein, comprising administering a compound of the disclosure in conjunction with one or more pharmaceutical agents. Suitable pharmaceutical agents that may be used in combination with the compounds of the present disclosure include anti-obesity agents (including appetite suppressants), anti-diabetic agents, anti-hyperglycemic agents, lipid lowering agents, and anti-hypertensive agents.

Suitable lipid lowering agents that can be used in conjunction with a provided compound or composition thereof include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-hypertensive agents that can be used in conjunction with a provided compound or composition thereof include but are not limited to diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, alpha/beta adrenergic blockers, alpha 1 blockers, alpha 2 agonists, aldosterone inhibitors, mineralocorticoid receptor inhibitors, renin inhibitors, and angiopoietin 2 binding agents.

Suitable anti-diabetic agents that can be used in conjunction with a provided compound or composition thereof include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK184072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK-329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-HT$_{2C}$ agonists (e.g. lorcaserin/Belviq), melanin concentrating hormone antagonists, leptin, leptin analogs, leptin agonists, galanin antagonists, lipase inhibitors (e.g. tetrahydrolipstatin/Orlistat), anorectic agents (e.g. bombesin agonists), NPY antagonists (e.g. velneperit), PYY$_{3-36}$ (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide, SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB1 receptor antagonists or inverse agonists, ghrelin agonists or antagonists, oxyntomodulin and analogs thereof, monoamine uptake inhibitors (e.g. tesofensine), and combination agents (e.g. buproprion plus zonisamide (Empatic), pramlintide plus metreleptin, buproprion plus naltrexone (Contrave), phentermine plus topiramate (Qsymia).

In some embodiments, the anti-obesity agents used in combination with a provided compound or composition thereof are selected from gut-selective MTP inhibitors (e.g. dirlotapide, mitratapide, implitapide, R56918), CCK-A agonists, 5-HT$_{2C}$ agonists (e.g. lorcaserin/Belviq), MCR4 agonists, lipase inhibitors (e.g. Cetilistat), PYY$_{3-36}$ (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In some embodiments, a provided compound or composition, according to the method of the present disclosure, may be administered using any amount and any route of administration effective for treating or lessening the severity of a LKB1 or Kras associated disease. In some embodiments, the LKB1 or Kras associated disease is selected from hepatocellular carcinoma, LKB1 mutant cancers, LKB1 loss of heterozygosity (LOH) driven cancers, Kras mutant cancers, Peutz-Jeghers syndrome (PJS), Cowden's disease (CD), and tubeous sclerosis (TS) (Makowski et al. "Role of LKB1 in Lung Cancer Development" British Journal of Cancer (2008) 99, 683-688). In some embodiments, the LKB1 or Kras associated disease is a Kras positive/LKB1 deficient lung tumor.

In some embodiments, a provided compound or composition, according to the method of the present disclosure, may be administered using any amount and any route of administration effective for treating or lessening the severity of a cancer, or inhibiting the growth of or inducing apoptosis in cancer cells (Wang et al. "Acetyl-CoA Carboxylase-alpha Inhibitor TOFA Induces Human Cancer Cell Apoptosis" Biochem Biophys Res Commun. (2009) 385(3), 302-306; Chajes et al. "Acetyl-CoA Carboxylase alpha Is Essential to Breast Cancer Cell Survival" Cancer Res. (2006) 66, 5287-5294; Beckers et al. "Chemical Inhibition of Acetyl-CoA Carboxylase Induces Growth Arrest and Cytotoxicity Selectivity in Cancer Cells" Cancer Res. (2007) 8180-8187; Brusselmans et al. "RNA Interference-Mediated Silencing of the Acetyl-CoA-Carboxylase-alpha Gene Induces Growth Inhibition and Apoptosis of Prostate Cancer Cells" Cancer Res. (2005) 65, 6719-6725; Brunet et al. "BRCA1 and Acetyl-CoA Carboxylase: The Metabolic Syndrom of Breast Cancer" Molecular Carcinogenesis (2008) 47, 157-163; Cairns et al. "Regulation of Cancer Cell Metabolism" (2011) 11, 85-95; Chiaradonna et al. "From Cancer Metabolism to New Biomarkers and Drug Targets" Biotechnology Advances (2012) 30, 30-51).

In some embodiments, a provided compound or composition, according to the method of the present disclosure, may be administered using any amount and any route of administration effective for treating or lessening the severity of a melanoma. In some embodiments, the melanoma is one bearing an activated MAPK pathway (Petti et al. "AMPK activators inhibit the proliferation of human melanomas bearing the activated MAPK pathway" Melanoma Research (2012) 22, 341-350).

A provided compound finds special utility in triple negative breast cancer, as the tumor suppressor protein BRCA1 binds and stabilizes the inactive form of ACC, thus regulating de novo lipid synthesis. Deletion or mutation of this tumor suppressor protein results in the loss of the binding and stabilization of the inactive form of ACC, resulting in increased capacity for ACC-driven de novo lipogenesis, resulting in cancer cell proliferation. See Brunet et al. "BRCA1 and acetyl-CoA carboxylase: the metabolic syndrome of breast cancer" Mol. Carcinog. (2008) 47(2), 157-163.

In some embodiments, a provided compound or composition, according to the method of the present disclosure, may be administered using any amount and any route of administration effective for treating or lessening the severity of a liposarcoma. Liposarcomas have been shown to depend on de novo long-chain fatty acid synthesis for growth, and inhibition of ACC by soraphen A inhibited lipogenesis as well as tumor cell growth (Olsen et al. "Fatty acid synthesis is a therapeutic target in human liposarcoma" International J. of Oncology (2010) 36, 1309-1314).

In some embodiments, a provided compound or composition, according to the method of the present disclosure, may be administered using any amount and any route of administration effective for treating or lessening the severity of a liver disease. In some embodiments, the liver disease is selected from alcoholic fatty liver disease (AFLD), familial combined hyperlipidemia, hepatitis (including hepatitis A, hepatitis B, and hepatitis C), hepatocellular carcinoma, non-alcoholic fatty liver disease (NAFLD), non-alcoholic steatohepatitis (NASH), liver cancer, liver fibrosis, liver inflammation, cholangiocarcinoma, angiosarcoma, hemangiosarcoma, and progressive familial intrahepatic cholestasis. In some embodiments, the liver disease is non-alcoholic steatoheptatitis. In some embodiments, the liver disease is hepatocellular carcinoma.

Some embodiments provided herein provide for methods of treating non-alcoholic steatohepatitis (NASH) comprising administering a therapeutically effective amount of a crystalline form of Compound I as described herein or a composition as described herein.

Some embodiments provided herein provide for the use of a crystalline form of Compound I as described herein or a composition as described herein in the treatment of treating non-alcoholic steatohepatitis (NASH).

Some embodiments provided herein provide for methods of treating hepatocellular carcinoma (HCC) comprising administering a therapeutically effective amount of a crystalline form of Compound I as described herein or a composition as described herein. Some embodiments provided herein provide for the use of a crystalline form of Compound I as described herein or a composition as described herein in the treatment of HCC. In some embodiments, a crystalline form of Compound I is administered as an adjuvant therapy. In some embodiments, the crystalline form of Compound I or composition described herein are administered after curative surgery, local ablation, or liver transplantation.

In some embodiments, a method of treating hepatocellular carcinoma (HCC) comprises administering a therapeutically effective amount of a crystalline form of Compound I as described herein or a composition as described herein in combination with surgical resection, liver transplantation, radiofrequency ablation, percutaneous ethanol injection, transarterial embolization, radiation, or chemotherapy.

In some embodiments, a provided compound or composition, according the method of the present disclosure, may be administered in combination with sorafenib for the treatment of hepatocellular carcinoma.

In some embodiments, a provided compound or composition, according to the method of the present disclosure, may be administered using any amount and any route of administration effective disclosure treating or lessening the severity of a bacterial infection or inhibiting the growth of bacteria. In some embodiments, the bacterial infection is acne vulgaris.

In some embodiments, a provided compound or composition, according to the method of the present disclosure, may be administered using any amount and any route of administration effective for treating or lessening the severity of a fungal infection or inhibiting the growth of fungal cells (Shen et al. "A Mechanism for the Potent Inhibition of Eukaryotic Acetyl-Coenzyme A Carboxylase by Soraphen A, a Macrocyclic Polyketide Natural Product" Molecular Cell (2004) 16, 881-891).

In some embodiments, a provided compound inhibits one or more species of fungi at an MIC of 2 µg/mL or less. In some embodiments, a compound of the present disclosure inhibits at least one of *C. albicans, C. krusei,* and *C. parapsilosis* at a concentration of 2 µg/mL or less. In some embodiments, a compound of the present disclosure inhibits at least one of *C. albicans, C. krusei,* and *C. parapsilosis* at a concentration of 1 µg/mL or less. In some embodiments, a compound of the present disclosure inhibits at least two of *C. albicans, C. krusei,* and *C. parapsilosis* at a concentration of 2 µg/mL or less. In some embodiments, a compound of the present disclosure inhibits at least two of *C. albicans, C. krusei,* and *C. parapsilosis* at a concentration of 1 µg/mL or less. In some embodiments, a compound of the present disclosure inhibits each of *C. albicans, C. krusei,* and *C. parapsilosis* at a concentration of 2 µg/mL or less. In some embodiments, a compound of the present disclosure inhibits each of *C. albicans, C. krusei,* and *C. parapsilosis* at a concentration of 1 µg/mL.

In some embodiments, a provided compound inhibits at least one of Botrtyis *cinerea, Collectotrichum graminicola,* Diplodia *maydis,* Fusarium *moniliforme,* Fusarium *virguliforme,* Phytophthora *capsici, Rhizoctonia solani,* and Septoria at a concentration of 2 µg/mL or less. In some embodiments, a provided compound inhibits at least one of Botrtyis *cinerea, Collectotrichum graminicola,* Diplodia *maydis, Fusarium moniliforme, Fusarium virguliforme, Phytophthora capsici, Rhizoctonia solani,* and *Septoria* at a concentration of 1 µg/mL or less. In some embodiments, a compound of the present disclosure inhibits at least two of Botrtyis *cinerea, Collectotrichum graminicola,* Diplodia *maydis, Fusarium moniliforme, Fusarium virguliforme, Phytophthora capsici, Rhizoctonia solani,* and *Septoria* at a concentration of 2 g/mL or less. In some embodiments, a compound of the present disclosure inhibits at least two of Botrtyis *cinerea, Collectotrichum graminicola,* Diplodia *maydis, Fusarium moniliforme, Fusarium virguliforme, Phytophthora capsici, Rhizoctonia solani,* and *Septoria* at a concentration of 1 µg/mL or less. In some embodiments, a compound of the present disclosure inhibits at least three of Botrtyis *cinerea, Collectotrichum graminicola,* Diplodia *maydis, Fusarium moniliforme, Fusarium virguliforme, Phytophthora capsici, Rhizoctonia solani,* and *Septoria* at a concentration of 2 µg/mL or less. In some embodiments, a compound of the present disclosure inhibits at least three of Botrtyis *cinerea, Collectotrichum graminicola,* Diplodia *maydis, Fusarium moniliforme, Fusarium virguliforme, Phytophthora capsici, Rhizoctonia solani,* and *Septoria* at a concentration of 1 µg/mL or less.

In some embodiments, a provided compound or composition, according to the method of the present disclosure, may be administered using any amount and any route of administration effective for treating or lessening the severity of a bacterial infection (Tong, L. et al. J. Cell. Biochem. (2006) 99, 1476-1488).

In some embodiments, a provided compound or composition, according to the method of the present disclosure, may be administered using any amount and any route of administration effective for treating or lessening the severity of a viral infection (Munger et al. Nat. Biotechnol. (2008) 26, 1179-1186). In some embodiments, the viral infection is Hepatitis C. In some embodiments, the viral infection is Hepatitis B. In some embodiments, the viral infection is Hepatitis A.

In some embodiments, a provided compound or composition, according to the method of the present disclosure, may be administered using any amount and any route of administration effective for treating or lessening the severity of a neurological disease (Henderson et al. Neurotherapeutics (2008) 5, 470-480; Costantini et al. Neurosci. (2008) 9 Suppl. 2:S16; Baranano et al. Curr. Treat. Opin. Neurol. (2008) 10, 410-419).

In some embodiments, a provided compound or composition, according to the method of the present disclosure, may be administered using any amount and any route of administration effective for treating or lessening the severity of a parasitic infection or inhibiting the growth of parasites (e.g. malaria and toxoplasma: Gornicki et al. "Apicoplast fatty acid biosynthesis as a target for medical intervention in apicomplexan parasites" International Journal of Parasitology (2003) 33, 885-896; Zuther et al. "Growth of *Toxoplasma gondii* is inhibited by aryloxyphenoxypropionate herbicides targeting acetyl-CoA carboxylase" PNAS (1999) 96 (23) 13387-13392).

In some embodiments, a provided compound or composition, according to the method of the present disclosure, may be administered using any amount and any route of administration effective for treating or lessening the severity of a cardiac disorder. In some embodiments, the cardiac disorder is cardiac hypertrophy. In some embodiments the cardiac disorder is treated or its severity lessened by the cardioprotective mechanism resulting from increased fatty acid oxidation via ACC inhibition (Kolwicz et al. "Cardiac-specific deletion of acetyl CoA carboxylase 2 (ACC2) prevents metabolic remodeling during pressure-overload hypertrophy" Circ. Res. (2012); DOI: 10.1161/CIRCRESAHA.112.268128).

The exact amount required will vary from subject to subject, depending on the species, age, and general condition of the subject, the severity of the infection, the particular agent, its mode of administration, and the like. A provided compound or composition of the disclosure is preferably formulated in dosage unit form for ease of administration and uniformity of dosage. The expression "dosage unit form" as used herein refers to a physically discrete unit of agent appropriate for the patient to be treated. It will be understood, however, that the total daily usage of a provided compound or composition of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

A pharmaceutically acceptable composition of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, a provided compound of the disclosure may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

A provided compound can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the disclosure relates to a method of inhibiting ACC in a biological sample comprising the step of contacting said biological sample with a provided compound, or a composition comprising said compound.

In certain embodiments, the disclosure relates to a method of modulating fatty acid levels in a biological sample comprising the step of contacting said biological sample with a provided compound, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present disclosure relates to a method of inhibiting ACC in a patient comprising the step of administering to said patient a provided compound, or a composition comprising said compound.

Another embodiment of the present disclosure relates to a method of treating an ACC-mediated disorder comprising administering to a patient in need thereof a therapeutically effective amount of the salt or co-crystal of Compound I as described herein or a pharmaceutical composition as described herein. In some embodiments, a method of treating an ACC-mediated disorder comprises administering to a patient in need thereof a therapeutically effective amount of the salt or co-crystal or crystalline form of Compound I as described herein or a pharmaceutical composition as described herein.

According to another embodiment, the disclosure relates to a method of inhibiting fatty acid production, stimulating fatty acid oxidation, or both, in a patient comprising the step of administering to said patient a provided compound, or a composition comprising said compound. According to certain embodiments, the disclosure relates to a method of inhibiting fatty acid production, stimulating fatty acid oxidation, or both in a patient, leading to decreasing obesity or alleviating symptoms of metabolic syndrome, comprising the step of administering to said patient a provided compound, or a composition comprising said compound. In other embodiments, the present disclosure provides a method for treating a disorder mediated by ACC, in a patient in need thereof, comprising the step of administering to said patient a provided compound or pharmaceutically acceptable composition thereof. Such disorders are described in detail herein.

In some embodiments, a provided compound or composition thereof may be used in a method of treating obesity or another metabolic disorder. In certain embodiments, a provided compound or composition thereof may be used to treat obesity or other metabolic disorder in a mammal. In certain, embodiments the mammal is a human patient. In certain embodiments, a provided compound or composition thereof may be used to treat obesity or other metabolic disorder in a human patient.

In some embodiments, the present disclosure provides a method of treating obesity or another metabolic disorder, comprising administering a provided compound or composition thereof to a patient with obesity or another metabolic disorder. In certain embodiments, the method of treating obesity or another metabolic disorder comprises administering a provided compound or composition thereof to a mammal. In certain embodiments, the mammal is a human. In some embodiments, the metabolic disorder is dyslipidemia or hyperlipidemia. In some embodiments, the obesity is a symptom of Prader-Willi syndrome, Bardet-Biedl syndrome, Cohen syndrome or MOMO syndrome. In some embodiments, the obesity is a side effect of the administration of another medication, including but not limited to insulin, sulfonylureas, thiazolidinediones, antipsychotics, antidepressants, steroids, anticonvulsants (including phenytoin and valproate), pizotifen, or hormonal contraceptives.

In certain embodiments, the present disclosure provides a method of treating cancer or another proliferative disorder, comprising administering a provided compound or composition thereof to a patient with cancer or another proliferative disorder. In certain embodiments, the method of treating cancer or another proliferative disorder comprises administering a provided compound or composition thereof to a mammal. In certain embodiments, the mammal is a human.

As used herein, the terms "inhibition of cancer" and "inhibition of cancer cell proliferation" refer to the inhibition, or decrease in the rate, of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the a provided compound or composition thereof described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by a provided compound or composition thereof is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL). In certain preferred embodiments, the cancer to be treated by a provided compound or composition thereof is one bearing an activated MAPK pathway. In some embodiments, the cancer bearing an activated MAPK pathway is a melanoma. In certain preferred embodiments, the cancer treated by a provided compound or composition thereof is one associated with BRCA1 mutation. In an especially preferred embodiment, the cancer treated by a provided compound or composition thereof is a triple negative breast cancer.

In certain embodiments, the diseases which can be treated by a provided compound or composition thereof are neurological disorders. In some embodiments, the neurological disorder is Alzheimer's Disease, Parkinson's Disease, epilepsy, ischemia, Age Associated Memory Impairment, Mild Cognitive Impairment, Friedreich's Ataxia, GLUT1-deficient epilepsy, Leprechaunism, Rabson-Mendenhall Syndrome, Coronary Arterial Bypass Graft dementia, anaesthesia-induced memory loss, amyotrophic lateral sclerosis, glioma or Huntington's Disease.

In certain embodiments, the disease which can be treated by a provided compound or composition thereof is an infectious disease. In some embodiments, the infectious disease is a viral infection. In some embodiments the viral infection is cytomegalovirus infection or influenza infection. In some embodiments, the infectious disease is a fungal infection. In some embodiments, the infectious disease is a bacterial infection.

Depending upon the particular condition, or disease, to be treated, additional therapeutic agents, which are normally administered to treat that condition, may be administered in combination with a provided compound or composition thereof. As used herein, additional therapeutic agents that are normally administered to treat a particular disease, or condition, are known as "appropriate for the disease, or condition, being treated."

In certain embodiments, a provided compound or composition thereof is administered in combination with one or more additional antifungal (antimycotic) agents for the treatment of a fungal infection. In some embodiments, the one or more additional antifungal (antimycotic) agents are selected from polyene antifungals (including but not limited to amphotericin B (as amphotericin B deoxycholate, amphotericin B lipid complex, or liposomal amphotericin B), candicidin, filipin, hamycin, natamycin, nystatin, and rimocidin), azole antifungals (including but not limited to abafungin, albaconazole, bifonazole, butoconazole, clotrimazole, econazole, efinaconazole, epoxiconazole, fenticonazole, fluconazole, isavuconazole, isoconazole, itraconazole, ketoconazole, luliconazole, miconazole, omoconazole, oxiconazole, posaconazole, propiconazole, ravuconazole, sertaconazole, sulconazole, terconazole, tioconazole, and voriconazole), allylamines (including but not limited to amorolfin, butenafine, naftifine, and terbinafine), echinocandins (including but not limited to anidulafungin, caspofungin, and micafungin), benzoic acid, ciclopirox, flucytosine, griseofulvin, haloprogin, tolnaftate, undecylenic acid, and crystal violet.

In certain embodiments, a provided compound or composition thereof is administered in combination with another inhibitor of ACC or antiobesity agent. In some embodiments, a provided compound or composition thereof is administered in combination with one or more other therapeutic agents. Such therapeutic agents include, but are not limited to agents such as orlistat (Xenical), CNS stimulants, Qsymia, or Belviq.

In certain embodiments, a provided compound or a composition thereof is administered in combination with another anti-cancer, cytotoxin, or chemotherapeutic agent, to a patient in need thereof.

In certain embodiments, the anti-cancer or chemotherapeutic agents used in combination with a provided compound or composition thereof include, but are not limited to, metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane @, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin @, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome @, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte— Colony Stimulating Factor, Granulocyte Macrophage Colony Stimulating Factor, Halotestin®, Herceptin @, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Oxapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, a provided compound or composition may be administered together with a biguanide selected from metformin, phenformin, or buformin, to a patient in need thereof. In certain embodiments, the patient administered a combination of a provided compound and a biguanide is suffering from a cancer, obesity, a liver disease, diabetes or two or more of the above.

In some embodiments, a provided compound or composition may be administered together alone or with one or more additional therapeutic agents for the treatment of acne vulgaris. In some embodiments, the one or more additional therapeutic agents for the treatment of acne vulgaris are selected from topical anti-acne agents (e.g. retinoids, topical antibiotics, benzoyl peroxides), or systemic anti-acne agents (e.g. hormonal therapies, oral antibiotics, isotretinoin). In some embodiments, the hormonal therapy is an oral contraceptive or an androgen blocker. In some embodiments, the oral antibiotic is doxycycline, minocycline, tetracycline, or erythromycin.

In some embodiments, a provided compound or composition may be administered together alone or with one or more additional therapeutic agents for the treatment of seborrhea. In some embodiments, a provided compound or composition may be administered together alone or with one or more additional therapeutic agents for the treatment of seborrheic dermatitis. In some embodiments, a provided compound or composition may be administered together alone or with one or more additional therapeutic agents for the treatment of seborrheic keratosis.

In certain embodiments, a combination of two or more therapeutic agents may be administered together with a provided compound. In certain embodiments, a combination of 3 or more therapeutic agents may be administered with a provided compound.

Other examples of agents the compounds of this disclosure may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, AMPK activators, PCSK9 inhibitors, SREBP site 1 protease inhibitors, HMG CoA-reductase inhibitors, antiemetics (e.g. 5-HT$_3$ receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, a provided compound, or a pharmaceutically acceptable composition thereof, are administered in combination with antisense agents, a monoclonal or polyclonal antibody or a siRNA therapeutic.

In some embodiments, the present disclosure provides a method of treating, stabilizing or lessening the severity or progression of a non-alcoholic fatty liver disease (NAFLD), comprising administering to a patient in need thereof a provided compound, or a pharmaceutically acceptable composition thereof, in combination with one or more additional therapeutic agents. In certain embodiments, the one or more additional therapeutic agents are independently selected from the group consisting of angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacylglycerol O-acyltransferase 1 (DGAT1) inhibitors, dipeptidyl peptidase IV (DPPIV) inhibitors, farnesoid X receptor (FXR) agonists, FXR/TGR5 dual agonists, galectin-3 inhibitors, glucagon-like peptide 1 (GLP1) agonists, glutathione precursors, hepatitis C virus NS3 protease inhibitors, HMG CoA reductase inhibitors, 110 3-hydroxysteroid dehydrogenase (11β-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPARα agonists, PPARγ agonists, PPARδ agonists, Rho associated protein kinase 2 (ROCK2) inhibitors, sodium glucose transporter-2 (SGLT2) inhibitors, stearoyl CoA desaturase-1 inhibitors, thyroid hormone receptor β agonists, tumor necrosis factor α (TNFα) ligand inhibitors, transglutaminase inhibitors, transglutaminase inhibitor precursors, PTP1b inhibitors, and ASK1 inhibitors.

In some embodiments, a provided compound, or a pharmaceutically acceptable composition thereof, is administered in combination with one or more additional therapeutic agents, wherein at least one of the additional therapeutic agents is an angiotensin II receptor antagonist.

In some embodiments, a provided compound, or a pharmaceutically acceptable composition thereof, is administered in combination with one or more additional therapeutic agents, wherein at least one of the additional therapeutic agents is an angiotensin converting enzyme (ACE) inhibitor. In some embodiments, the ACE inhibitor is enalapril.

In some embodiments, a provided compound, or a pharmaceutically acceptable composition thereof, is administered in combination with one or more additional therapeutic agents, wherein at least one of the additional therapeutic agents is a caspase inhibitor. In some embodiments the caspase inhibitor is emricasan.

In some embodiments, a provided compound, or a pharmaceutically acceptable composition thereof, is administered in combination with one or more additional therapeutic agents, wherein at least one of the additional therapeutic agents is a cathepsin B inhibitor. In some embodiments the cathepsin B inhibitor is a mixed cathepsin B/hepatitis C virus NS3 protease inhibitor. In some embodiments, the mixed cathepsin B/hepatitis C virus NS3 protease inhibitor is VBY-376.

In some embodiments, a provided compound, or a pharmaceutically acceptable composition thereof, is administered in combination with one or more additional therapeutic agents, wherein at least one of the additional therapeutic agents is a CCR2 chemokine antagonist. In some embodiments, the additional therapeutic agent is a mixed CCR2/CCR5 chemokine antagonist. In some embodiments, the mixed CCR2/CCR5 chemokine antagonist is cenicriviroc.

In some embodiments, a provided compound, or a pharmaceutically acceptable composition thereof, is administered in combination with one or more additional therapeutic agents, wherein at least one of the additional therapeutic agents is a CCR5 chemokine antagonist.

In some embodiments, a provided compound, or a pharmaceutically acceptable composition thereof, is administered in combination with one or more additional therapeutic agents, wherein at least one of the additional therapeutic agents is a chloride channel stimulator. In some embodiments, the chloride channel stimulator is cobiprostone.

In some embodiments, a provided compound, or a pharmaceutically acceptable composition thereof, is administered in combination with one or more additional therapeutic agents, wherein at least one of the additional therapeutic agents is a cholesterol solubilizer.

In some embodiments, a provided compound, or a pharmaceutically acceptable composition thereof, is administered in combination with one or more additional therapeutic agents, wherein at least one of the additional therapeutic agents is a diacylglycerol O-acyltransferase 1 (DGAT1) inhibitor. In some embodiments, the DGAT1 inhibitor is LCQ908.

In some embodiments, a provided compound, or a pharmaceutically acceptable composition thereof, is administered in combination with one or more additional therapeutic agents, wherein at least one of the additional therapeutic agents is a dipeptidyl peptidase IV (DPPIV) inhibitor. In some embodiments, the DPPIV inhibitor is linagliptin.

In some embodiments, a provided compound, or a pharmaceutically acceptable composition thereof, is administered in combination with one or more additional therapeutic agents, wherein at least one of the additional therapeutic agents is a farnesoid X receptor (FXR) agonist. In some embodiments, the FXR agonist is INT-747 (obeticholic acid). In some embodiments, the FXR agonist is PX-102.

In some embodiments, a provided compound, or a pharmaceutically acceptable composition thereof, is administered in combination with one or more additional therapeutic agents, wherein at least one of the additional therapeutic agents is an FXR/TGR5 dual agonist. In some embodiments, the FXR/TGR5 dual agonist is INT-767.

In some embodiments, a provided compound, or a pharmaceutically acceptable composition thereof, is administered in combination with one or more additional therapeutic agents, wherein at least one of the additional therapeutic agents is a galectin-3 inhibitor. In some embodiments, the galectin-3 inhibitor is GR-MD-02.

In some embodiments, a provided compound, or a pharmaceutically acceptable composition thereof, is administered in combination with one or more additional therapeutic agents, wherein at least one of the additional therapeutic agents is a glucagon-like peptide 1 (GLP1) agonist. In some embodiments, the GLP1 agonist is liraglutide. In some embodiments, the GLP1 agonist is exenatide.

In some embodiments, a provided compound, or a pharmaceutically acceptable composition thereof, is administered in combination with one or more additional therapeutic agents, wherein at least one of the additional therapeutic agents is a glutathione precursor.

In some embodiments, a provided compound, or a pharmaceutically acceptable composition thereof, is administered in combination with one or more additional therapeutic agents, wherein at least one of the additional therapeutic agents is a hepatitis C virus NS3 protease inhibitor. In some embodiments the heptatitis C virus NS3 protease inhibitor is a mixed cathepsin B/hepatitis C virus NS3 protease inhibitor. In some embodiments, the mixed cathepsin B/hepatitis C virus NS3 protease inhibitor is VBY-376.

In some embodiments, a provided compound, or a pharmaceutically acceptable composition thereof, is administered in combination with one or more additional therapeutic agents, wherein at least one of the additional therapeutic agents is an HMG CoA reductase inhibitor. In some embodiments, the HMG-CoA reductase inhibitor is a statin. In some embodiments, the HMG-CoA reductase inhibitor is atorvastatin.

In some embodiments, a provided compound, or a pharmaceutically acceptable composition thereof, is administered in combination with one or more additional therapeutic agents, wherein at least one of the additional therapeutic agents is an 11β-hydroxysteroid dehydrogenase (11β-HSD1) inhibitor. In some embodiments, the 11β-HSD1 inhibitor is RO5093151.

In some embodiments, a provided compound, or a pharmaceutically acceptable composition thereof, is administered in combination with one or more additional therapeutic agents, wherein at least one of the additional therapeutic agents is an IL-11β antagonist.

In some embodiments, a provided compound, or a pharmaceutically acceptable composition thereof, is administered in combination with one or more additional therapeutic agents, wherein at least one of the additional therapeutic agents is an IL-6 antagonist. In some embodiments, the IL-6 antagonist is a mixed IL-6/IL-13/TNFα ligand inhibitor. In some embodiments, the mixed IL-6/IL-1β/TNFα ligand inhibitor is BLX-1002.

In some embodiments, a provided compound, or a pharmaceutically acceptable composition thereof, is administered in combination with one or more additional therapeutic agents, wherein at least one of the additional therapeutic agents is an IL-10 agonist. In some embodiments, the IL-10 agonist is peg-ilodecakin.

In some embodiments, a provided compound, or a pharmaceutically acceptable composition thereof, is administered in combination with one or more additional therapeutic agents, wherein at least one of the additional therapeutic agents is an IL-17 antagonist. In some embodiments, the IL-17 antagonist is KD-025.

In some embodiments, a provided compound, or a pharmaceutically acceptable composition thereof, is administered in combination with one or more additional therapeutic agents, wherein at least one of the additional therapeutic agents is an ileal sodium bile acid cotransporter inhibitor. In some embodiments, the ileal sodium bile acid cotransporter inhibitor is SHP-626.

In some embodiments, a provided compound, or a pharmaceutically acceptable composition thereof, is administered in combination with one or more additional therapeutic agents, wherein at least one of the additional therapeutic agents is a leptin analog. In some embodiments the leptin analog is metreleptin.

In some embodiments, a provided compound, or a pharmaceutically acceptable composition thereof, is administered in combination with one or more additional therapeutic agents, wherein at least one of the additional therapeutic agents is a 5-lipoxygenase inhibitor. In some embodiments, the 5-lipoxygenase inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, a provided compound, or a pharmaceutically acceptable composition thereof, is administered in combination with one or more additional therapeutic agents, wherein at least one of the additional therapeutic agents is a LPL gene stimulator. In some embodiments the LPL gene stimulator is alipogene tiparvovec.

In some embodiments, a provided compound, or a pharmaceutically acceptable composition thereof, is administered in combination with one or more additional therapeutic agents, wherein at least one of the additional therapeutic agents is a lysyl oxidase homolog 2 (LOXL2) inhibitor. In some embodiments, the LOXL2 inhibitor is an anti-LOXL2 antibody. In some embodiments, the anti-LOXL2 antibody is GS-6624.

In some embodiments, a provided compound, or a pharmaceutically acceptable composition thereof, is administered in combination with one or more additional therapeutic agents, wherein at least one of the additional therapeutic agents is a PDE3 inhibitor. In some embodiments, the PDE3 inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, a provided compound, or a pharmaceutically acceptable composition thereof, is administered in combination with one or more additional therapeutic agents, wherein at least one of the additional therapeutic agents is a PDE4 inhibitor. In some embodiments, the PDE4 inhibitor is ASP-9831. In some embodiments, the PDE4 inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, a provided compound, or a pharmaceutically acceptable composition thereof, is administered in combination with one or more additional therapeutic agents, wherein at least one of the additional therapeutic agents is a phospholipase C (PLC) inhibitor. In some embodiments, the PLC inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, a provided compound, or a pharmaceutically acceptable composition thereof, is administered in combination with one or more additional therapeutic agents, wherein at least one of the additional therapeutic agents is a PPARα agonist. In some embodiments the PPARα agonist is a mixed PPARα/δ agonist. In some embodiments, the mixed PPARα/δ agonist is GFT505.

In some embodiments, a provided compound, or a pharmaceutically acceptable composition thereof, is administered in combination with one or more additional therapeutic agents, wherein at least one of the additional therapeutic agents is a PPARγ agonist. In some embodiments, the PPARγ agonist is pioglitazone.

In some embodiments, a provided compound, or a pharmaceutically acceptable composition thereof, is administered in combination with one or more additional therapeutic agents, wherein at least one of the additional therapeutic agents is a PPARδ agonist.

In some embodiments, a provided compound, or a pharmaceutically acceptable composition thereof, is administered in combination with one or more additional therapeutic agents, wherein at least one of the additional therapeutic agents is a Rho associated protein kinase 2 (ROCK2) inhibitor. In some embodiments the ROCK2 inhibitor is KD-025.

In some embodiments, a provided compound, or a pharmaceutically acceptable composition thereof, is administered in combination with one or more additional therapeutic agents, wherein at least one of the additional therapeutic agents is a sodium glucose transporter-2 (SGLT2) inhibitor. In some embodiments, the SGLT2 inhibitor is remogliflozin etabonate.

In some embodiments, a provided compound, or a pharmaceutically acceptable composition thereof, is administered in combination with one or more additional therapeutic agents, wherein at least one of the additional therapeutic agents is a stearoyl CoA desaturase-1 inhibitor. In some embodiments, the stearoyl CoA desaturase-1 inhibitor is aramchol. In some embodiments, the stearoyl CoA desaturase-1 inhibitor is CVT-12805.

In some embodiments, a provided compound, or a pharmaceutically acceptable composition thereof, is administered in combination with one or more additional therapeutic agents, wherein at least one of the additional therapeutic agents is a thyroid hormone receptor β agonist. In some embodiments the thyroid hormone receptor β agonist is MGL-3196.

In some embodiments, a provided compound, or a pharmaceutically acceptable composition thereof, is administered in combination with one or more additional therapeutic agents, wherein at least one of the additional therapeutic agents is a tumor necrosis factor α (TNFα) ligand inhibitor.

In some embodiments, a provided compound, or a pharmaceutically acceptable composition thereof, is administered in combination with one or more additional therapeutic agents, wherein at least one of the additional therapeutic agents is a transglutaminase inhibitor. In some embodiments, the transglutaminase inhibitor precursor is mercaptamine.

In some embodiments, a provided compound, or a pharmaceutically acceptable composition thereof, is administered in combination with one or more additional therapeutic agents, wherein at least one of the additional therapeutic agents is a transglutaminase inhibitor precursor.

In some embodiments, a provided compound, or a pharmaceutically acceptable composition thereof, is administered in combination with one or more additional therapeutic agents, wherein at least one of the additional therapeutic agents is a PTP1b inhibitor. In some embodiments, the PTP1b inhibitor is A119505, A220435, A321842, CPT633, ISIS-404173, JTT-551, MX-7014, MX-7091, MX-7102, NNC-521246, OTX-001, OTX-002, or TTP814.

In some embodiments, a provided compound, or a pharmaceutically acceptable composition thereof, is administered in combination with one or more additional therapeutic agents, wherein at least one of the additional therapeutic agents is an ASK1 inhibitor. In some embodiments, the ASK1 inhibitor is GS-4977 (also known as selonsertib).

In some embodiments, the one or more additional therapeutic agents are independently selected from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, and VBY-376.

In some embodiments, one of the one or more additional therapeutic agents is acetylsalicylic acid. In some embodiments, one of the one or more additional therapeutic agents is alipogene tiparvovec. In some embodiments, one of the one or more additional therapeutic agents is aramchol. In some embodiments, one of the one or more additional therapeutic agents is atorvastatin. In some embodiments, one of the one or more additional therapeutic agents is BLX-1002. In some embodiments, one of the one or more additional therapeutic agents is cenicriviroc. In some embodiments, one of the one or more additional therapeutic agents is cobiprostone. In some embodiments, one of the one or more additional therapeutic agents is colesevelam. In some embodiments, one of the one or more additional therapeutic agents is emricasan. In some embodiments, one of the one or more additional therapeutic agents is enalapril. In some embodiments, one of the one or more additional therapeutic agents is GFT-505. In some embodiments, one of the one or more additional therapeutic agents is GR-MD-02. In some embodiments, one of the one or more additional therapeutic agents is hydrochlorothiazide. In some embodiments, one of the one or more additional therapeutic agents is icosapent ethyl ester (ethyl eicosapentaenoic acid). In some embodiments, one of the one or more additional therapeutic agents is IMM-124E. In some embodiments, one of the one or more additional therapeutic agents is KD-025. In some embodiments, one of the one or more additional therapeutic agents is linagliptin. In some embodiments, one of the one or more additional therapeutic agents is liraglutide. In some embodiments, one of the one or more additional therapeutic agents is mercaptamine. In some embodiments, one of the one or more additional therapeutic agents is MGL-3196. In some embodiments, one of the one or more additional therapeutic agents is obeticholic acid. In some embodiments, one of the one or more additional therapeutic agents is olesoxime. In some embodiments, one of the one or more additional therapeutic agents is peg-ilodecakin. In some embodiments, one of the one or more additional therapeutic agents is pioglitazone. In some embodiments, one of the one or more additional therapeutic agents is PX-102. In some embodiments, one of the one or more additional therapeutic agents is remogliflozin etabonate. In some embodiments, one of the one or more additional therapeutic agents is SHP-626. In some embodiments, one of the one or more additional therapeutic agents is solithromycin. In some embodiments, one of the one or more additional therapeutic agents is tipelukast. In some embodiments, one of the one or more additional therapeutic agents is TRX-318. In some embodiments, one of the one or more additional therapeutic agents is ursodeoxycholic acid. In some embodiments, one of the one or more additional therapeutic agents is and VBY-376.

In some embodiments, at least one of the one or more additional therapeutic agents is an anti-diabetic agent. In some embodiments, the anti-diabetic agent is an adenosine $A_1$ receptor agonist (e.g. adenosine, CCPA, CVT-3619, GR-190718), an adenosine A$_2$ receptor antagonist (istradefylline, SCH-58261), an aldose reductase inhibitor, an α-amylase inhibitor (e.g. tendamistat, treastatin, AL-3688), an α-glucosidase inhibitor (e.g. acarbose, camiglibose, diposine, emiglitate, miglitol, pradimicin-Q, sarbostatin, voglibose), an amylin analog (e.g. AC164209 and pramlintide), an AMPK activator, a β3-adrenergic agonist (e.g. amibegron, AZ-40140, CL-316,243, KRP-204, L-742,791, L-796,568, LY-368,842, LY-377,604, mirabegron, Ro 40-2148, solabegron, SWR-0342SA), a β-ketoacyl-acyl carrier protein synthase inhibitor, a biguanide (e.g. metformin, buformin, phenformin), a carnitine palmitoyl transferase inhibitor, a DGAT-2 inhibitor, a DPP-4 inhibitor (e.g. alogliptin, anagliptin, dutogliptin, gemigliptin, linagliptin, omarigliptin, saxagliptin, sitagliptin, teneligliptin, trelagliptin, and vildagliptin), an ERN1 inhibitor, a fatty acid oxidation inhibitor, a fatty acid synthase (FAS) inhibitor, an FGF21 derivative, a fructose 1,6-diphosphatase inhibitor, a GLP1 agonist (e.g. albiglutide, dulaglutide, exenatide, liraglutide, lixisenatide, taspoglutide), a glucagon receptor modulator, a mixed glucagon receptor/GLP-1 agonist (e.g. MAR-701, ZP2929), a glucokinase inhibitor (e.g. TTP-399, TTP-355, TTP-547, AZD1656, ARRY403, MK-0599, TAK-329, AZD5658, and GKM-001), a glycogen phosphorylase inhibitor (e.g. GSK1362885), a GSK-3 inhibitor, a GPR119 agonist (e.g. MBX-2982, GSK1292263, APD597, PSN821), a GPBAR1 (TGR5) agonist (e.g. INT-777, XL-475), a GPR39 modulator, a GPR40 agonist (e.g. TAK-875), a GPR41 modulator, a GPR43 modulator, a GPR81 modulator, a GPR120 agonist, an HSL inhibitor, an IκB inhibitor, an ILI-beta modulator, insulin or an insulin analog (including, but not limited to, oral, inhaled or injectable formulations thereof), insulin-like growth factor (IGF-1) or an analog thereof, an insulin secretagogue, a JNK inhibitor (e.g. CC-359), a kappa opioid receptor modulator, LY3084077, a Kv1.3 inhibitor (e.g. ChTX, clofazmine, WIN-173173), a MAP4K4 inhibitor, an MC$_1$ or MC$_4$ agonist (e.g. afamelanotide, BMS-470539, bremelanotide, Melanotan II, PF-00446687, PL-6983, setmelanotide, and THIQ), a meglitinide (e.g. repaglinide, nateglinide, mitiglinide), a mineralocorticoid receptor inhibitor, a monoacylglycerol O-acyltransferase inhibitor, an NF-κB inhibitor, a nicotinic acid receptor (HM74A) activator, a PDE-10 inhibitor, a PDHK1 inhibitor, a PDHK4 inhibitor, a PKC (including PKC-alpha, PKC-beta, and PKC-gamma) inhibitor, a PPARα/γ dual agonist, a PTP1b inhibitor (e.g. trodusquemine), a retinol binding protein 4 inhibitor, a serine palmitoyl transferase inhibitor, an SGLT1 inhibitor (e.g. GSK1614235), a SIRT-1 inhibitor (e.g. resveratrol, GSK2245840, GSK184072), a somatostatin receptor inhibitor, a sulfonylurea (e.g. acetohexamide, chlorpropamide, diabinese, glibenclamide, glipizide, glyburide, blimipiride, gliclazide, glipentide, gliquidone, glisolamide, tolazamide, tolbutamide), a thiazolidinedione (e.g. ciglitazone, darglitazone, englitazone, lobeglitazone, MSDC-0602, netoglitazone, pioglitazone, rivoglitazone, rosiglitazone, and troglitazone), a TORC2 inhibitor, a urotensin II receptor agonist, a vasopressin agonist (e.g. DDAVP, WAY-141608), or a VPAC2 receptor agonist.

In some embodiments, at least one of the one or more additional therapeutic agents is an anti-antiobesity agent. In some embodiments, the anti-obesity agent is an apoB-MTP inhibitor (e.g. dirlotapide, JTT130, SLX4090, usistapide), a β3-adrenergic agonist (e.g. amibegron, AZ-40140, CL-316, 243, KRP-204, L-742,791, L-796,568, LY-368,842, LY-377, 604, mirabegron, Ro 40-2148, solabegron, SWR-0342SA), a bombesin receptor agonist, a BRS3 modulator, a CB1 receptor antagonist or inverse agonist, a CCK$_A$ agonist, ciliary neurotrophic factor (CNTF) or analog thereof (e.g. axokine, NT-501), Contrave™ (buproprion/naltrexone), a dopamine receptor agonist (e.g. bromocriptine), an 11β-hydroxysteroid dehydrogenase (11β-HSD1) inhibitor, Empatic™ (pramlintide/metreleptin), a 5-HT$_{2C}$ agonist (e.g. lorcaserin), a galanin antagonist, a ghrelin agonist or antagonist, a GLP1 agonist (e.g. albiglutide, dulaglutide, exenatide, liraglutide, lixisenatide, taspoglutide), a mixed glucagon receptor/GLP-1 agonist (e.g. MAR-701, ZP2929), an H3 antagonist or inverse agonist, a human agouti-related protein (AGRP) inhibitor, leptin or an analog thereof (e.g. metreleptin), a lipase inhibitor (e.g. tetrahydrolipstatin), an MC$_1$ or MC$_4$ agonist (e.g. afamelanotide, BMS-470539, bremelanotide, Melanotan II, PF-00446687, PL-6983, setmelanotide, and THIQ), a melanocyte-stimulating hormone or analog thereof, a MetAp2 inhibitor (e.g. ZGN-433), a monoamine reuptake inhibitor (e.g. buproprion, sibutramine, phentermine, tesofensine), a neuromedin U receptor agonist, an NPY antagonist (e.g. velneperit), an opioid receptor antagonist (e.g. naltrexone), an orexin receptor antagonist (e.g. almorexant, lemborexant, SB-334,867, SB-408,124, SB-649,868, suvorexant), oxyntomodulin or an analog thereof, PYY or an analog thereof (e.g. PYY$_{1-36}$, PYY$_{3-36}$), Qsymia™ (phentermine/topiramate), an RXR-alpha modulator, a stearoyl-CoA desaturase (SCD-1) inhibitor, or a sympathomimetic agent.

In some embodiments, at least one of the one or more additional therapeutic agents is a lipid lowering agent. In some embodiments, the lipid lowering agent is an acyl coenzyme A cholesterol acyl transferase (ACAT) inhibitor, a bile acid reabsorption inhibitor, a cholesterol ester transfer protein (CETP) inhibitor, a 5-LOX inhibitor (e.g. BAY X 1005), a FLAP inhibitor (e.g. AM-679), an HMG CoA synthase inhibitor, a lipoprotein synthesis inhibitor, a low-density lipoprotein receptor inducer, an LXR receptor modulator, a microsomal triglyceride transport inhibitor, niacin, a platelet aggregation inhibitor, a renin-angiotensin system inhibitor, a squalene epoxidase inhibitor, a squalene synthetase inhibitor, or a triglyceride synthesis inhibitor.

In some embodiments, at least one of the one or more additional therapeutic agents is an agent for treating a metabolic disorder. In some embodiments, the agent for treating a metabolic disorder is an ABC transporter activator, ACT-434964 (Actelion), an ANG-5 inhibitor, an angiotensin II antagonist (e.g. MC4262), CCX-872, DUR-928 (Durect), ESP41091, F-652 (Generon), an FGF21 agonist (e.g. BMS-986036), fomepizole (Raptor), an FXR agonist, FXR/TGR5 dual agonist (e.g. INT-767), a ghrelin antagonist (e.g. TZP-301), a glucosylceramide synthase inhibitor, a GPR17 modulator, a GPR119 agonist, IG-MD-014 (Indigene), IMM-124E (Immuron), a lysosome pathway modulator (e.g. CAT5000), a melanin-concentrating hormone receptor 1 antagonist (e.g. KI-1361-17), an MCL1 inhibitor (e.g. CMPX-1023), an mTORC1 inhibitor, an NaCT (e.g. SLC13A5) inhibitor, a NHE3 inhibitor (e.g. RDX-011, tenapanor), NP003 (Neuraltus), PBI-4050 (ProMetic), a proteostasis regulator (e.g. PTI-130, PTI-428, PTI-C1811), PS248288 (Pharmacopeia/Merck), PX-102 (Phenex), RG7410. RG7652, a ROCK inhibitor, SBC-104 (Synageva BioPharma), SPX-100 (Spherix), a stearoyl CoA desaturase inhibitor (e.g. CVT-12805), TRC150094 (Torrent), or ZYH7 (Zydus Cadila).

In some embodiments, at least one of the one or more additional therapeutic agents is an agent for treating steatosis. In some embodiments, the agent for treating steatosis is an adiponectin analog (e.g. PX 811013), aramchol (Galmed), an ASK1 inhibitor (e.g. GS-4977, GS-4997), AZD4076 (AstraZeneca), a bile acid sequestrant (e.g. obeticholic acid), BL-1060 (Galmed), BMS986171 (Bristol-Myers Squibb), a CCR5/CCR2 antagonist (e.g. cenicriviroc), cannabidiol, CER-209 (Cerenis), a cysteamine analog (e.g. RP-103, RP-104), DS102 (DS Biopharma), EGS21 (Enzo), elafibranor (Genfit), emricasan (Idun), ethyl eicosapentaenoic acid (Mochida), an FXR agonist, a GPBAR1 agonist (e.g. RDX009), GR-MD-02 (Galectin Therapeutics), leucine/sildenafil/metformin (NuSirt), LCQ908 (Novartis), LJN452 (Novartis), a LOXL2 inhibitor (e.g. simtuzumab), MAT-8800 (Matinas), MB-10866 (Metabasis), an miR-103/107 inhibitor (e.g. RG-125), MK-4074 (Merck & Co.), nalmefene (TaiwanJ), nivocasan (Gilead), NGM-282 (NGM Biopharmaceuticals), an omega-3 carboxylic acid or mixture of the same (e.g. Epanova™), PX-102 (Phenex), PX-104 (Phenex), remogliflozin etabonate (Kissei), saroglitazar (Zydus-Cadila), SAR-548304 (sanofi-aventis), tipelukast (Kyorin), ursodeoxycholic acid, VK2809 (Viking), or XL335 (Exelixis).

In some embodiments, at least one of the one or more additional therapeutic agents is an agent for treating inflammation. In some embodiments, the agent for treating inflammation reduces the differentiation or activation of $T_h17$ cells. In some embodiments, the agent for treating inflammation is a caspase inhibitor (e.g. emricasan), a TGF-β inhibitor, an IL-1β inhibitor, an IL-6 inhibitor, an IL-17 inhibitor, an IL-17a inhibitor, an IL-17F inhibitor, an IL-21 inhibitor, an IL-23 inhibitor (e.g. guselkumab), IMM-124E, a RORγt inhibitor (e.g. JTE-151) a RORα inhibitor, solithromycin (Cempra), or a vascular adhesion protein-1 inhibitor (e.g. PXS-4728A).

In some embodiments, at least one of the one or more additional therapeutic agents is an agent for treating fibrosis. In some embodiments, the agent for treating fibrosis is cenicriviroc (Tobira/Takeda), CNX-014/023/024/025 (Connexios), an endothelin antagonist (e.g. A192621, ambrisentan, atracentan, bosentan, BQ-123, BQ-788, macitentan, sitaxentan, tezosentan, zibotentan), etanercept, evitar (Ade-Therapeutics), a fibroblast growth factor inhibitor, a galectin-3 inhibitor, imatinib, IVA337 (Inventiva), N-acetylcysteine, nintedanib, pirfenidone, RG6069 (Roche), SP20102 (Sarfez), tipelukast (Kyorin), or XOMA 089 (Xoma).

In some embodiments, the non-alcoholic fatty liver disease is steatosis. In some embodiments, the non-alcoholic fatty liver disease is non-alcoholic steatohepatitis (NASH). In some embodiments, the non-alcoholic fatty liver disease is liver fibrosis caused by NASH. In some embodiments, the non-alcoholic fatty liver disease is liver cirrhosis caused by NASH. In some embodiments, the non-alcoholic fatty liver disease is hepatocellular carcinoma (HCC) caused by NASH.

Those additional agents may be administered separately from a provided compound or composition thereof, as part of a multiple dosage regimen. Alternatively, those agents may be part of a single dosage form, mixed together with a provided compound in a single composition. If administered as part of a multiple dosage regime, the two active agents may be submitted simultaneously, sequentially or within a period of time from one another, normally within five hours from one another.

As used herein, the term "combination," "combined," "in conjunction" and related terms refers to the simultaneous or sequential administration of therapeutic agents in accordance with this disclosure. For example, a provided compound may be administered with another therapeutic agent simultaneously or sequentially in separate unit dosage forms or together in a single unit dosage form. Accordingly, the present disclosure provides a single unit dosage form comprising a provided compound, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this disclosure should be formulated so that a dosage of between 0.01-100 mg/kg body weight/day of a provided compound can be administered.

In those compositions which comprise an additional therapeutic agent, that additional therapeutic agent and a provided compound may act synergistically. Therefore, the amount of additional therapeutic agent in such compositions will be less than that required in a monotherapy utilizing only that therapeutic agent. In such compositions a dosage of between 0.01-100 μg/kg body weight/day of the additional therapeutic agent can be administered.

The amount of additional therapeutic agent present in a composition comprising a provided compound will be no more than the amount that would normally be administered in a composition comprising that therapeutic agent as the only active agent. Preferably the amount of additional therapeutic agent in a provided composition will range from about 50% to 100% of the amount normally present in a composition comprising that agent as the only therapeutically active agent.

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources or prepared as described herein or as known in the art.

XRPD patterns were collected with a PANalytical X'Pert PRO MPD diffractometer using an incident beam of Cu radiation produced using an Optix long, fine-focus source. An elliptically graded multilayer mirror was used to focus Cu Kα (Cu Kα, λ=1.5406 Å) X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

DSC was performed using a TA Instruments 2920 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. Samples were heated from −30° C. to 250° C. at 10° C./min.

TGA analyses were performed using a either a TA Instruments Q5000 thermogravimetric analyzer or TA Instruments Discovery thermogravimetric analyzer. For TGA analyses conducted using a TA Instruments Q5000 thermogravimetric analyzer, temperature calibration was performed using nickel and Alumel™. Each sample was placed in an aluminum pan. The sample was hermetically sealed, the lid pierced, then inserted into the TGA furnace. The furnace was heated under nitrogen. Samples were heated from 25° C. to 350° C. at 10° C./min.

Example 1: Synthesis of Compound B-2

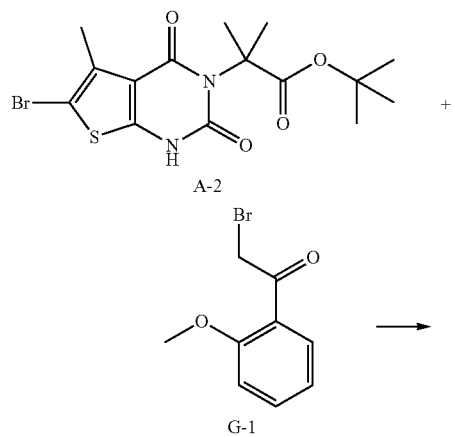

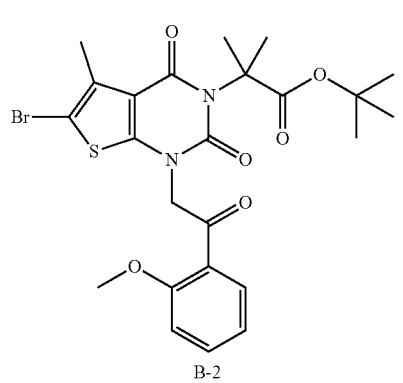

B-2

Compound A-2 was combined with Compound G-1 (about 1 equivalents ("equiv")) with $K_2CO_3$ (about 2.3 equiv) in dimethylacetamide. The mixture was stirred at room temperature. The resulting mixture was then diluted with ethyl acetate and washed with water and brine. The organic layer was separated and concentrated to dryness, and the resulting product was purified by column chromatography (eluent: 0 to about 28% ethyl acetate: heptanes). The resulting product was Compound B-2. $^1$H NMR (300 MHz, CDCl$_3$): δ 7.92 (d, J=8.4 Hz, 1H), 7.57 (m, 1H), 7.06 (m, 2H), 5.20 (s, 2H), 4.00 (s, 3H), 2.42 (s, 3H), 1.77 (s, 6H), 1.44 (s, 9H).

Example 2: Synthesis of a Compound of Formula (C)

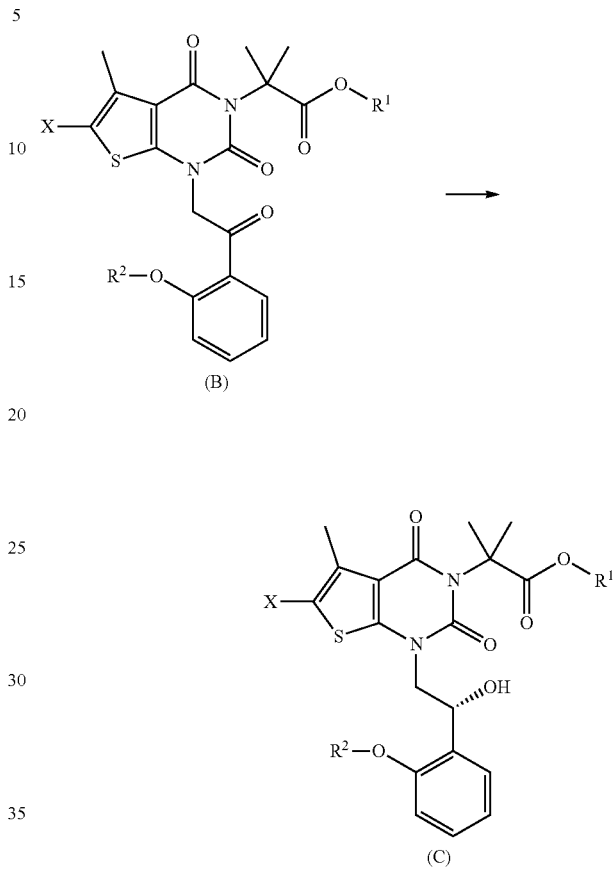

Compound of formula (B) or Compound B (which may be prepared as described in Example 1) and a (S,S)-Ruthenium catalyst, such as a Ruthenium catalyst as described herein, or a suitable antipode of the Ruthenium catalyst, are combined in the presence of potassium tert-butoxide ("KOt-Bu") and isopropanol and refluxed to yield a compound of formula (C) or Compound C. Compound C is isolated and purified by methods described herein.

Example 3: Synthesis of Compound D-1

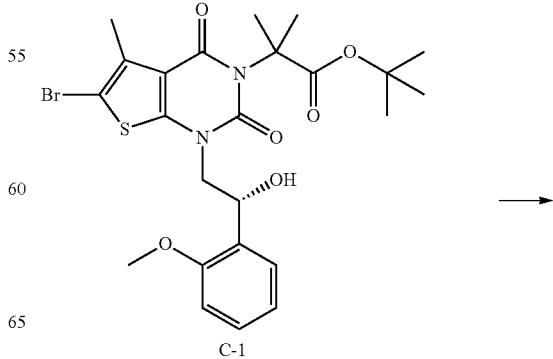

C-1

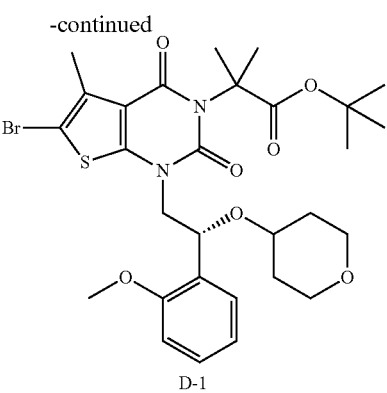

D-1

To Compound C-1 in dichloromethane is added 4-bromotetrahydro-2H-pyran. Upon addition of an organic base, the reaction mixture is stirred overnight to yield a compound of formula D-1 or Compound D-1. Compound D-1 is isolated and purified by the methods described herein.

Example 4: Synthesis of Compound E-2

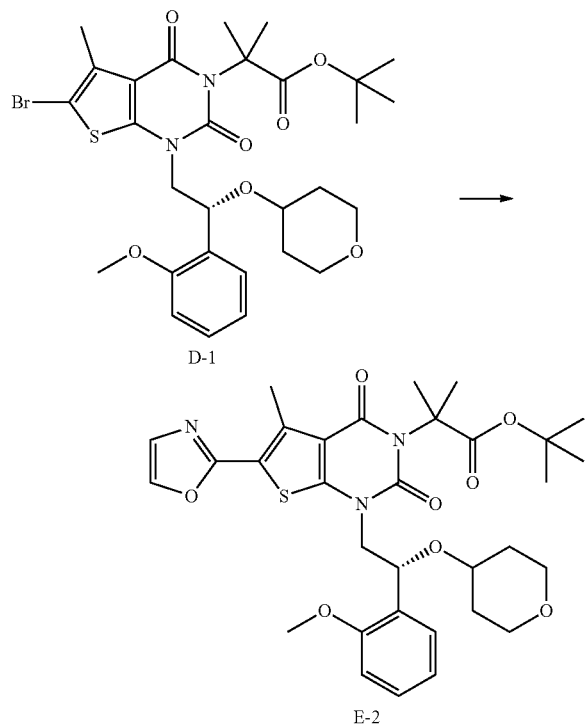

Oxazole in THF is cooled to between about −80° C. and about −60° C. Then, n-butyllithium in hexanes is added while maintaining the temperature of the reaction below about −60° C. The mixture is stirred at this temperature for 90 minutes. Zinc (II) chloride is added, maintaining the temperature of the mixture below about −60° C., and the mixture is stirred at that temperature for about one hour before warming to about 10-20° C. Compound D-1 is added to the reactor followed by tetrakis(triphenylphosphine)palladium(0) ("Pd(PPh$_3$)$_4$"), and the temperature is adjusted to between about 55-65° C. The mixture is stirred at that temperature for about 12 hours to yield Compound E-2. Compound E-2 is isolated and purified by the methods described herein.

Example 5: Synthesis of Compound I

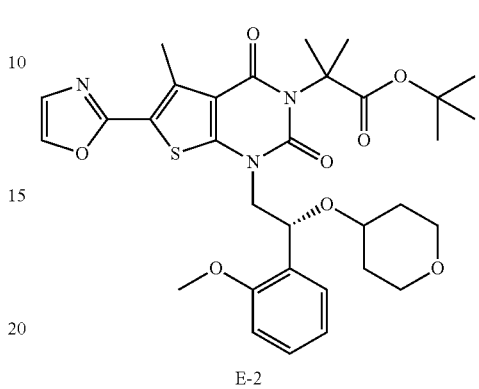

E-2

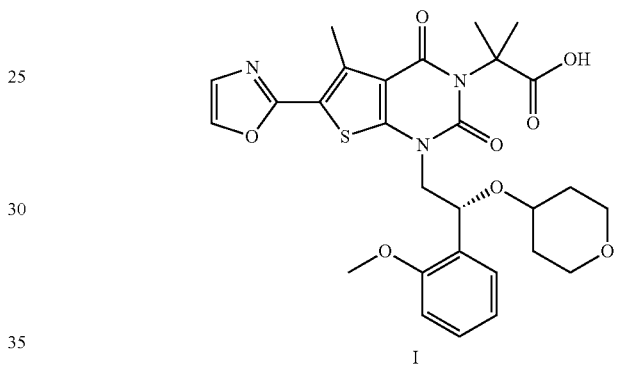

I

A sulfuric acid solution was prepared by addition of concentrated sulfuric acid (47 g, 4.7 w/w Compound E-2) to water (12 g, 1.2 v/w Compound E-2) followed by a water (15 g, 1.5 v/w Compound E-2) rinse forward. 2-Propanol (37 g, 4.7 v/w Compound E-2) was slowly charged to a reactor containing sulfuric acid solution at about 9° C. while maintaining the reaction contents at no more than about 40° C., and the solution was cooled to about 5° C. Compound E-2 (10 g, 1.0 equiv) was charged to the solution, followed by a 2-propanol rinse forward (2 g, 0.25 v/w E-2). The contents were cooled to about 7° C. and stirred for a minimum of about 21 hours. The contents were slowly added into water, and the slurry was agitated for about 30 minutes. The slurry was filtered, and the filter cake was washed and dried under vacuum for about 4 hours. The crude wet cake was charged back to the reactor, followed by additions of ethyl acetate (40 g, 4.4 v/w Compound E-2) and water (100 g, 10 v/w Compound E-2). The slurry was adjusted to pH at about 8-9 with an about 20 wt % sodium hydroxide solution at about 22° C., and then agitated for about 30 minutes at about 22° C. The solution was allowed to settle. The top organic layer was collected and the bottom aqueous layer was washed with ethyl acetate (40 g, 4.4 v/w Compound E-2) at about 22° C. for about 30 minutes. The solution was allowed to settle, and the top organic layer was removed. 2-Methyltetrahydrofuran (86 g, 10 v/w Compound E-2) was then added, was adjusted to pH at about 4-5 with an about 4 N HCl solution at about 22° C. The solution was agitated for about 30 minutes at about 22° C. and then allowed to settle. The bottom aqueous layer was extracted with 2-methyltetrahydrofuran (52 g, 6 v/w Compound E-2) at about 22° C. for about 30 minutes. After the solution was allowed to settle, the bottom aqueous layer was removed. The organic layers were combined and distilled under vacuum (jacket at about <45° C.) to about 4V pot volume. Ethanol (55.4 g, 7 v/w Compound E-2) was added and the reaction as distilled (repeated twice). Ethanol was again added (23.7 g, 3 v/w Compound E-2), followed by water (30 g, 3 v/w Compound E-2). The reaction was heated to about 75° C. and then cooled over about 4 hours to about 50° C., then to about 0° C. over about 5 hours. The reaction was then aged and filtered, and the solid was washed with a precooled mixture of ethanol (9.5 g, 1.2 v/w Compound E-2) and water (6 g, 0.6 v/w Compound E-2). The resulting product was washed to afford Compound of formula (I). $^1$H NMR (400 MHz, CDCl$_3$): δ 7.70 (s, 1H), 7.57 (dd, J=1.6 Hz, J=7.6 Hz, 1H), 7.29 (td, J=1.6 Hz, J=8.0 Hz, 1H), 7.23 (d, J=0.4 Hz, 1H), 7.02 (t, J=7.6 Hz, 1H), 6.86 (d, J=8.4 Hz, 1H), 5.39 (dd, J=5.6 Hz, J=8.0 Hz, 1H), 4.17-4.14 (m, 1H), 4.04 (br, 1H), 3.86 (s, 3H), 3.78-3.67 (m, 2H), 3.46-3.40 (m, 1H), 3.37-3.32 (m, 2H), 2.85 (s, 3H), 1.87 (s, 3H), 1.83 (s, 3H), 1.75-1.72 (m, 2H), 1.59-1.51 (m, 1H), 1.48-1.39 (m, 1H).

Example 6: Synthesis of Compound J-1

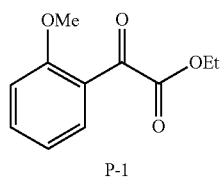

2-Methoxyphenylmagnesium bromide (1M in THF, 1.0 equiv.) was added to a solution of diethyl oxalate (1.1 equiv.) in THF (250 mL) at about −20° C. over approximately 20 min. After aging for about 45 min at about −20° C., the resulting slurry was quenched with saturated NH$_4$Cl (250 mL) and was diluted with water (200 mL). This mixture was extracted with EtOAc (400 mL), and the organic phase was washed with brine (200 mL). The organic phase was concentrated and the solvent was exchanged to THF. The resulting THF solution was used in the next step as is. $^1$H NMR (400 MHz, CDCl$_3$): δ 7.90 (m, 1H), 7.61 (m, 1H), 7.10 (t, J=7.6 Hz, 1H), 7.01 (d, J=8.4 Hz 1H), 4.41 (q, J=7.1 Hz, 2H), 3.88 (s, 3H), 1.41 (t, J=7.1 Hz, 3H).

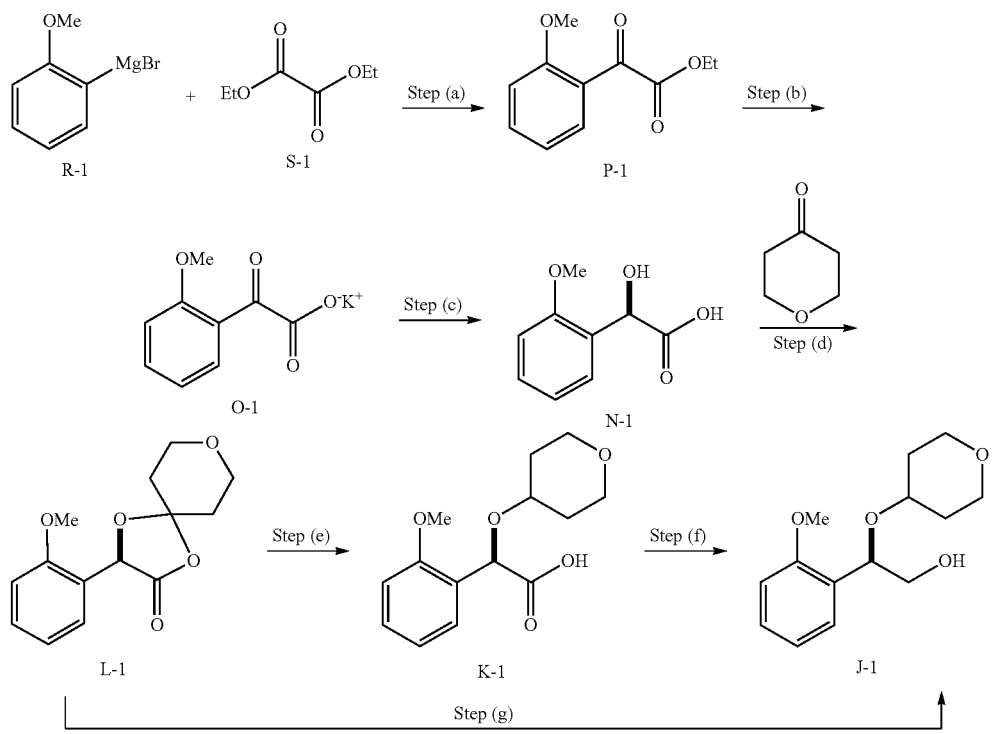

Step (a): Formation of Compound P-1:

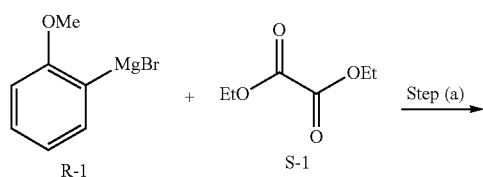

Alternate Preparation Compound P-1:

Anisole (1.0 equiv.) in THF (15 mL) was cooled to about −20° C., and 2.5M n-BuLi/hexane (1.1 equiv.) was added. The mixture was allowed to warm to about 0° C. and aged for about 2 hours, then warmed to room temperature overnight. The solution was then added to a solution of diethyl oxalate (4.0 equiv.) in THF (10 mL) at about −20° C. The mixture was allowed to warm to about room temperature and aged for approximately 2 hours, then cooled to about 0° C. and quenched via addition of saturated NH$_4$Cl (30 mL). This mixture was extracted with EtOAc, and the organic phase was washed with brine and dried over MgSO$_4$.

Concentration afforded Compound P-1.

Alternate Preparation Compound P-1:

2-Bromoanisole (1.0 equiv.) in THF (63 mL) was cooled to about −65° C. and 2.5M n-BuLi/hexanes (1.0 equiv) was added. After aging for approximately 1 h, diethyl oxalate (4.0 equiv.) was charged, and the reaction mixture was allowed to warm to about room temperature. After approximately 1 h at about room temperature, the reaction mixture was cooled to about 0° C., quenched by addition of saturated NH₄Cl (50 mL), and diluted with EtOAc. The aqueous phase was separated and was extracted with EtOAc. The combined organic phases were washed with brine and dried over MgSO₄. Concentration under high vacuum afforded a product that was passed through a plug of silica gel to afford Compound P-1.

Step (b): Hydrolysis of Compound P-1 and Salt Conversion to Compound O-1:

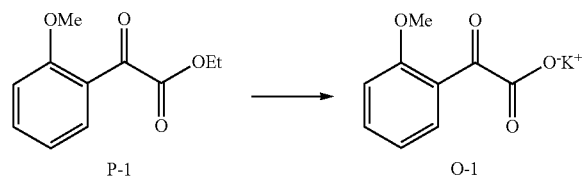

The resulting solution of ketoester, compound P-1, in THF (about 1.0 equiv.) was cooled over an ice bath and 2N NaOH (1.36 equiv.) was added. The reaction was agitated at about 0° C. and after reaction completion, the reaction was then acidified by addition of 6N HCl (57 mL) to about pH <1 and extracted with EtOAc (500 mL). The organic phase was washed with brine (200 mL). The organic phase was concentrated and then solvent exchanged to EtOAc. The resulting solution was cooled to about 0° C. and solid KOᵗBu (1.0 equiv.). The slurry was agitated for approximately 4 h and the solids were filtered, rinsed with EtOAc, and dried overnight at about 60° C. under vacuum to afford Compound O-1. ¹H NMR (400 MHz, DMSO-d6): δ 7.61 (d, J=7.6 Hz, 1H), 7.49-7.41 (m, 1H), 7.04 (d, J=8.4 Hz 1H), 6.96 (t, J=7.4 Hz, 1H), 3.73 (s, 3H).

Step (c): Reduction of Compound O-1 to Compound N-1:

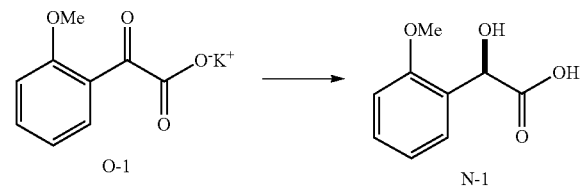

To triethylamine (3.6 equiv.) precooled to about 0° C., was added formic acid (9.0 equiv.) over about 30 min while maintaining a temperature less than about 30° C. Solid RuCl (R,R)-Ts-DENEB catalyst (0.07 mol %) followed by ketoacid potassium salt (1.0 equiv.) were then charged to the mixture of triethylamine/formic acid. The resulting slurry was warmed to about 50° C. and was stirred under nitrogen until the reaction was complete. The reaction was cooled over an ice bath and quenched by the addition of water (76 mL) followed by 10ON NaOH (128 mL) to pH >13. Water (30 mL) and iPrAc (130 mL) were added and the organic layer was separated, and the aqueous phase was extracted with iPrAc (2×130 mL). The aqueous phase was cooled and was acidified with concentrated HCl. This was extracted with iPrAc several times and the combined organic extract was concentrated and solvent exchanged to toluene, filtered hot, and then cooled to about 30° C. over approximately 2 h, aged for approximately 1 h, then filtered to afford solids that were then slurry-rinsed with toluene (50 mL) at room temperature and filtered. The wet cake was dried to afford Compound N-1. ¹H NMR (400 MHz, CDCl₃): δ 7.44 (d, J=7.6 Hz, 1H), 7.40-7.36 (m, 1H), 7.06 (t, J=7.6 Hz 1H), 6.98 (d, J=8.4 Hz, 1H), 5.41 (s, 1H), 3.94 (s, 3H).

Step (d): Spiroketalization to Afford Compound L-1:

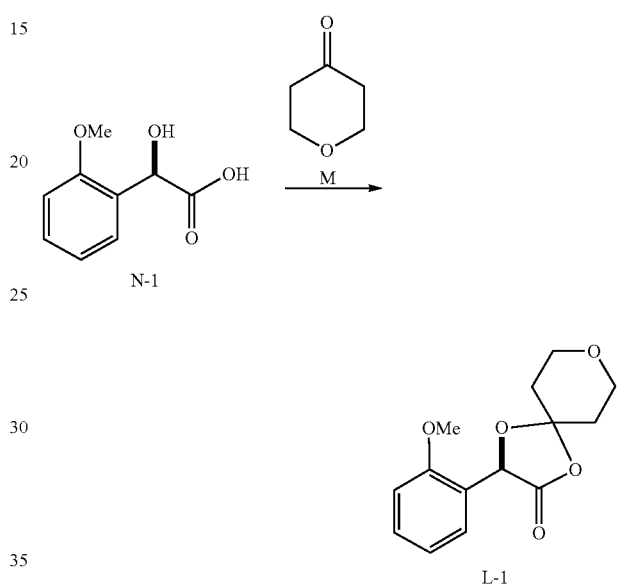

Compound N-1 (1.0 equiv.), tetrahydropyran-4-one (compound M, 1.1 equiv.), and MTBE (30 mL) were sequentially charged and cooled to about 0° C. Boron trifluoride THF complex (1.4 equiv.) was added over about 10 mins. After reaction completion, the reaction was slowly quenched with a pre-mixed solution of sodium bicarbonate (3.66 g) and water (40 mL). The solution was warmed to about 20° C. and diluted with toluene (40 mL) and stirred until dissolved. Agitation was stopped and the aqueous layer removed. The organic layer was washed with water (20 mL) and removed. The organic layer was collected and reactor rinsed forward with toluene (4 mL) to yield Compound L-1. ¹H NMR (400 MHz, CDCl₃): δ 7.42-7.38 (m, 1H), 7.32 (dd, J=7.5, 1.5 Hz, 1H), 7.03 (t, J=7.5 Hz, 1H), 6.98 (d, J=8.3 Hz, 1H), 5.52 (s, 1H), 3.97-3.79 (m, 7H), 2.18-1.97 (m, 4H).

Step (e): Reduction of Compound L-1 to Compound K-1:

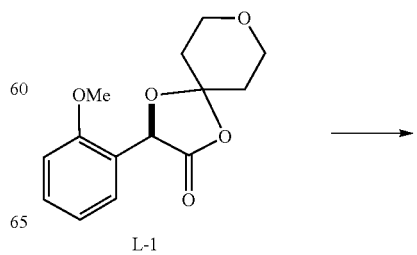

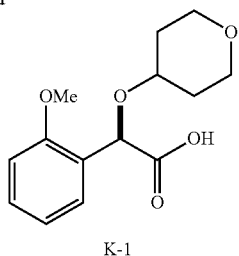

K-1

A stock solution of spiroketal, compound L-1, in MeTHF/MTBE (1.0 equiv.) was charged to a reactor. The solution was then distilled to about 4 volumes. MeTHF (187 mL) was charged, and distilled down to about 5 volumes. The solution was cooled to about 20° C. DCM (90 mL) was charged and the solution was cooled to about 10° C. and tert-butyl magnesium chloride (2M in diethyl ether) (5.0 equiv.) was added over approximately 45 mins. Following addition, the contents were cooled to about 7° C. and aged overnight at about 10° C., then to about 0° C. A premixed solution of HCl (45 mL) and water (126 mL) was then slowly added. The aqueous bottom layer was drained and the aqueous layer extracted with MeTHF (93 mL). The combined organic layers were washed with water (37 mL) and the remaining organic layer was distilled down to about 4 volumes. Isopropyl acetate (181 mL) was charged and the solution reduced to about 5 volumes. The reaction was cooled to about 72° C. and heptanes (58 mL) was charged and the solution was held for about 1 hour before cooling to about 0° C. over approximately 5 hours. The slurry was agitated at about 0° C. for >12 h and then filtered, rinsed with an isopropyl acetate (9 mL) and heptanes (18 mL) mixture, followed by water (54 mL). The solids were dried to yield compound K-1. $^1$H NMR (400 MHz, CDCl$_3$): δ 8.49 (br. s, 1H), 7.42-7.29 (m, 2H), 6.98 (t, J=7.4 Hz, 1H), 6.92 (d, 8.3 Hz, 1H), 5.43 (s, 1H), 3.96 (dt, J=11.5, 4.3 Hz, 1H), 3.89 (dt, J=11.5, 4.3 Hz, 1H), 3.85 (s, 3H), 3.67-3.58 (m, 1H), 3.47-3.30 (m, 2H), 2.03-1.93 (m, 1H), 1.84-1.75 (m, 1H), 1.75-1.56 (m, 2H).

Step (f): Reduction of Compound K-1 to Compound J-1:

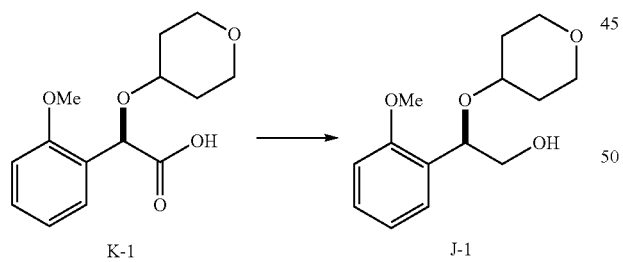

A solution of acid, compound K-1 (1.0 equiv.), in THF (90 mL) was cooled to about 0° C. and NaBH$_4$ (1.2 equiv.) was added followed by BF$_3$-THF complex (1.5 equiv.). The solution was warmed to about 20° C. and agitated until the reaction was deemed complete. Upon completion, MeOH (24 mL) was added to the reaction mixture after adjusting the temperature to about 5° C., and was stirred until the gas evolution ceased. EtOAc (102 mL) was charged followed by saturated NH$_4$Cl$_{aq}$ solution (87 mL). The agitation was stopped and the aqueous layer was removed. The organic layer was distilled down to about 3 volumes under vacuum, and then heptane (46 mL) was charged. The resulting mixture was cooled to about 0° C. and agitated at this temperature for approximately 4 h before being filtered and rinsed with heptane (3 mL). The resulting solids were dried to yield compound J-1. $^1$H NMR (400 MHz, CDCl$_3$): δ 7.42 (d, J=7.2 Hz, 1H), 7.27 (m, 1H), 6.98 (m, 1H), 6.87 (d, J=8.4 Hz, 1H), 5.06 (dd, J=8.4, 2.8 Hz, 1H), 3.93 (m, 2H), 3.82 (s, 3H), 3.67 (m, 1H), 3.55-3.46 (m, 2H), 3.41-3.32 (m, 2H), 2.27 (d, J=8.0 Hz, 1H), 2.01 (m, 1H), 1.80-1.70 (m, 1H), 1.65 (m, 2H).

Step (g): Alternate Direct Reduction of Compound L-1 to Compound J-1:

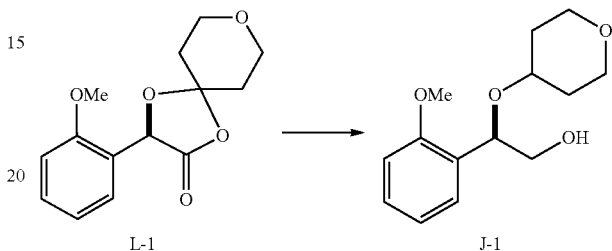

To a solution of ketal, compound L-1 (1 equiv.), in diglyme (0.7 mL) was added NaBH$_4$ (3.6 equiv.) followed by BF$_3$-THF complex (4.5 equiv.). Reaction mixture was agitated for about 18 hours and was quenched by dropwise addition of MeOH (1 mL) followed by saturated NH$_4$Cl$_{aq}$ solution (1 mL). EtOAc (2 mL) was added, shaken well and the aqueous layer was removed. Organic solvent was removed under reduced pressure to obtain the crude compound J-1.

Example 7: Alternate Synthesis to Compound N-1

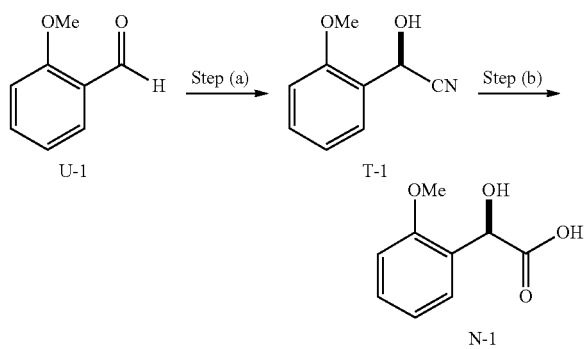

Step (a): Addition of Hydrogen Cyanide to Ortho-Anisaldehyde, Compound U-1, to Form Compound T-1

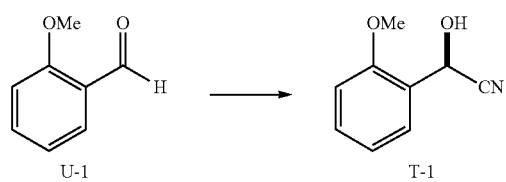

To an Eppendorf tube was added ortho-anisaldehyde, compound U-1 (1.0 equiv), followed by 0.4M sodium acetate buffer pH 5 (0.25 mL) and tert-butyl methyl ether (0.75 mL). The mixture was shaken using a thermomixer at about 30° C. and about 1200 rpm to ensure complete dissolution of the aldehyde. Once this was complete acetone cyanohydrin (1.15 equiv) is added to the reaction mixture followed by hydroxynitrilase enzyme (2 mg). The Eppendorf tube was shaken in a thermomixer at about 30° C. and about 1200 rpm overnight. The Eppendorf tube was then heated to about 60° C. at about 1400 rpm for about 15 mins in order to denature the enzyme before being cooled to about 30° C. The Eppendorf tube was then centrifuged at about 13,400 rpm for about 15 mins in order to pellet the denatured enzyme from the organic layer. The organic layer was removed and concentrated to dryness to give crude compound T-1. ¹H NMR (400 MHz, CDCl₃): δ 7.45-7.39 (m, 2H), 7.04-6.96 (m, 2H), 5.63 (s 1H), 3.94 (s, 3H), 3.75 (br, 1H).

Step (b): Hydrolysis of Compound T-1 to Form Compound N-1:

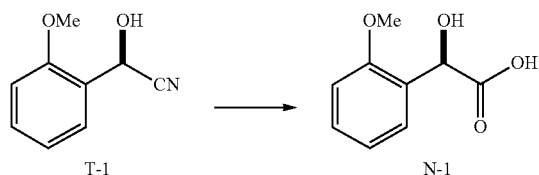

Before starting the reaction the following stock solutions were prepared: A solution of the crude cyanohydrin (compound T-1) in DMSO (about 100 mg/mL); a solution of 50 mM potassium phosphate (pH 7) containing 2 mM dithiothreitol (DTT); and 1 mM ethylenediamine tetraacetic acid (EDTA). To an Eppendorf tube was added nitrilase enzyme (4 mg) followed by 1.1 mL of the reaction buffer solution and 0.05 mL of the solution containing the crude cyanohydrin (about 10 mg). The Eppendorf tube was shaken in a thermomixer at about 30° C. and about 1200 rpm overnight. The Eppendorf tube was then heated to about 60° C. at about 1400 rpm for about 15 mins in order to denature the enzyme before being cooled to about 30° C. once more. The Eppendorf tube was centrifuged at about 13,400 rpm for about 15 mins in order to pellet the denatured enzyme and then separate it from the supernatant. The supernatant was either sampled directly for reverse phase UPLC or extracted with DCM for normal phase HPLC. In the case of DCM extraction, after separating the layers the organic layer was concentrated to dryness before the appropriate diluent was added for normal phase HPLC. UPLC analysis showed a peak with retention time identical to a reference standard of compound N-1.

Example 8: Alternate Synthesis to Compound N-1

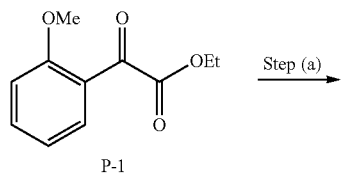

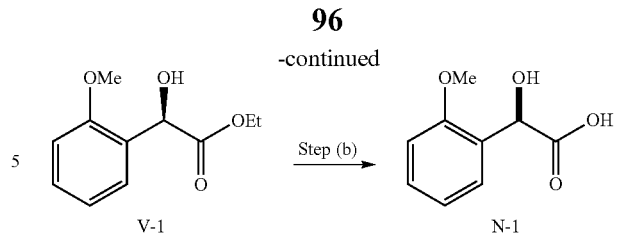

Step (a): Reduction of Compound P-1 to Form 2'-Methoxy-Ethyl Mandelate, Compound V-1:

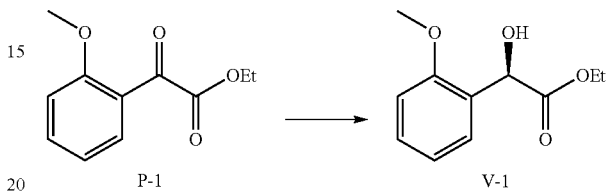

The following stock solutions were made prior to the start of the reaction: a solution of starting material in DMSO (about 100 mg/mL), NADP⁺ or NAD⁺ in 0.1M phosphate buffer (as appropriate) (2 mg/mL), glucose dehydrogenase in 0.1M phosphate buffer (4 mg/mL), and glucose in 0.1M phosphate buffer (20 mg/mL). To an Eppendorf tube is charged the ketoreductase enzyme (2 mg) followed by 0.25 mL of buffer solution containing NAD(P)⁺, 0.25 mL of buffer solution containing glucose dehydrogenase (GDH) and 0.5 mL of buffer solution containing glucose. Finally, 0.05 mL of the stock solution containing the starting material, compound P-1 in DMSO is added. The Eppendorf tube was then shaken in a thermomixer at about 30° C. and about 1200 rpm overnight. The Eppendorf tube was then heated to about 60° C. at about 1400 rpm for about 15 mins in order to denature the enzymes before being cooled to about 30° C. The Eppendorf tube was then centrifuged at about 13,400 rpm for about 15 mins in order to pellet the denatured enzyme and the supernatant removed. This was either sampled directly for reverse phase UPLC or extracted with DCM for normal phase HPLC. In the case of DCM extraction after separating the layers the organic layer was concentrated to dryness before the appropriate diluent was added for normal phase HPLC. UPLC analysis showed a peak with retention time identical to a reference standard of the product material.

Step (b) Hydrolysis of 2'-Methoxy-Ethyl Mandelate, Compound V-1, to Provide Compound N-1:

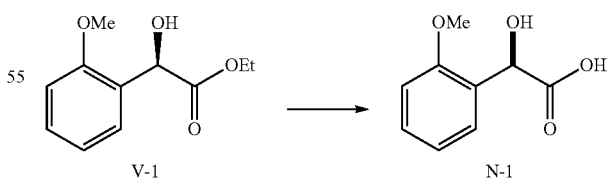

A solution of 2'-methoxy-ethyl mandelate (1.0 equiv.) in EtOH (30 mL) was cooled to about 0° C. and 1.25M NaOH (30 mL) was slowly added. Upon reaction completion, the reaction was adjusted to about pH 1 with 1M HCl (40 mL). The mixture was extracted three times with ethyl acetate (30 mL) and the combined organics were washed with a brine solution (25 mL). The combined organic layers were dried over sodium sulfate, filtered, and the solvent removed under vacuum to provide the product. NMR data reported as above.

Example 9: Compound I Choline Form I

The choline salt/cocrystal (solvate) of Compound I ("Compound I Choline Form I") was obtained by precipitation when 100 μL ethyl acetate ("EtOAc") was added to 51.2 mg of Compound I (prepared as described in U.S. Patent Publication No. 2017/0267690, titled "Solid Forms of a Thienopyrimidinedione ACC Inhibitor and Methods for Production Thereof," filed on Mar. 1, 2017, which is hereby incorporated by reference in its entirety), followed by the addition of 49 μL choline hydroxide (in methanol). An additional 100 μL of EtOAc was added to the suspension whereby it was stirred at room temperature for about 1.5 hours.

Figure 3:
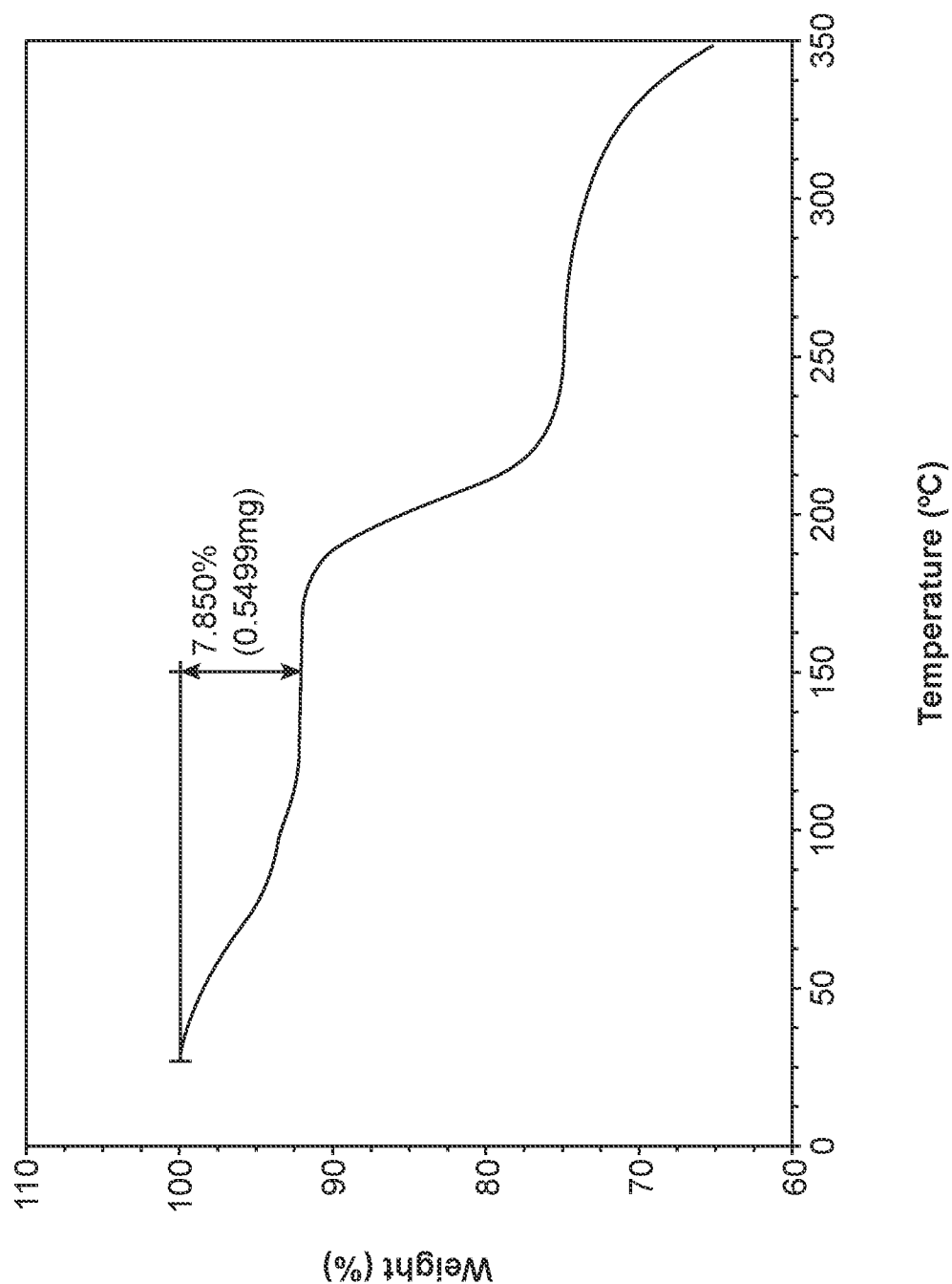
FIG. 3 shows a thermogravimetric analysis (TGA) of Compound I Choline Form I.

The XRPD pattern of the resulting product, Compound I Choline Form I, is shown in FIG. 1. The DSC curve is shown in FIG. 2 and indicates multiple endothermic transitions with onsets at about 73° C. and about 195° C. The TGA curve is shown in FIG. 3 and displays a weight loss (about 7.9% room temperature to 150° C.) attributed to loss of volatiles. $^1$H NMR data suggests Compound I Choline Form I is a Compound I:choline phase of a 1:1 ratio.

Example 10: Compound I Diethylamine Form I

The diethylamine salt/cocrystal (hemi-acetonitrile solvate) of Compound I ("Compound I Diethylamine Form I") was obtained when 1 mL of acetonitrile was added to 75.8 mg of Compound I (prepared as described in U.S. Patent Publication No. 2017/0267690, titled "Solid Forms of a Thienopyrimidinedione ACC Inhibitor and Methods for Production Thereof," filed on Mar. 1, 2017, which is hereby incorporated by reference in its entirety), followed by 1 mL of EtOAc and heating the mixture to about 70° C. to yield a solution. 41 μL of diethylamine was then added and the solution was cooled to room temperature followed by evaporation of the mother liquors at room temperature. The XRPD pattern of the resulting product, Compound I Diethylamine Form I, is shown in FIG. 4.

Figure 5:
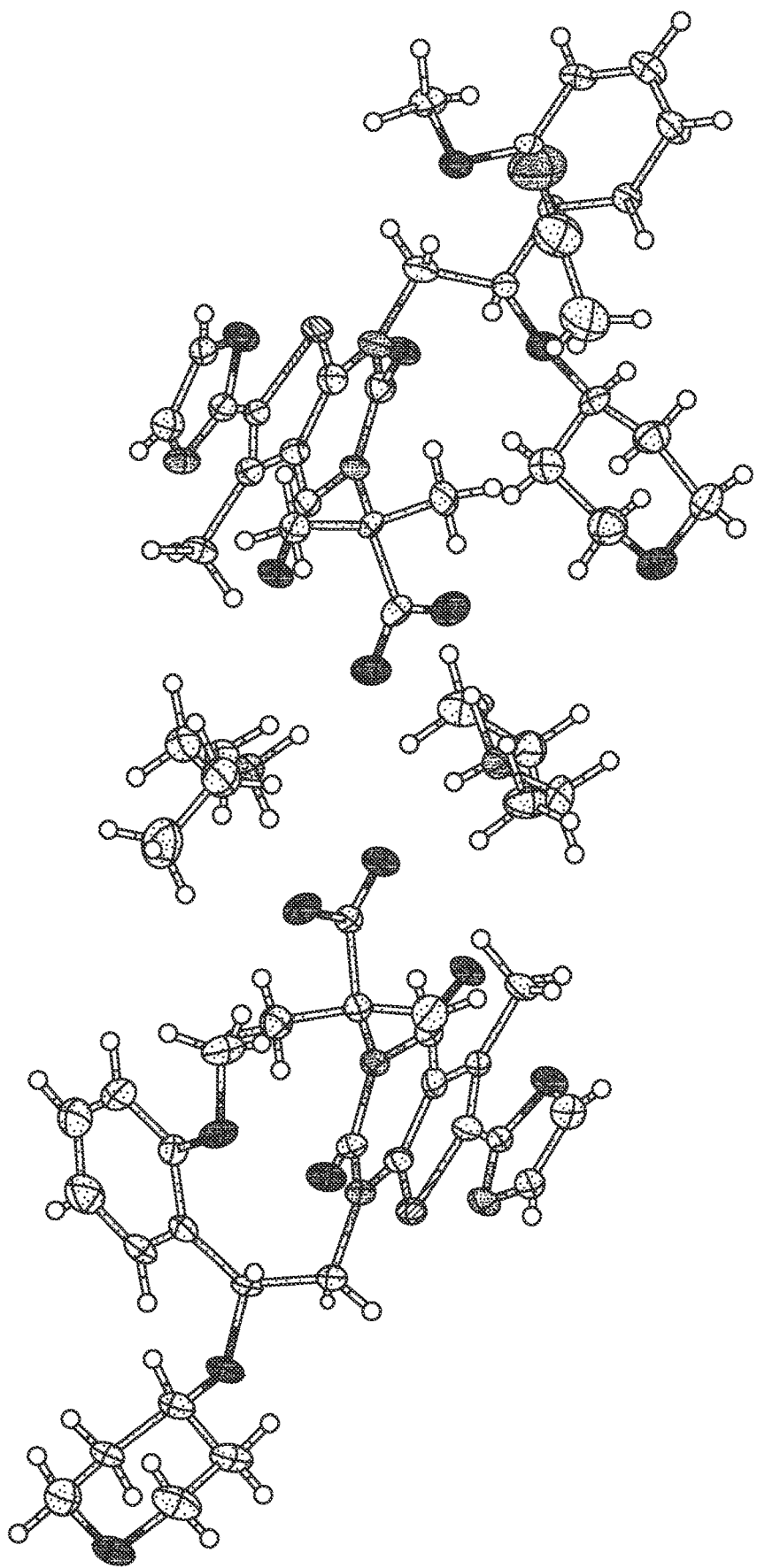
FIG. 5 shows the atomic displacement ellipsoid diagram of Compound I Diethylamine Form I.

Single crystal data was collected and is summarized in Table 1 and FIG. 5 confirming the asymmetric unit contains two Compound I anions, two ethylenediamine cations, and one acetonitrile molecule.

TABLE 1

Crystal Data and Data Collection Parameters for Compound I Diethylamine Form I

| | |
|---|---|
| Empirical formula | C33H43.50N4.50O8S |
| Formula weight (g mol$^{-1}$) | 663.28 |
| Temperature (K) | 100 (2) |
| Wavelength (Å) | 1.54184 |
| Crystal system | triclinic |
| Space group | P1 |
| Unit cell parameters | |
| a = 9.20177(14) Å | α = 82.8187(12)° |
| b = 13.6016(2) Å | β = 78.7597(12)° |
| c = 13.9089(2) Å | γ = 89.8017(12)° |
| Unit cell volume (Å3) | 1693.64(4) |
| Cell formula units, Z | 2 |
| Calculated density (g cm$^{-3}$) | 1.301 |
| Absorption coefficient (mm$^{-1}$) | 1.320 |
| F(000) | 706 |
| Crystal size (mm$^3$) | 0.42 × 0.3 × 0.25 |
| Reflections used for cell measurement | 29750 |

TABLE 1-continued

Crystal Data and Data Collection Parameters for Compound I Diethylamine Form I

| | |
|---|---|
| θ range for cell measurement | 4.3220°-77.3730° |
| Total reflections collected | 31630 |
| Index ranges | −11 ≤ h ≤ 11; −17 ≤ k ≤ 16; −17≤l≤17 |
| θ range for data collection | $θ_{min}$ = 3.276°, $θ_{max}$ = 77.552° |
| Completeness to $θ_{max}$ | 97.8% |
| Completeness to $θ_{full}$ = 67.684° | 100% |
| Absorption correction | multi-scan |
| Transmission coefficient range | 0.823-1.000 |
| Refinement method | full matrix least-squares on F$^2$ |
| Independent reflections | 11200 [$R_{int}$ = 0.0219, $R_σ$ = 0.0180 |
| Reflections [I > 2σ(I)] | 11113 |
| Reflections / restraints / parameters | 11200/3/867 |
| Goodness-of-fit on F$^2$ | S = 1.03 |
| Final residuals [I > 2σ(I)] | R = 0.0464, $R_w$ = 0.1325 |
| Final residuals [all reflections] | R = 0.0466, $R_w$ = 0.1328 |
| Largest diff. peak and hole (e Å$^{-3}$) | 0.698, −0.508 |
| Max/mean shift/standard uncertainty | 0.027/0.000 |
| Absolute structure determination | Flack parameter: 0.063(6) Hooft parameter: 0.056(6) Friedel coverage: 57.8% |

Figure 7:
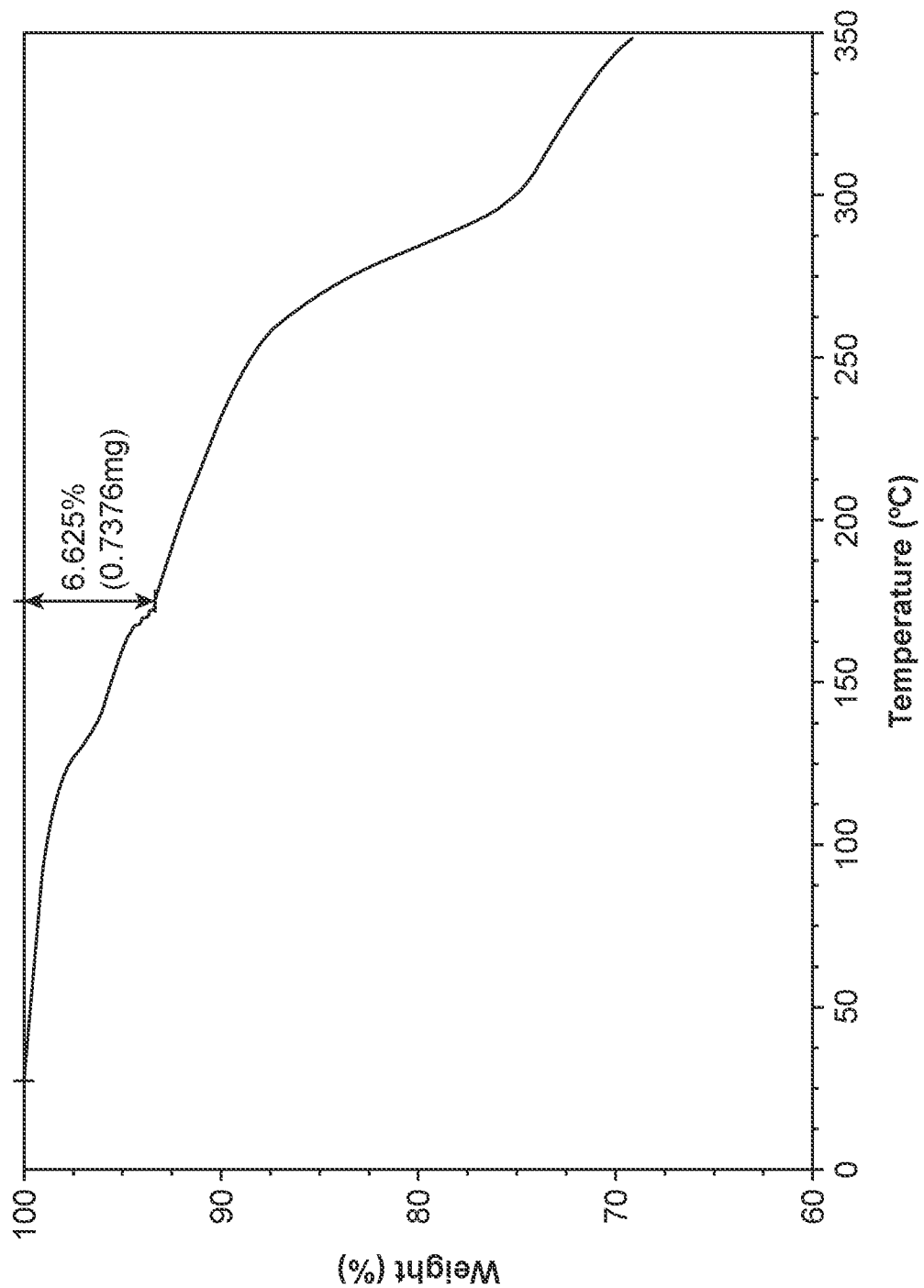
FIG. 7 shows a thermogravimetric analysis (TGA) of Compound I Diethylamine Form I.

The DSC curve is shown in FIG. 6 and indicates multiple endothermic transitions with onsets at about 135° C. and about 171° C. The TGA curve is shown in FIG. 7 and displays a weight loss (about 6.6% room temperature to 175° C.) attributed to loss of acetonitrile.

Example 11: Compound I N,N-Dibenzylethylenediamine Form I

The N,N-dibenzylethylenediamine salt/cocrystal (anisole solvate) of Compound I ("Compound I N,N-Dibenzylethylenediamine Form I") was obtained when 2 mL of anisole was added to 48.4 mg of Compound I (prepared as described in U.S. Patent Publication No. 2017/0267690, titled "Solid Forms of a Thienopyrimidinedione ACC Inhibitor and Methods for Production Thereof," filed on Mar. 1, 2017, which is hereby incorporated by reference in its entirety) at about 60° C. followed by the addition of 21 μL of N,N-dibenzylethylenediamine. The mixture was slurried at about 40° C. for about 6 days followed by cooling to room temperature and allowing the mixture to age without stirring for about 22 days. The XRPD pattern of the resulting product, Compound I N,N-dibenzylethylenediamine Form I, is shown in FIG. 8.

Figure 10:
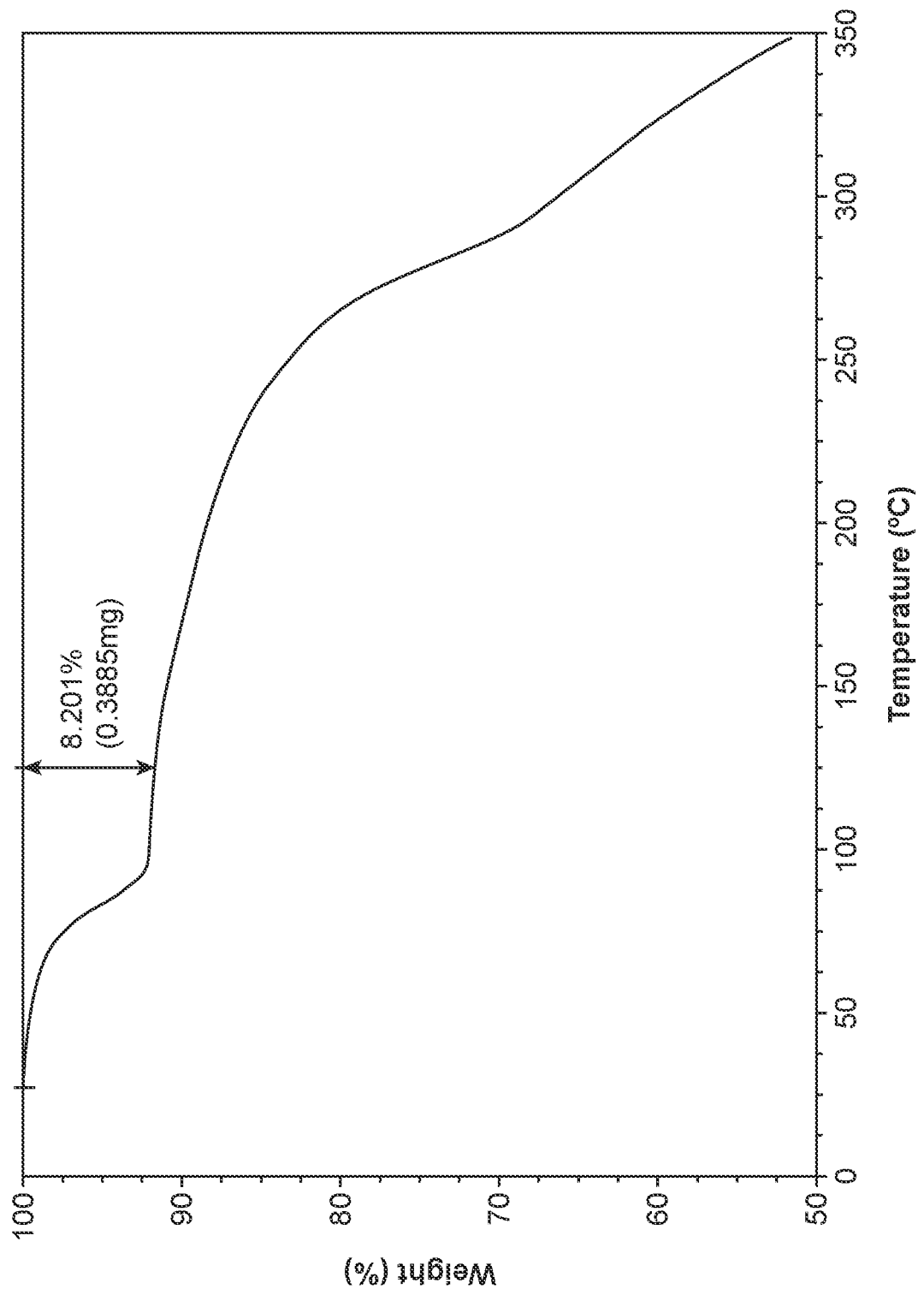
FIG. 10 shows a thermogravimetric analysis (TGA) of Compound I N,N-Dibenzylethylenediamine Form I.

The DSC curve is shown in FIG. 9 and indicates an endothermic transition with onset at about 81° C. The TGA curve is shown in FIG. 10 and displays a weight loss (about 8.2% room temperature to 125° C.) attributed to loss of volatiles. $^1$H NMR data suggests Compound I N,N-Dibenzylethylenediamine Form I is a Compound I:N,N-dibenzylethylenediamine phase of a 2:1 ratio.

Example 12: Compound I Ethanolamine Form I

The ethanolamine salt/cocrystal (solvate) of Compound I ("Compound I Ethanolamine Form I") was obtained when 53.8 mg of Compound I (prepared as described in U.S. Patent Publication No. 2017/0267690, titled "Solid Forms of a Thienopyrimidinedione ACC Inhibitor and Methods for Production Thereof," filed on Mar. 1, 2017, which is hereby incorporated by reference in its entirety), was dissolved in 2 mL of EtOAc at about 55° C. followed by the addition of 5.50 µL ethanolamine and cooling the solution to room temperature. The XRPD pattern of the resulting product, Compound I Ethanolamine Form I, is shown in FIG. 11.

Figure 13:
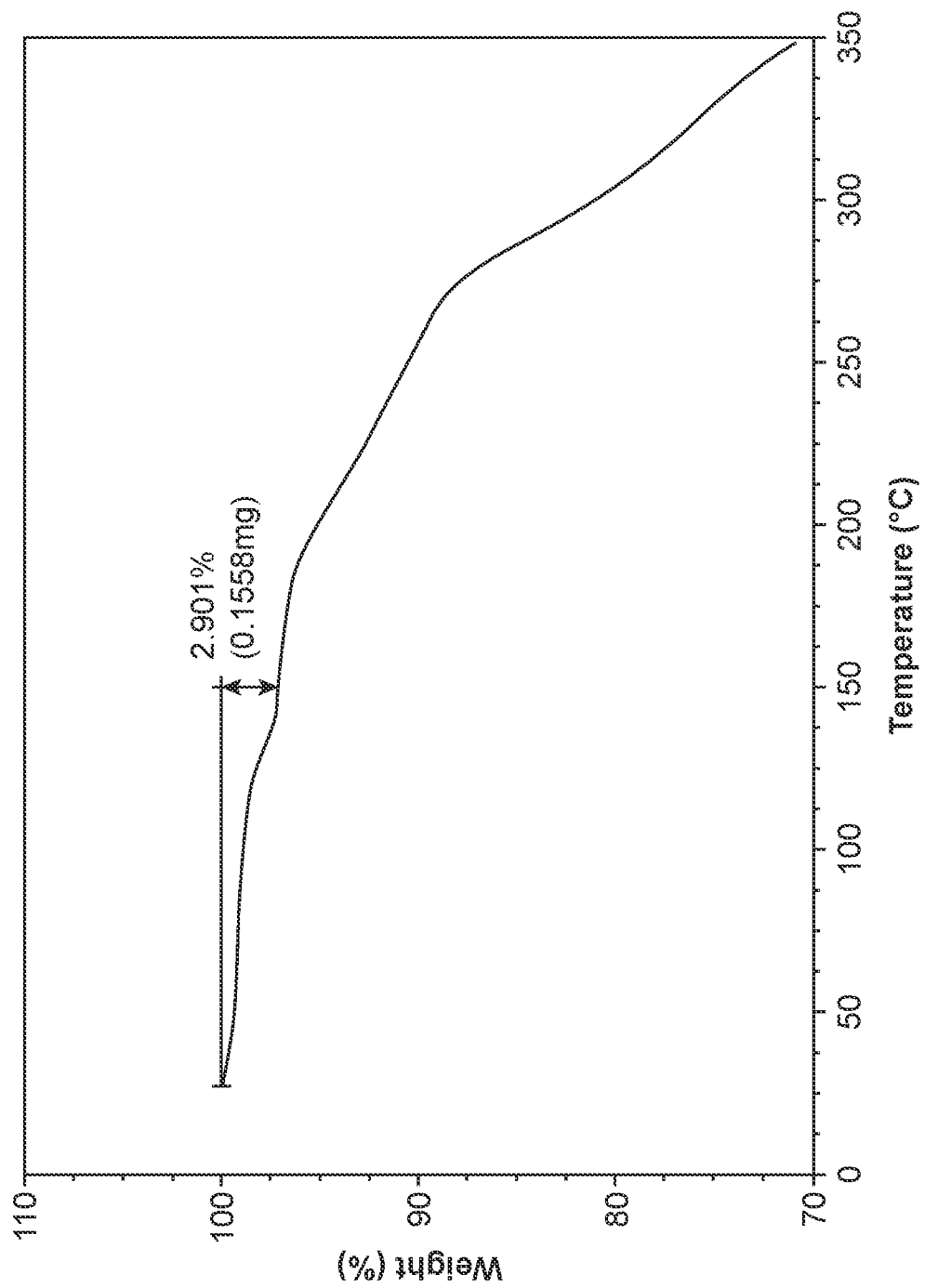
FIG. 13 shows a thermogravimetric analysis (TGA) of Compound I Ethanolamine Form I.

The DSC curve is shown in FIG. 12 and indicates multiple endothermic transitions with onsets at about 22° C. and about 133° C. The TGA curve is shown in FIG. 13 and displays a weight loss (about 2.9% room temperature to 150° C.) attributed to loss of volatiles. $^1$H NMR data suggests Compound I Ethanolamine Form I is a Compound I:ethanolamine phase of a 1:1 ratio.

Example 13: Compound I Form IX

Compound I Form IX was isolated by slurrying Compound I Form I (prepared as described in U.S. Patent Publication No. 2017/0267690) in dimethylacetamide at room temperature for around 3 days.

Figure 16:
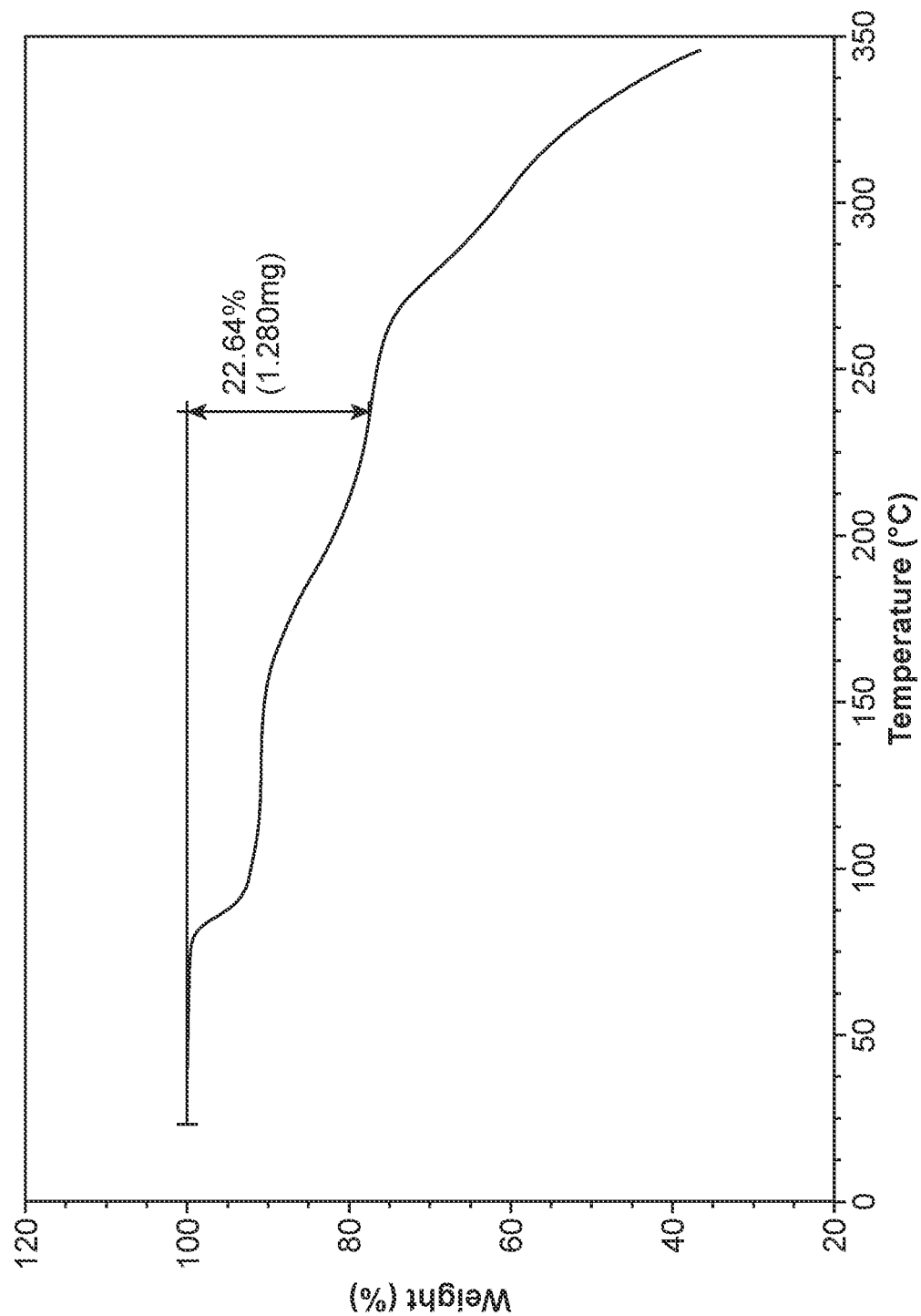
FIG. 16 shows a thermogravimetric analysis (TGA) of Compound I Form IX.
Figure 17:
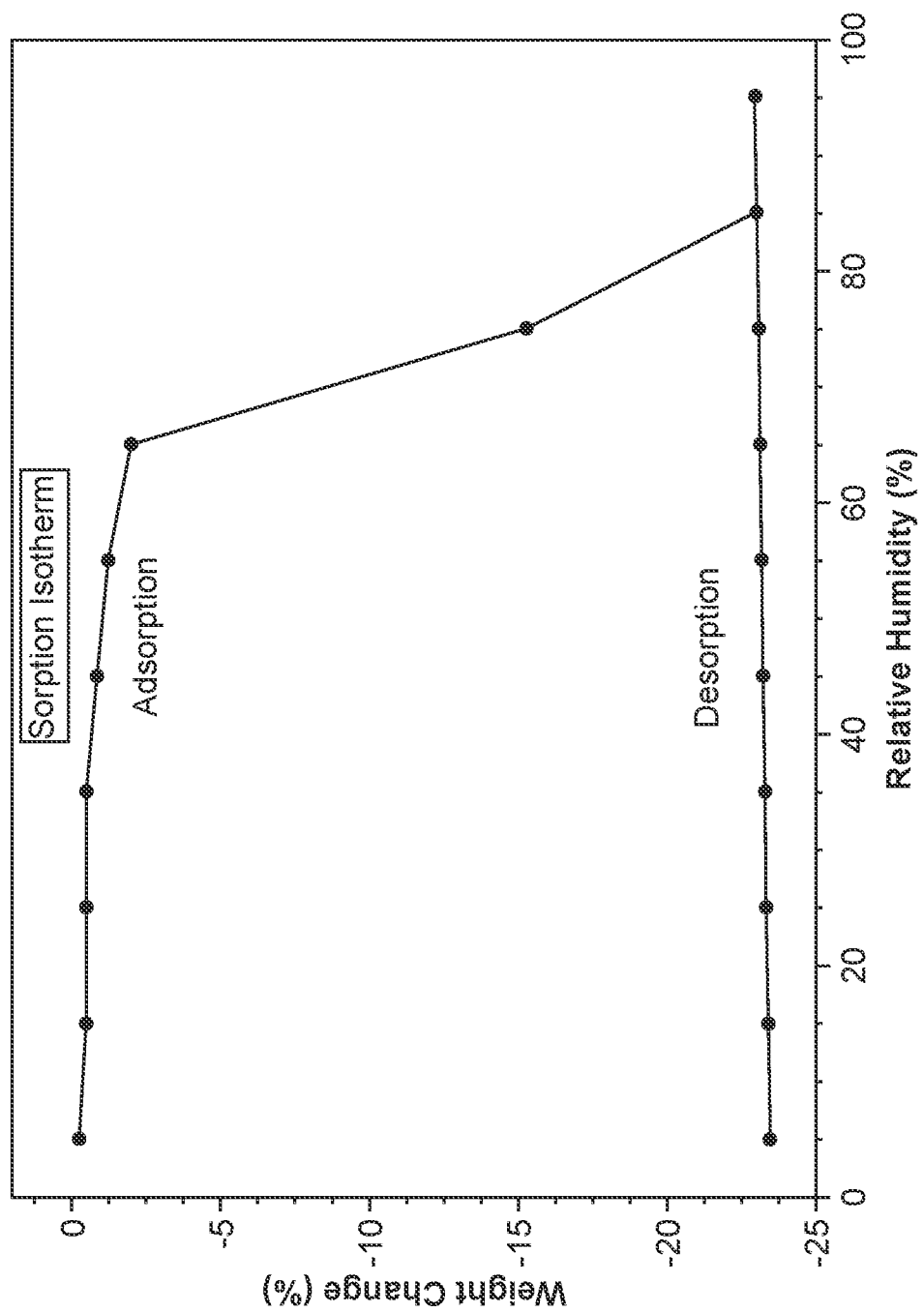
FIG. 17 shows a dynamic vapor sorption (DVS) of Compound I Form IX.

The DSC curve of Compound I Form IX, which is shown in FIG. 15, indicates an endothermic transition at 85° C. (onset) attributed to desolvation and melt. The TGA curve, which is shown in FIG. 16, shows a weight loss (23%, room temperature to 235° C.) indicating a solvate that was identified as dimethylacetamide and based on TGA-MS. The moisture sorption curve is shown in FIG. 17 and indicates that the form slowly desolvated up to 95% relative humidity (losing around 23% weight). XRPD analysis of the sample after the DVS experiment shows that the material converted to Compound I Form I as described in U.S. Patent Publication No. 2017/0267690.

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence.

What is claimed is:

1. A method for preparing a compound of formula (N):

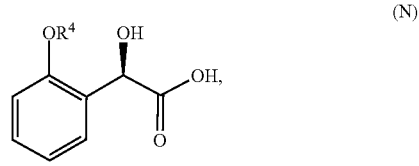

wherein $R^4$ is $C_{1-3}$ alkyl, comprising:
(a) contacting a compound of formula (U):

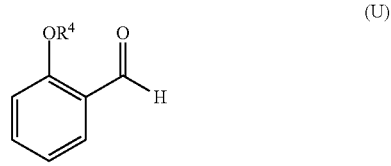

with a hydroxynitrilase and a hydrogen cyanide source under conditions sufficient to form a compound of formula (T):

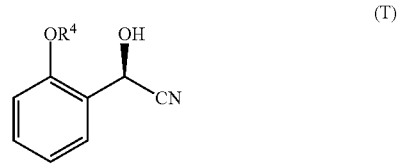

and (b) contacting a compound of formula (T) with a nitrilase under conditions sufficient to form a compound of formula (N).

2. The method of claim 1, wherein $R^4$ is methyl.

* * * * *